(12) United States Patent
Fahmy et al.

(10) Patent No.: US 9,603,800 B2
(45) Date of Patent: Mar. 28, 2017

(54) METHODS OF TREATING INFLAMMATORY AND AUTOIMMUNE DISEASES AND DISORDERS USING NANOLIPOGELS

(71) Applicant: Yale University, New Haven, CT (US)

(72) Inventors: Tarek M. Fahmy, New Haven, CT (US); Michael Look, Seattle, WA (US); Joseph Craft, Hamden, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/394,147

(22) PCT Filed: Apr. 12, 2013

(86) PCT No.: PCT/US2013/036494
§ 371 (c)(1),
(2) Date: Oct. 13, 2014

(87) PCT Pub. No.: WO2013/155493
PCT Pub. Date: Oct. 17, 2013

(65) Prior Publication Data
US 2015/0118318 A1    Apr. 30, 2015

Related U.S. Application Data

(60) Provisional application No. 61/623,486, filed on Apr. 12, 2012, provisional application No. 61/747,624, (Continued)

(51) Int. Cl.
*A61K 9/127* (2006.01)
*A61K 47/24* (2006.01)
(Continued)

(52) U.S. Cl.
CPC .......... *A61K 9/1273* (2013.01); *A61K 9/1271* (2013.01); *A61K 9/1277* (2013.01);
(Continued)

(58) Field of Classification Search
CPC ...... A61K 9/1271; A61K 9/1277; A61K 8/17; B82Y 5/00
See application file for complete search history.

(56) References Cited

U.S. PATENT DOCUMENTS 5,128,355 A    7/1992  Carini
5,138,069 A    8/1992  Carini
(Continued)

FOREIGN PATENT DOCUMENTS

EP    2177230    4/2010
EP    2389928    11/2011
(Continued)

OTHER PUBLICATIONS

Anderson and Shive, et al., "Biodegradation and biocompatibility of PLA and PLGA microspheres", Adv Drug Deliv Rev, 28(1):5-24 (1997).
(Continued)

*Primary Examiner* — Carlos Azpuru
(74) *Attorney, Agent, or Firm* — Pabst Patent Group LLP

(57) ABSTRACT

Compositions and methods for treating or ameliorating the symptoms of inflammatory or autoimmune disease or disorder are described herein. The compositions contain a nanolipogel for sustained delivery of an effective amount of one or more active agents of choice, preferably a drug for treating or ameliorating the symptoms of inflammatory or autoimmune disease or disorder. The nanolipogel includes a lipid bilayer surrounding a hydrogel core, which may optionally include a host molecule, for example, an absorbent such as a cyclodextrin or ion-exchange resin. In preferred embodiments at least one of active agents is an immunosuppressant.

58 Claims, 61 Drawing Sheets

Related U.S. Application Data filed on Dec. 31, 2012, provisional application No. 61/747,614, filed on Dec. 31, 2012.

(51) Int. Cl.
| | | |
|---|---|---|
| A61K 47/40 | (2006.01) | |
| A61K 47/48 | (2006.01) | |
| B82Y 5/00 | (2011.01) | |
| A61K 38/18 | (2006.01) | |
| A61K 38/20 | (2006.01) | |
| A61K 31/343 | (2006.01) | |

(52) U.S. Cl.
CPC ........ *A61K 31/343* (2013.01); *A61K 38/1841* (2013.01); *A61K 38/2013* (2013.01); *A61K 47/24* (2013.01); *A61K 47/40* (2013.01); *A61K 47/48176* (2013.01); *A61K 47/48969* (2013.01); *B82Y 5/00* (2013.01)

(56) References Cited

U.S. PATENT DOCUMENTS

| | | |
|---|---|---|
| 5,153,197 A | 10/1992 | Carini |
| 5,155,118 A | 10/1992 | Carini |
| 5,210,079 A | 5/1993 | Carini |
| 5,354,867 A | 10/1994 | Carini |
| 7,052,694 B2 | 5/2006 | Pease |
| 7,390,888 B2 | 6/2008 | Pease |
| 7,411,051 B2 | 8/2008 | Rosen |
| 8,114,845 B2 | 2/2012 | Langermann |
| 8,263,125 B2 | 9/2012 | Vaya |
| 8,609,089 B2 | 12/2013 | Langermann |
| 8,709,416 B2 | 4/2014 | Langermann |
| 2004/0071761 A1 | 4/2004 | Miller |
| 2006/0099203 A1 | 5/2006 | Pease |
| 2006/0110383 A1 | 5/2006 | Honjo |
| 2007/0014845 A1* | 1/2007 | Zhang et al. ............... 424/450 |
| 2007/0166281 A1 | 7/2007 | Kosak |
| 2007/0219122 A1 | 9/2007 | Glazer |
| 2008/0050920 A1 | 2/2008 | Kawahara |
| 2008/0187595 A1 | 8/2008 | Jordan |
| 2009/0004213 A1 | 1/2009 | Singh |
| 2011/0262406 A1 | 10/2011 | delCampo |
| 2015/0064265 A1 | 3/2015 | Fahmy |
| 2015/0118318 A1 | 4/2015 | Fahmy |

FOREIGN PATENT DOCUMENTS

| | | |
|---|---|---|
| EP | 2494960 | 9/2012 |
| WO | 9515746 | 6/1995 |
| WO | 03099196 | 12/2003 |
| WO | 2004004771 | 1/2004 |
| WO | 2004056875 | 7/2004 |
| WO | 2006121168 | 11/2006 |
| WO | 2006133396 | 12/2006 |
| WO | 2007005754 | 1/2007 |
| WO | 2007005874 | 1/2007 |
| WO | 2007056539 | 5/2007 |
| WO | 2007072286 | 6/2007 |
| WO | 2008083174 | 7/2008 |
| WO | 2009014708 | 1/2009 |
| WO | 2009073533 | 6/2009 |
| WO | 2010083337 | 7/2010 |
| WO | 2012009611 | 1/2012 |
| WO | 2012068531 | 5/2012 |
| WO | 2015066535 | 5/2015 |

OTHER PUBLICATIONS

Blanco, et al., "Nanomedicine in cancer therapy: innovative trends and prospects", Cancer Sci, 102(7):1247-52 (2011).
Blanco, et al., "Induction of dendritic cell differentiation by IFN-alpha in systemic lupus erythematosus", Science, 294(5546):1540-3 (2001).
Capurso, et al., "Development of a nanoparticulate formulation of retinoic acid that suppresses Th17 cells and upregulates regulatory T cells", Self Nonself, 1:4:335-40 (2010).
Chen, et al. "Evaluation of ion-exchange microspheres as carriers for the anticancer drug doxorubicin: in vitro studies." J. Pharm. Pharmacol. 44(3):211-5 (1992).
Demento, et al., "Inflammasome-activating nanoparticles as modular systems for optimizing vaccine efficacy", Vaccine, 27(23):3013-21 (2009).
Elbarbry, et al., "Liquid chromatographic determination of mycophenolic acid and its metabolites in human kidney transplant plasma: pharmacokinetic application", J Chromatogr B Analyt Technol Biomed Life Sci, 859(2):276-81(2007).
Fahmy, et al., "Targeted for drug delivery", Materials Today, 8(8):18-26 (2005).
Farag, et al. "Rate of release of organic carboxylic acids from ion exchange resins" J. Pharm. Sci. 77(10):872-5(1988).
Filler, et al., "Random pharmacokinetic profiles of EC-MPS in children with autoimmune disease", Pediatric Rheumatol., 8:1 (2010).
Ginzler, et al., "Mycophenolate mofetil or intravenous cyclophosphamide for lupus nephritis", N Engl J Med, 353(21):2219-28 (2005).
Hu, et al., "Reaction parameters of targeted gene repair in mammalian cells", Mol. Biotech., 29:197-210 (2005).
Jonsson, et al., "Inosine monophosphate dehydrogenase (IMPDH) inhibition in vitro suppresses lymphocyte proliferation and the production of immunoglobulins, autoantibodies and cytokines in splenocytes from MRLlpr/lpr mice", Clin Exp Immunol, 124(3):486-91 (2001).
Jonsson, et al., "Mycophenolic acid inhibits inosine 5'-monophosphate dehydrogenase and suppresses immunoglobulin and cytokine production of B cells", Int Immunopharmacol, 3(1):31-7 (2003).
Karnell, et al., "Mycophenolic acid differentially impacts B cell function depending on the stage of differentiation", J Immunol, 187(7):3603-12 (2011).
Lagaraine, et al., "Mycophenolic acid-treated human dendritic cells have a mature migratory phenotype and inhibit allogeneic responses via direct and indirect pathways", Int Immunol, 17(4):351-63 (2005).
Lagaraine, et al., "Induction of human CD4+ regulatory T cells by mycophenolic acid-treated dendritic cells", J Leukoc Biol, 84(4):1057-64 (2008).
Lee, et al., "Induction and maintenance therapy for lupus nephritis: a systematic review and meta-analysis", Lupus, 19(6):703-10 (2010).
Lipsky, "Mycophenolate mofetil", Lancet, 348:L1357-9 (1996).
Look, et al., "Application of nanotechnologies for improved immune response against infectious diseases in the developing world", Adv Drug Deilv Rev, 62(4-5):378-93 (2010).
Lui, et al., "Effect of mycophenolate mofetil on severity of nephritis and nitric oxide production in lupus-prone MRL/lpr mice", Lupus, 11(7):411-8 (2002).
Lund, et al., "Toll-like receptor 9-mediated recognition of Herpes simplex virus-2 by plasmacytoid dendritic cells", J Exp Med, 198(3):513-20 (2003).
Maurer, et al., "Developments in liposomal drug delivery systems", Expert Opin Biol Ther., 1(6):923-47 (2001).
Mehling, et al., Mycophenolate mofetil impairs the maturation and function of murine dendritic cells\, J Immunol, 165(5):2374-81 (2000).
Monneaux, et al., "Molecular therapies for systemic lupus erythematosus: clinical trials and future prospects", Arthritis Res Ther, 11(3):234 (2009).
Moroni, et al., "A randomized pilot trial comparing cyclosporine and azathioprine for maintenance therapy in diffuse lupus nephritis over four years", Olin J Am Soc Nephrol, 1(5):925-32 (2006).
Navarra, et al., "Efficacy and safety of belimumab in patients with active systemic lupus erythematosus: a randomised, placebo-controlled, phase 3 trial", Lancet, 377(9767):721-31 (2011).

(56) References Cited

OTHER PUBLICATIONS

Olsen, et al., "Genomic sequence correction by single-stranded DNA oligonucleotides: role of DNA synthesis and chemical modifications of the oligonucleotide ends". J. Gene Med., 7:1534-44 (2005).
Opal and DePalo, "Anti-inflammatory cytokines", Chest, 117(4):1162-72 (2000).
Peer, et al., "Systemic leukocyte-directed siRNA delivery revealing cyclin D1 as an anti-inflammatory target", Science, 319:627-30 (2008).
Quemeneur, et al., Mycophenolic acid inhibits IL-2-dependent T cell proliferation, but not IL-2-dependent survival and sensitization to apoptosis\, J Immunol, 169(5):2747-55 (2002).
Rahman, et al., "Systemic lupus erythematosus", N Engl J Med, 358(9):929-39 (2008).
Ramos, et al., "Modulation of autoantibody production by mycophenolate mofetil: effects on the development of SLE in (NZB x NZW)F1 mice", Nephrol Dial Transplant, 18(5):878-83 (2003).
Ronnblom, et al., "Cytokines as therapeutic targets in SLE", Nat Rev Rheumatol, 6(6):339-47 (2010).
Sawhney, et al., "Bioerodible hydrogels based on photopolymerized poly (ethylene glycol)-co-poly(.alpha.-hydroxy acid) diacrylate macromers", Macromolecules, 26:581-7 (1993).
Scindia, et al., "Anti-alpha8 integrin immunoliposomes in glomeruli of lupus-susceptible mice: a novel system for delivery of therapeutic agents to the renal glomerulus in systemic lupus erythematosus", Arthritis Rheum, 58(12):3884-91 (2008).
Serkova, et al., "Renal inflammation: targeted iron oxide nanoparticles for molecular MR imaging in mice", Radiology, 255(2):517-26 (2010).
Sfikakis, et al., "Rituximab anti-B-cell therapy in systemic lupus erythematosus: pointing to the future", Curr Opin Rheumatol, 17(5):550-7 (2005).
Shirali, et al., "Nanoparticle delivery of mycophenolic acid upregulates PD-L1 on dendritic cells to prolong murine allograft survival", Am J Transplant, 11(12):2582-92 (2011).
Shlomchik, et al., "From T to B and back again: positive feedback in systemic autoimmune disease", Nat Rev Immunol, 1(2):147-53 (2001).
Teichmann, et al., "Dendritic cells in lupus are not required for activation of T and B cells but promote their expansion, resulting in tissue damage", Immunity, 33(6):967-78 (2010).
Triantafyllopoulou, et al., "Proliferative lesions and metalloproteinase activity in murine lupus nephritis mediated by type I interferons and macrophages", PNAS, 107(7):3012-7 (2010).
Wadia, et al., "Mycophenolic acid inhibits maturation and function of human dendritic cells and B cells", Hum Immunol, 70(9):692-700 (2009).
Wofsy, et al., "Successful treatment of autoimmunity in NZB/NZW F1 mice with monoclonal antibody to L3T4", J Exp Med, 161(2):378-91 (1985).
Wofsy, et al., "Reversal of advanced murine lupus in NZB/NZW F1 mice by treatment with monoclonal antibody to L3T4", J Immunol, 138(10):3247-53 (1987).
Yoshida, et al., "Effect of poly(lactic-co-glycolic acid) contact on maturation of murine bone marrow-derived dendritic cells", J Biomed Mater Res A, 80(1):7-12 (2007).
Altincicek, et al., "Identification of collagen IV derived danger/alarm signals in insect immunity by nanoLC-FTICR MS", Biol Chem., 390:1303-11 (2009).
Argyo, et al., "Multifunctional Mesoporous Silica Nanoparticles as a Universal Platform for Drug Delivery", Chem. Mater., 26(1):435-451 (2014).
Aubert, et al., "Antigen-specific CD4 T-cell help rescues exhausted CD8 T cells during chronic viral infection", PNASi, 108:21182-7 (2011).
Barbe, et al., "Silica Particles: A Novel Drug-Delivery System", Advanced Materials, 16(21):1959-66 (2004).

Berger et al., "Phase I safety and pharmacokinetic study of CT-011, a humanized antibody interacting with PD-1, in patients with advanced hematologic malignancies", Clin. Cancer Res., 14:3044-51 (2008).
Bonifaz, et al., "Efficient targeting of protein antigen to the dendritic cell receptor DEC-205 in the steady state leads to antigen presentation on major histocompatibility complex class I products and peripheral CD8+ T cell tolerance", J. Exp. Med., 196(12)1627-38 (2002).
Bonifaz, et al., "In vivo targeting of antigens to maturing dendritic cells via the DEC-205 receptor improves T cell vaccination", J. Exp. Med., 199(6):815-24 (2004).
Braumuller, et al., "T-helper-1-cell cytokines drive cancer into senescence", Nature, 494:361-365 (2012).
Butte, et al., "Programmed death-1 ligand 1 interacts specifically with the B7-1 costimulatory molecule to inhibit T cell responses", Immunity, vol. 27, pp. 111-122, (2007).
Chen, et al., "A facile construction strategy of stable lipid nanoparticles for drug delivery using a hydrogel-thickened microemulsion system", Nanotechnoiogy 21(1): ):015101. doi: 10.1088/0957-4484/21/1/015101 (2010).
Clarke, et al., "Cancer stem cells—perspectives on current status and future directions: AACR Workshop on cancer stem cells", Cancer Res., 66:9339-9344 (2006).
Corradetti, et al., "Paracrine signaling events in embryonic stem cell renewal mediated by affinity targeted nanoparticles", Biomaterials, 33(28):6634-43 (2012).
Corthay, et al., "Primary antitumor immune response mediated by CD4+ T cells", Immunity, 22, 371-83 (2005).
Cubillos-Ruiz, et al., "Polyethylenimine-based siRNA nanocomplexes reprogram tumor-associated dendritic cells via TLR5 to elicit therapeutic antitumor immunity", J. Clin. Invest. 119(8): 2231-44 (2009).
Curiel, "Regulatory T cells and treatment of cancer", Curr. Opin. Immunol., 20(2):241-6 (2008).
DaCosta, et al., "SB-505124 is a selective inhibitor of transforming growth factor-beta type I receptors ALK4, ALK5, and ALK7", Mol Pharmacol. 65:744-52 (2004).
Dalerba, et al., "Cancer stem cells: models and concepts", Annu. Rev. Med., 58:267-84 (2007).
Danhier, et al., "PLGA-based nanoparticles: an overview of biomedical applications", J. Control Release, 161(2):505-22 (2012).
De Rezende, et al., "Regulatory T cell as a target for cancer therapy", Arch. Immunol. Ther. Exp., 58(3):179-90 (2010).
Demento, et al., "Role of sustained antigen release from nanoparticle vaccines in shaping the T cell memory phenotype", Biomaterials, 33(19):4957-64 (2012).
Egilmez, et al., "Cytokine immunotherapy of cancer with controlled release biodegradable microspheres in a human tumor xenograft/SCID mouse model,", Cancer Immunol Immunotherapy, 46(1):21-4 (1998).
Elamanchili, et al., "Characterization of poly(D,L-lactic-co-glycolic acid) based nanoparticulate system for enhanced delivery of antigens to dendritic cells", Vaccine, 22(19):2406-12 (2004).
Erbe, et al., "Small molecule ligands define a binding site on the immune regulatory protein B7.1.", J. Biol. Chem., 277:7363-8 (2002).
Freeman, "Structures of PD-1 with its ligands: sideways and dancing cheek to cheek", PNAS, 105:10275-6 (2008).
Frey, et al., "Signaling defects in anti-tumor T cells", Immunol. Rev., 222:192-205 (2008).
Gorelik, et al., "Immune-mediated eradication of tumors through the blockade of transforming growth factor-beta signaling in T cells", Nat Med., 7(10):1118-22 (2001).
Grell, et al., "The transmembrane form of tumor necrosis factor is the prime activating ligand of the 80 kDa tumor necrosis factor receptor", Cell, 83:793-802 (1995).
Guo, et al., "[Losartan downregulates the expression of transforming growth factor beta type I and type II receptors in kidney of diabetic rat].", Zhonghua Nei Ke Za Zhi, 42:403-8 (2003).
Hamidi, et al., "Hydrogel nanoparticles in drug delivery", Adv Drug Deily Rev., 60(15):1638-49 (2008).

(56) References Cited

OTHER PUBLICATIONS

Hawiger, et al., "Dendritic cells induce peripheral T cell unresponsiveness under steady state conditions in vivo", J. Exp. Med., 194(6):769-79 (2001).
Health Day, "Blood pressure drug might boost chemo success, mouse study suggests", http://consumer.healthday.com/circulatory-system-information-7/blood-pressure-news-70/blood-pressure-drug-might-boost-chemo-success-mouse-study-suggests-680633.html,Retrieved from the internet Oct. 2, 2013.
Honeychurch, et al., "Anti-CD40 monoclonal antibody therapy in combination with irradiation results in a CD8 T-cell-dependent immunity to B-cell lymphoma", Blood, 102:1449-1457 (2003).
Hunder, et al., "Treatment of metastatic melanoma with autologous CD4+ T cells against NY-ESO-1", NEJM, 358:2698-2703 (2008).
Jain, et al., "Nanolipobeads bases drug delivery system for effective management of peptic ulcer", Intl J Curr Pharmaceutical Res., 3(2):141-9 (2011).
Joshi, et al., "Targeting tumor antigens to dendritic cells using particulate carriers", J. Control Release, 161(1):25-37 (2012).
Kahn, "CD4+ T cell clones specific for the human p97 melanoma-associated antigen can eradicate pulmonary metastases from a murine tumor expressing the p97 antigen", J Immunol, 146:3235-41 (1991).
Kong, et al., "Combination therapy with losartan and piog;otazone additively reduces renal oxidative and nitrative stress induced by chronic high fat, sucrose, and sodium intake", Oxid Med Cell. Longev, doi: 10.1155/2012/856085 (2012).
Lazar-Molnar, et al., "Crystal structure of the complex between programmed death-1 (PD-1) and its ligand PD-L2", PNAS, 105:10483-8 (2008).
Look, et al., "Nanogel-based delivery of mycophenolic acid ameliorates systemic lupus erythematosus in mice", J. Clin Invest., 123(4):1741-9 (2013).
Look, et al., "The nanomaterial-dependent modulation of dendritic cells and its potential influence on therapeutic immunosuppression in lupus", Biomaterials, 35(3):1089-95 (2014).
Losartan, from Wikipedia encyclopedia, https://en.wikipedia.org/wiki/Losartan, 4 pages, retrieved from the internet Oct. 22, 2013.
Luchini, et al. "Smart hydrogel nanoparticles for serum cancer biomarkers harvesting", AACR annual meeting, Apr. 14-18, Los Angles Ca, 2007.
Matreya, "1,2-Distearoylphosphatidylethanolamine-methyl-polyethyleneglycol conjugate-200(Na+salt)", http://www.matreya.com/ProductInfo.aspx?peoductid=1439, 2 pages, retrieved from the Internet Mar. 30, 2012.
Mougiakakos, et al., "Regulatory T cells in cancer", Adv Cancer Res, 107:57-117 (2010).
Nagaraj, et al., "Anti-inflammatory triterpenoid blocks immune suppressive function of MDSCs and improves immune response in cancer", Clin Cancer Res.,, 16(6):1812-23 (2010).
Nesbeth, et al., "CD4+ T cells elicit host immune responses to MHC class II-negative ovarian cancer through CCL5 secretion and CD40-mediated licensing of dendritic cells", J Immunol.,, 184:5654-62 (2010).
Oda, et al., "Transforming growth factor $^2$ (TGF-$^2$) and regulatory T cells (Treg): The interface of tumor and host immunity," European journal of clinical & medical oncology 4(1):27-32 (2011).
Park, "Rationally engineered nanoparticles for therapeutic modulation of transforming growth factor beta signaling", Dissertation confidentially presented May 2011, not publically available other than abstract from ProQuest UMI No. 3467563, pp. 1-25 only distributed to one party prior to filing of U.S. Appl. No. 61/623,486 on Apr. 12, 2012.
Patel,et al., "Review on hydrogel nanoparticles in drug delivery" AJPTR, 1(3):19-38 (2011).
Perez-Diez, "CD4 cells can be more efficient at tumor rejection than CD8 cells",, Blood, 109:5346-54 (2007).
Petersen, et al., "Accumulation in tumor tissue of adoptively transferred T cells: A comparison between intravenous and intraperitoneal injection", J Immunother 29, 241-9 (2006).
Punyamoonwongsa and Tighe, "A smart hydrogel-based system for controlled drug release", Chiang Mai J Sci., 32(3):471-8 (2005).
Rehman, et al., "Angiotensin Type 2 receptor agonist compound 21 reduces vascular injury and myocardial fibrosis in stroke-prone spontaneously hypertensive rats", Hypertension, 59(2):291-9 (2012).
Ruoslahti, et al., "RGD and other recognition sequences for integrins", Annu. Rev. Cell Dev. Biol., 12:697-715 (1996).
Ruoslahti, et al., "Specialization of tumour vasculature", Nat. Rev. Cancer, 2:83-90 (2002).
Sammartino, et al., "Anti-GBM disease following CTLA4 blockade in a patient with metastatic melanoma", Clinical Kidney J, 3(2):135-137 (2010).
Samstein, et al., "The use of deoxycholic acid to enhance the oral bioavailability of biodegradable nanoparticles", Biomaterials., 29(6):703-8 (2008).
Schneider, et al., "Conversion of membrane-bound Fas(CD95) ligand to its soluble form is associated with downregulation of its proapoptotic activity and loss of liver toxicity", J. Exp. Med.,187:1205-121 (1998).
Selleckchem,"TGF-beta/Smad Inhibitors" http://www.selleckchem.com/products/sb-505124.html, 4 pages, Retrieved from the internet Oct. 22, 2013.
Shafer-Weaver, et al., "Immunity to murine prostatic tumors: continuous provision of T-cell help prevents CD8 T-cell tolerance and activates tumor-infiltrating dendritic cells", Cancer Research, 69:6256-64 (2009).
Tanaka, et al., "Downregulation of Fas ligand by shedding", Nat. Med., 4: 31-36 (1998).
Torchilin, et al., "Multifunctional nanocarriers", Adv Drug Deliv Rev., 58(14):1532-55 (2006).
Trevelyan, et al., "Effect of enalapril and losartan on cytokines in patients with stable angina pectoris awaiting coronary artery bypass grafting and their interaction with polymorphisms in the interleukin-6 gene", Am J Caridol., 94(5):564-9 (2004).
Vonderheide, "Prospect of targeting the CD40 pathway for cancer therapy", Clin Cancer Res, 13(4):1083-1088 (2007).
Wang, et al., "Immune suppression by tumor-specific CD4+ regulatory T-cells in cancer", Semin Cancer Biol., 16:73-9 (2006).
Willimsky, et al., "The adaptive immune response to sporadic cancer", Immunol. Rev., 220:102-12 (2007).
Yang, et al., "Preparation of gel-core-solid lipid nanoparticle: A novel way to improve the encapsulation of protein and peptide", Chem Pharm Bull., 58(9):1195-202 (2010).
Ziai, et al., "Renal allograft protection with losartan in Fisher Lewis rats: Hemodynamics, macrophages, and cytokines", Kidney Int., 57(6):2618-25.
Cavalli, et al., "Solid lipid nanoparticies as carriers of hydrocortisone and progesterone complexes with $^2$-cyclodextrins", Intl J Pharma., 182:59-69 (1999).
Clawson, et al., "Synthesis and characterization of lipid-polymer hybrid nanoparticles with pH-triggered PeG shedding", Langmuir, 27(17):10556-61 (2011).
De Miguel, et al., "Proofs of the structure of lipid coated nanoparticles (SMBV) used as drug carriers", Pharma. Res., 17(7):817-24 (2000).
Diop-Frimpong, et al., "Losartan inhibits collagen I synthesis and improves the distribution and efficacy of nanotherapeutics in tumors", PNAS, 108(7):2909-14 (2011).
Flavell, et al., "The polarization of immune cells in the tumour enviroment by TGF$^2$", Nat Rev Immunool., 10(8):1-27 (2010).
Hoare, et al., "Hydrogels in drug delivery: Process and challenges", Polymer, 49:1993-2007 (2008).
Hong, "Lipid-hydrogel nanoparticles synthesis methods and characterization",Theses from DRUM, pp. 1-91 (2009).
Jhunjhunwala, et al., "Controlled release formulations of IL-2, TGF-$^2$1 and rapamycin for the induction of regulatory T cells", J Cont Rel., 159(1):78-84 (2012).
Khalil, et al., "Angiotensin II type 1 receptor antagonist (losarian) down-regulates transforming growth factor-beta in experimental acute pyelonephritis", J Urology, 164(1):186-91 (2000).

(56) References Cited

OTHER PUBLICATIONS

Ma et al., "The comparison of different daidzein-PLGA nanoparticles in increasing its oral bioavailability", Int J Nanomed., 7:559-570 (2012).

Mura, et al., "Development of a new delivery system consisting in drug-in cyclodextrin-in PLGA nanoparticles", J Microencapsulation, 27(6):479-86 (2010).

Murphy, et al., "Targeted Nanogels: A Versatile Platform for Drug Delivery to Tumors", Mole Cancer Therapeutics, 10(6):972-82 (2011).

Park, et al., "Combination delivery TGF-$^2$ inhibitor and IL-2 nanoscale liposomal polymeric gels enhances tumor immunotherapy", Nat Mater., 11(20):895-905 (2012).

Steenblock, et al., "A Comprehensive Platform for Ex Vivo T-cell Expansion Based on Biodegradable Polymeric Artificial Antigen-presenting Cells", Mole Therapy, 16(4):765-72 (2008).

Wong, et al., "Simultaneous delivery of doxorubicin and GG918 (Elacridar) by new polymer-lipid hybrid nanoparticles (PLN) for enhanced treatment of multidrug-resistant breast cancer", J Cont Rel., 116:275-84 (2006).

Xiao, et al., "Recent advances in PEG-PLA block copolymer nanoparticles", Int J Nanomed., 5:1057-65 (2010).

Zhang, et al., "Self-assembled lipid-polymer hubrid nanoiparticles: A robust drug delivery platform", ACS Nano, 2(8):1696-1702 (2008).

\* cited by examiner

| nLG composition (per mg of nanoparticles) | | nLG formulation properties | |
|---|---|---|---|
| Lipids (PC:DSPE(PEG2000):Chol) 3:1:1 molar ratio | | ¹Yield | 80-90% |
| ¹PC | 40% ± 5% | ²Size | 120nm ± 20nm |
| ²DSPE (PEG) | 7.5% ± 2% | ³Polydispersity Index | 0.2 ± 0.05 |
| Cholesterol | 10% ± 2 | ⁴Encap.Efficiency(SB) | 36 ± 8% |
| ³CD | 11.3% ± 2 | ⁴Encap.Efficiency(IL-2) | 80 ± 10% |
| ⁴Polymer | 27.7% ± 3 | ⁵Loading (SB) | 40 ± 10 ug/mg |
| ⁵AEM | 3.8% ± 0.5 | ⁵Loading (IL-2) | 10 ± 2 ng/mg |

¹Phosphatidyl Choline
²1,2-distearoyl-sn-glycero-3-phosphoethanolamine-N-[amino(polyethylene glycol)-2000]
³Hydroxypropyl Cyclodextran
⁴acryl-PLA-PEG(4000)-PLA-acryl
⁵Aminoethyl methacrylate ¹mg nanoparticles/mg of lipids
²Dynamic Light scattering(diameter)
³Based on Cumulants analysis (an estimate of the width of the distribution)
⁴Measured loading/Maximum Loading
⁵Mass of drug in nLG/Mass of nLG

FIG. 1E

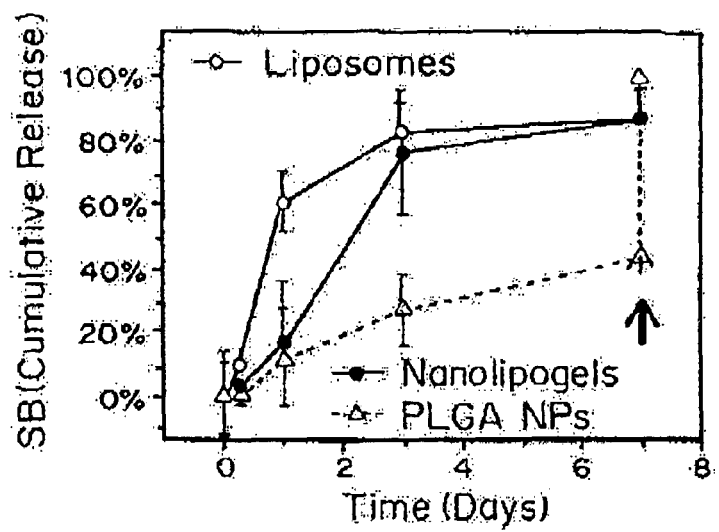
FIG. 2D
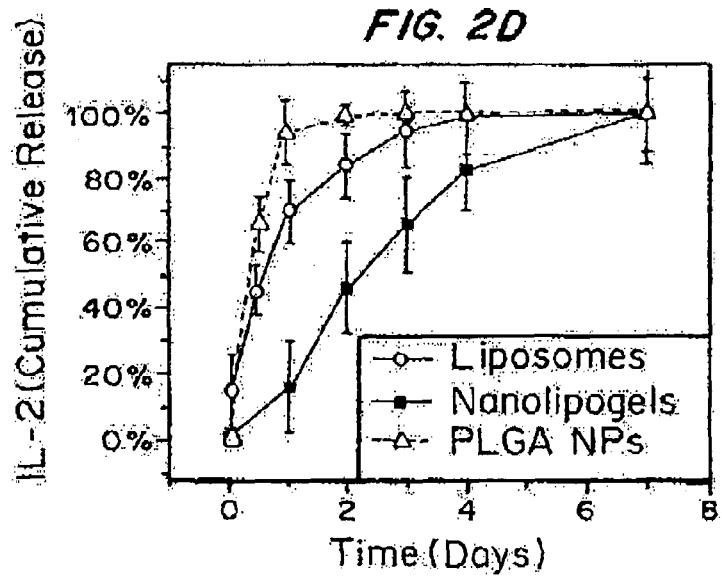
FIG. 2E
| | Size (nm) | Loading* | |
| --- | --- | --- | --- |
| | | IL-2 (ng/mg) | SB (ug/mg) |
| PLGA | 150±50 | 1±2 | 20±10 |
| nLG | 120±20 | 10±2 | 40±10 |
| Liposome | 100±20 | 35±15 | 3±2 |
*mass of drug in particle/particle mass
FIG. 2F

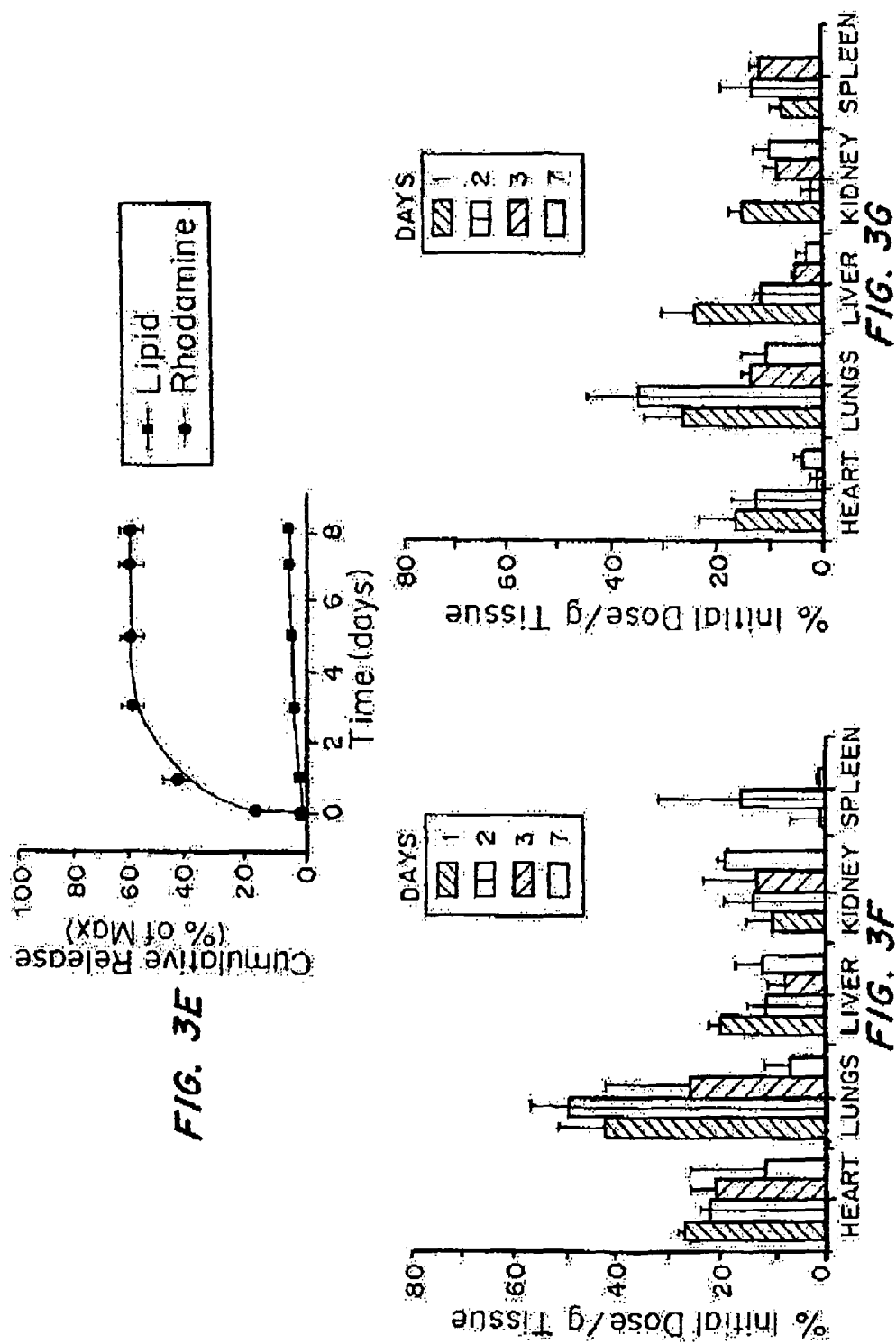

FIG. 6A

Paracrine Delivery of Immunosuppressives

- ● anti-CD4 ngel-rhodamine
- ▫ non-targeted ngel-rhodamine
- ▲ free rhodamine

- anti-CD4 ngel-rhodamine
- non-targeted ngel-rhodamine
- free rhodamine

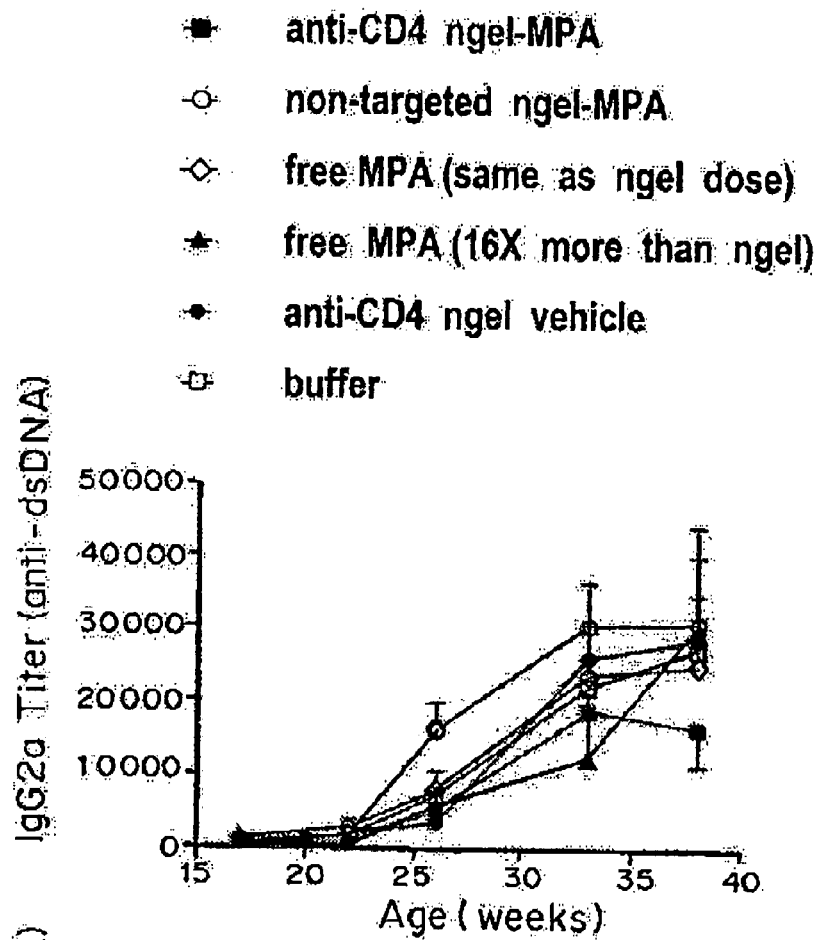
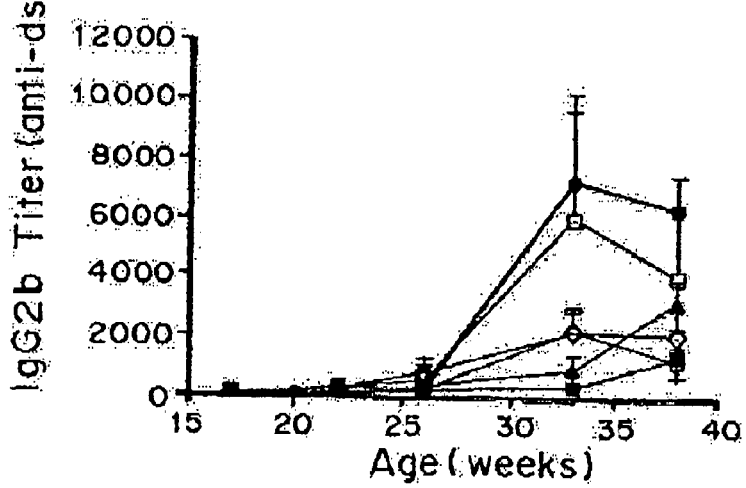
FIG. 14C
FIG. 14D

Treatment

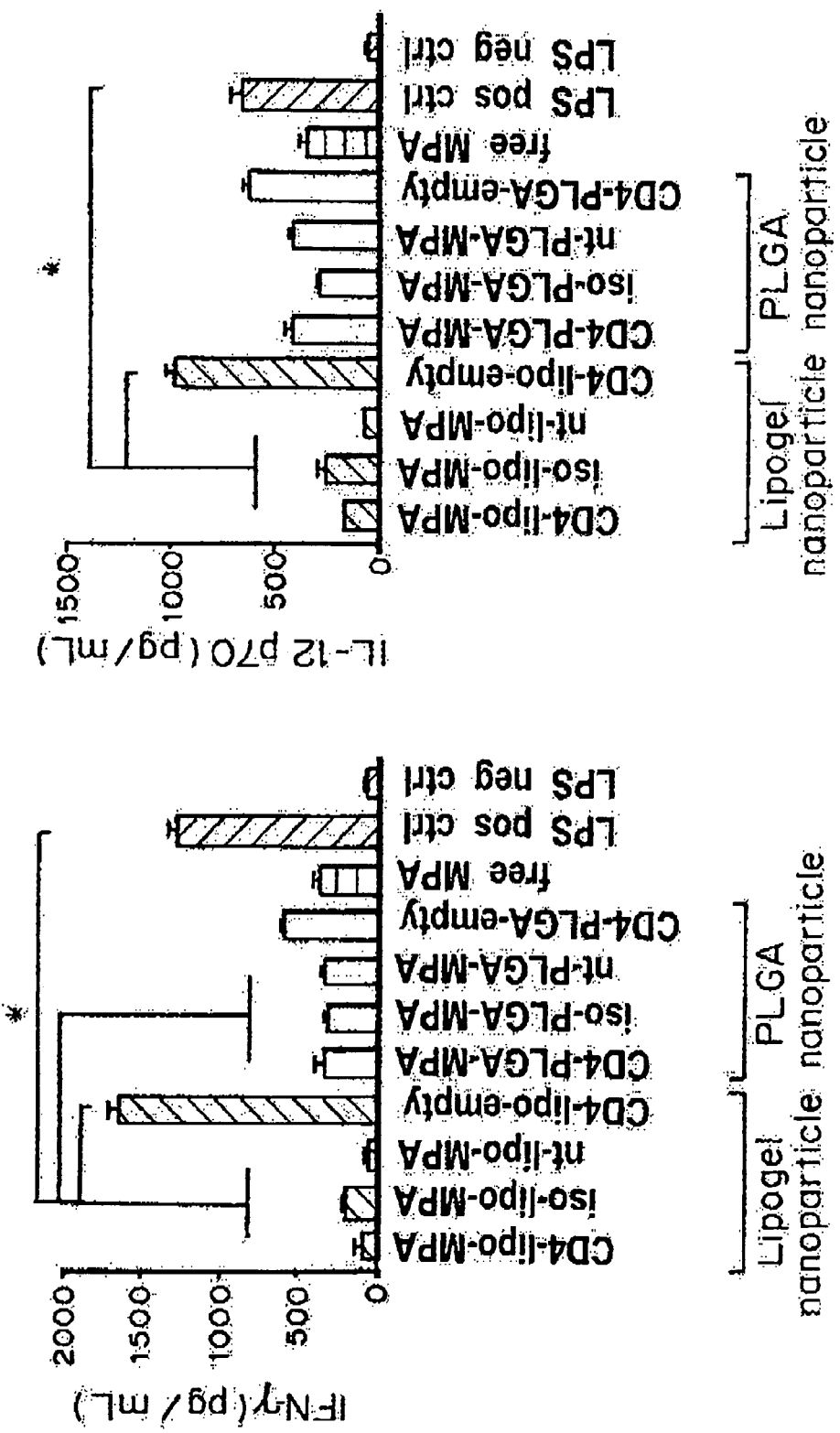

METHODS OF TREATING INFLAMMATORY AND AUTOIMMUNE DISEASES AND DISORDERS USING NANOLIPOGELS

CROSS REFERENCE TO RELATED APPLICATIONS

This application is a 371 application of International Application No. PCT/US2013/036494, filed Apr. 12, 2013, which claims the benefit of and priority to U.S. Provisional Application No. 61/623,486, filed Apr. 12, 2012, U.S. Provisional Application No. 61/747,624, filed Dec. 31, 2012, and U.S. Provisional Application No. 61/747,614, filed Dec. 31, 2012.

STATEMENT REGARDING FEDERALLY SPONSORED RESEARCH OR DEVELOPMENT

This invention was made with government support under Agreements R01-HL085416 and R01-EB008260 awarded by the National Institutes of Health, Public Health Grant Number HL-55397, and NIRT Grant Number CTS3090609326 awarded by the National Science Foundation. This invention was also made with government support under Agreement X45677 awarded by the Lupus Research Foundation, the Autoimmunity Center of Excellence Pilot Award (NIH U19) 2030977 and the National Institutes of Health. The government has certain rights in the invention.

FIELD OF THE INVENTION

The present invention is generally in the field of compositions and methods of sustained delivery of high and low molecular weight, or hydrophilic and hydrophobic molecules using core-lipid shell nanoparticulates for the treatment of inflammatory and autoimmune diseases and disorders.

BACKGROUND OF THE INVENTION

Autoimmune diseases are broadly characterized by the immunological loss of self-tolerance. In systemic lupus erythematosus (SLE), a canonical autoimmune disease, a traditional hallmark is the persistence of T and B cells that are aberrantly reactive to self-antigens such as nucleic acids and nuclear proteins; these T and B lymphocytes promote the production of pathogenic autoantibodies which deposit in tissues and prime inflammatory damage (Shlomchik, et al., *Nat Rev Immunol*, 1(2):147-53 (2001); Rahman, et al. *N Engl J Med*, 358(9):929-39 (2008)). The contribution of innate antigen presenting cells has recently been elucidated. Dendritic cells and macrophages have been shown to contribute to lupus pathology by producing proinflammatory cytokines (Blanco, et al., *Science*, 294(5546): 1540-3 (2001); Triantafyllopoulou, et al., *Proc Natl Acad Sci USA*, 107(7):3012-7 (2010)) and promoting expansion of autoreactive T and B cells (Teichmann, et al., *Immunity*, 33(6): 967-78 (2010)).

Current methods used to treat autoimmune diseases have traditionally relied on the chronic administration of hydrophobic drugs (Monneaux, et al., *Arthritis Res Ther*, 11(3): 234 (2009)) or, more recently, biological agents (proteins and neutralizing antibodies) (Ronnblom, et al., *Nat Rev Rheumatol*, 6(6): 339-47 (2010); Navarra, et al., *Lancet*, 377(9767):721-31 (2011); Sfikakis, et al., *Curr Opin Rheumatol*, 17(5): 550-7 (2005)) which inhibit the proliferation or activation of lymphocytes. The conventional administration of pan-immunosuppressive small molecule therapies, which are often achieved with hydrophobic drugs such as cyclophosphamide, azathioprine, or mycophenolate mofetil (MMF), provides therapeutic immunosuppression by blunt reduction of total immune cell numbers. This pan-suppressive effect can lead to organ toxicity or lymphopenias and anemia, and render human patients more susceptible to opportunistic infections (Lee, et al., *Lupus*, 19(6):703-10 (2010); Moroni, et al., *Clin J Am Soc Nephrol*, 1(5):925-32 (2006)). Biological agents which deplete B cells or block T cell costimulatory signals may provide a more refined, cell-specific approach to immunosuppression, but as a stand-alone monotherapy they may be ineffective in attenuating autoimmunity from innate antigen presenting cells.

An ideal therapeutic strategy could combine the pan-suppressive effects of small molecule therapies with targeting specificity to the immune cells implicated in lupus pathogenesis. Nanoparticles have been actively explored for therapeutic use in other diseases such as cancer (Blanco, et al., *Cancer Sci*, 102(7):1247-52 (2011)) and infectious pathogens (Look, et al., *Adv Drug Deliv Rev*, 62(4-5):378-93 (2010)). These nanoparticle drug delivery systems can be loaded with therapeutic compounds with several different methods, and their use in vivo can improve the bioavailability of therapeutic compounds and to specifically target tissues or cells of therapeutic interest (Fahmy, et al., *Materials Today*, 8(8):18-26 (2005)). Few therapeutic strategies have extensively explored the efficacy of nanoparticles as a drug delivery vehicle for achieving therapeutic immunosuppression in lupus. To date, published reports regarding nanoparticles and lupus are limited to studies of nanoparticles that are designed to traffic to relevant sites of lupus pathology, namely the kidney (Scindia, et al., *Arthritis Rheum*, 58(12):3884-91 (2008); Serkova, et al., *Radiology*, 255(2):517-26 (2010)), but no studies have demonstrated actual therapeutic drug delivery with these nanoparticle systems. Thus, little is known about how nanoparticles may interact with different immune cell sets in lupus, and if these interactions could be exploited to improve lupus immunotherapies.

Several types of nanoparticle systems, liposomes and synthetic polymeric matrix formulations are commonly used. Several nanoparticle platforms are potential candidates for this purpose. Generally these platforms can be classified as either vesicular in nature (such as liposomes) or composed of solid biodegradable matrices (such as polyester-based nanoparticles). Liposomes are easily modified for encapsulation of small hydrophilic molecules, and even proteins, but the stability of these formulations and the release profiles of encapsulated agents can be poor (Maurer, et al., *Expert Opinion on Biological Therapy*, 1(6):923-947 (2001)). Biodegradable solid particles such as those fabricated from poly(lactic-co-glycolic acid) (PLGA), are highly stable and have controllable release characteristics, but pose complications via induction of maturation of dendritic cells (Yoshida, et al., *J Biomed Mater Res A*, 80(1):7-12 (2007)) and degradation into acidic byproducts that may promote inflammation (Shive, et al., *Adv Drug Deliv Rev*, 28(1):5-24 (1997)).

No effective treatment for lupus other than generalized immunosuppression has been found.

It is therefore an object of the present invention to provide compositions for treating lupus with greater selectivity and efficacy.

It is also an object of the present invention to provide a method for treatment of lupus with greater selectivity and efficacy.

SUMMARY OF THE INVENTION

Compositions and methods for treating or ameliorating the symptoms of inflammatory or autoimmune disease or disorder are described herein. The compositions contain a nanolipogel for sustained delivery of an effective amount of one or more active agents of choice, preferably a drug for treating or ameliorating one or more symptoms of an inflammatory or autoimmune disease or disorder. The nanolipogel includes a lipid bilayer surrounding a hydrogel core, which may optionally include a host molecule, for example, an absorbent such as a cyclodextrin or ion-exchange resin. In preferred embodiments, at least one of active agents is an immunosuppressant. In some embodiments, the nanolipogel includes a targeting moiety that increases specificity of the particle for activated T cells or antigen presenting cells.

Also provided are methods of incorporating agents into the nanolipogels described herein. The nanolipogel is loaded with one or more drugs such that controlled release of the agent(s) is subsequently achieved. In some embodiments, the nanolipogel is loaded with one or more first agent(s) during formation and one or more second agent(s) following formation by the process of rehydration of the nanolipogel in the presence of the second agents. The agent(s) can be dispersed within the hydrogel matrix, associated with one or more host molecules, dispersed within the liposomal shell, covalently attached to the liposomal shell, and combinations thereof. Drugs can be selectively incorporated at each of these locales within the nanolipogel.

Also provided herein is a method of treating or ameliorating the symptoms of an inflammatory or autoimmune disease or disorder using the compositions described herein. In a preferred embodiment, the treatment involves suppression of both T and B cell effector types. The methods can include reducing T cell proliferation, activation, response, or function, or increasing the tolerance of antigen-presenting cells, or combinations thereof. For example, the formulations can target and inactivate these immune cells with immunosuppressive drugs at a lower dose and reduced toxicity compared to conventional drug methods. The technology is generally applicable to a number of inflammatory and autoimmune disease states, for treatment and/or suppression of autoimmune disease, suppression of allograft rejection and treatment of allergic diseases.

BRIEF DESCRIPTION OF THE DRAWINGS

In FIG. 1A, methacrylate-functionalized cyclodextrin (CD) was used to solubilize a bioactive such as the TGF-β inhibitor (SB505124). In FIG. 1B, nanolipogels were formulated from lyophilized liposomes loaded with biodegradable crosslinking polymer, acrylated-drug (CD-SB505) complex, and a second drug such as the peptide IL-2 cytokine. This core-shell structure facilitated entrapment of drug loaded CD and the IL-2 in an interior biodegradable polymer matrix with a PEGylated liposomal exterior. Succinylated β-cyclodextrin (CTD, Inc.) was functionalized with 2-aminoethyl methacrylate (Sigma) by stirring a 1:3 molar ratio of the compounds in 1×PBS for 1 hour at room temperature. The $^1$H NMR spectra (500 MHz, D$_2$O) of SB505124, randomly succinylated β-CD, and the inclusion complex of SB505124 with randomly succinylated β-CD was determined. The differences observed in the aromatic proton region of SB505124 demonstrate formation of the inclusion complex. The $^1$H NMR spectra (500 MHz, D$_2$O) of rhodamine B, randomly succinylated β-CD, and the inclusion complex of rhodamine B with randomly succinylated β-CD showed the differences observed in the aromatic proton region of rhodamine B demonstrate formation of the inclusion complex.

FIGS. 1C-1G show nanolipogel characterization. Nanolipogel size was determined by dynamic light scattering on a ZetaPALS instrument (Brookhaven Instruments) in PBS at room temperature. FIG. 1C shows that encapsulation of SB or SB+IL-2 had no significant effect on particle mean diameter or polydispersity. Mean diameter and polydispersity index are representative of 2 lots of each nanolipogel type (n=10 measurements per sample). The zeta potential of PC/cholesterol liposomes, PC/cholesterol/PE-PEG-NH$_2$ liposomes, and nanolipogels were evaluated in 0.1×PBS using a Malvern nanosizer. FIG. 1D shows that the zeta potential of liposomes and nanolipogels incorporating amine-terminated PE-PEG was found to be close to neutral. FIG. 1E shows the composition and formulation properties of the nanolipogel formulation. FIG. 1F shows the polymer structure verified by $^1$H NMR. Cryo-TEM of nanolipogels demonstrating the formation of spherical liposomal structures. For TEM analysis, nanolipogel samples were stained with osmium tetroxide and then imaged on an FEI Tenai Biotwin microscope. Lipid-specific osmium tetroxide staining of cryosectioned samples had a localized staining pattern confined to the exterior membrane of the particle. FIG. 1G shows that the photopolymerized polymer/CD forms nanoparticulate hydrogel structures that are detectable by light scattering even after disruption of the liposomal exterior by detergent.

FIGS. 2A-2E are comparative release profiles from nLG, lipsomes and solid polymer nanoparticles (PLGA). Cumulative CD- or methacrylate functionalized-CD (f-CD)-solubilized SB released from nLGs normalized by initial carrier mass demonstrated that polymerization of nanolipogels improved the sustained nature of SB release (FIG. 2A). Hydroxypropyl β-CD was used for SB complexation with the unfunctionalized CD. Cumulative IL-2 released determined by ELISA (immunoactive) and by a bioactivity study (bioactive) from nLGs normalized by initial nanolipogel mass demonstrated that bioactivity of IL-2 was unaffected by encapsulation (FIG. 2B). Release of SB and IL-2 was not affected by incubation of 10 mg nLG in 1 ml full serum (FIG. 2C). Comparative cumulative release of SB from liposomes, nanolipogels, and degradable polymeric (poly lactide-co-glycolide) nanoparticles (PLGA NPs) demonstrated that incorporation of photo-cured polymer in the nanolipogel vehicle enabled better sustained release and more complete release of cyclodextrin-solubilized SB (FIG. 2D). PLGA NPs (mean diameter=150±50 nm) were prepared by using a modified water/oil/water double emulsion technique. Liposomes were prepared in an identical manner as the nLG without the polymer core. Liposomes were loaded with IL-2 and SB similar to nanolipogels. The diminished percent of encapsulated SB released from PLGA NPs is attributed to the interaction of the relatively hydrophobic polymer with SB. All particulate formulations were dissolved in 0.1N NaOH+1% SDS to determine 100% release at 7 days (arrow) (FIG. 2D). Comparative cumulative release of IL-2 from liposomes, nanolipogels, and PLGA NPs demonstrated that encapsulation of IL-2 in nanolipogels enabled better sustained release of cytokine. Cumulative release is presented as % of total IL-2 released through 7 days. (FIG. 2E) Data in all graphs represent mean of triplicate samples ±1 standard deviation. FIG. 2F compares the sizes and loading of IL-2 and SB in PLGA, nanolipogels and liposomes.

FIGS. 3A-3G are graphs showing controlled release, clearance, and biodistribution. The distribution of both nanolipogel carrier and encapsulated drug payload was investigated using dual-labeled NLG; fluorescein-labeled phosphoethanolamine was incorporated into the lipid component of rhodamine-loaded nanolipogels. Spectrofluorimetric analysis at 540/625 nm and 490/517 nm show dose-dependent fluorescence with no spectral overlap. FIG. 3A is a graph of cumulative IL-2 (ng/mg nLG) and drug (μg SB/mg nLG) released from co-loaded nLGs normalized by carrier mass. Error bars in all plots represent ±1 standard deviation. All experiments were repeated at least twice with similar results. FIG. 3B is a graph showing clearance (percent of initial dose) of drug dose over time in days: Encapsulation in nanolipogels significantly increased the remaining percentage of initial dose in the blood at 1 and 24 hours post-injection (two population t test, $p<0.01$ ###). FIG. 3C is a graph of whole body distribution. Mice received a single dose of rhodamine-loaded nanolipogel or soluble rhodamine (in saline) via intravenous tail vein injection. Animals were sacrificed at 1, 24, 48, and 72 hours post-injection for extraction and quantification of fluorescence; whole body biodistribution was determined with rhodamine labeling. Significantly higher (two population t test, $p<0.01$) amounts of rhodamine were detected in the major organs of nanolipogel-treated animals compared to animals injected with free dye. FIG. 3D is a graph of time dependent accumulation n in subcutaneous tumor: Cumulative rhodamine tumor penetration (circles) after B16 peritumoral injection in B6 mice. Peritumoral tissue was collected to quantify the remaining dose of nLG surrounding the tumor (squares). Controlled release demonstrates release of rhodamine, but not lipid (FIG. 3E). Mice bearing subcutaneous B16 tumors received a single IV (tail vein) injection of dual-labeled NLG. Animals were sacrificed at 1, 2, 3, and 7 days post injection and tissues collected for homogenization, extraction, and quantification of rhodamine and fluorescein-PE. Analysis of serum showing prolonged circulation of both encapsulant and delivery vehicle. Similar patterns of biodistribution were observed between lipid (FIG. 3F) and drug payload (FIG. 3G), with highest accumulations of drug occurring in the lungs and liver.

mock: nonsense siRNA
LFA: control siRNA against LFA
G3: unmodified generation 3 PAMAM dendrimer
G3 5x: G3 dendrimer with 1 cyclodextrin conjugated (G3-1CD)
G3 5xd: G3 with 2 CD conjugated (G3-2CD)
G3 10x: G3 with 3 CD conjugated (G3-3CD)
G3 20x: G3 with 3.4 CD conjugated (G3-3.4CD)
G4: G4 dendrimer with no modifications (G4)
G4 5x: G4 dendrimer with 1 CD conjugated (G4-1CD)
G4 5xd: G4 dendrimer with 1.3 CD conjugated (G4-1.3CD)
G4 10x: G4-3CD
G5: generation 5 (G5) dendrimer with no modifications
G5 5x: G5-1CD
G5 10x: G5-3CD
G5 10x 0.5 mg: G5-3CD, 500 ug used instead of 200 ug in other treatments
G5 10x D: G5-2.5CD
G5 20x: G5-4CD

FIG. 6A is a schematic of paracrine delivery of immunosuppressives. The nanolipogels release MPA The nanoparticles may be loaded with CTLA4Ig or other biologic, in addition to MPA or other drug, and release them.

FIGS. 14A-14E are graphs of titer (pan anti-dsDNA) (14A), IgG1 titer (anti-dsDNA) (14B), IgG2a (anti-dsDNA) (14C), IgG2b Titer (anti-dsDNA) (14D), and IgG3 titer (anti-dsDNA) (14E) over time (age in weeks).

FIGS. 20D, 20E, and 20F are bar graphs showing the IFN-γ production (pg/ml) (20E), IL-12p70 production (20F), and TFN-α (pg/ml) (20G) by dendritic cells treated with free MPA, or with MPA-loaded or empty nanolipogels (lipo) or PLGA nanoparticles, with no targeting (nt), anti-CD4 targeting, or isotype control targeting following LPS challenge. LPS positive and negative controls are also included. p<0.05 or less by 1-way ANOVA comparison.

DETAILED DESCRIPTION OF THE INVENTION

I. Definitions

Figure 1A:
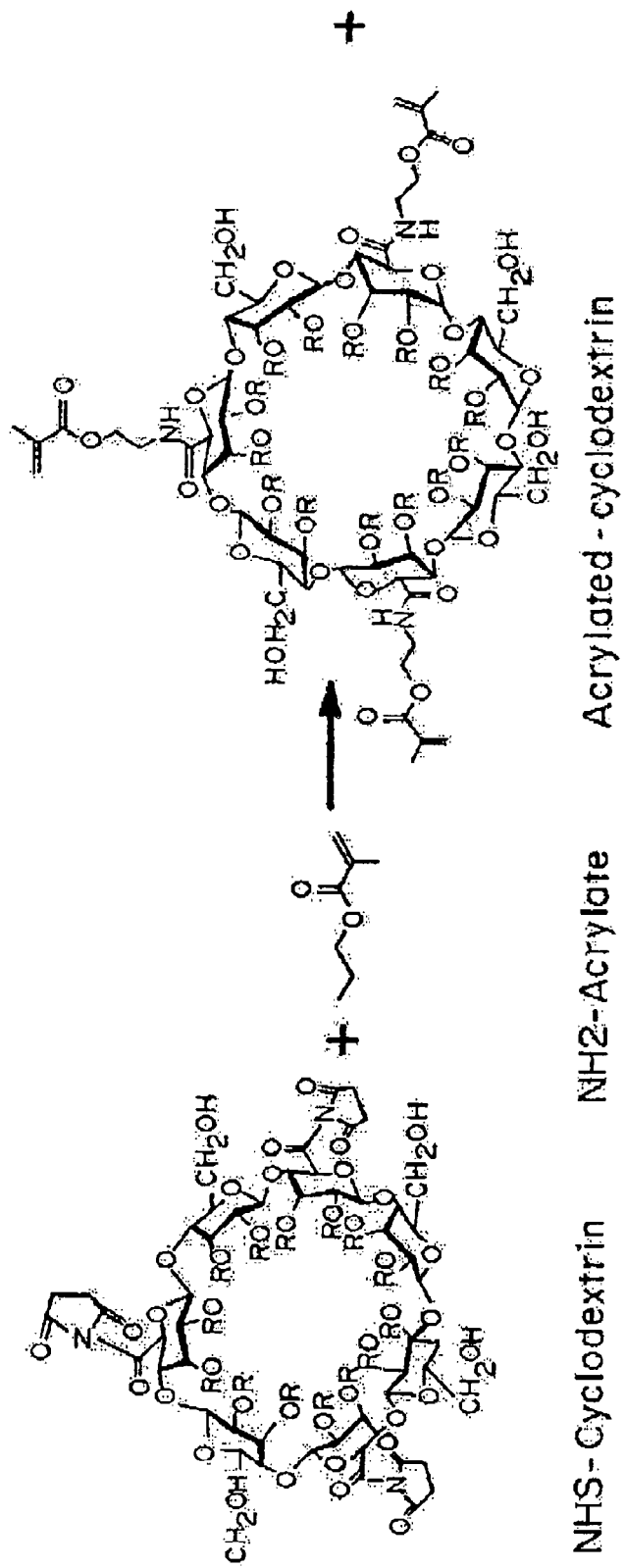
FIGS. 1A-1B are schematics of the fabrication of the nanolipogel particles (nLG).
Figure 1A:
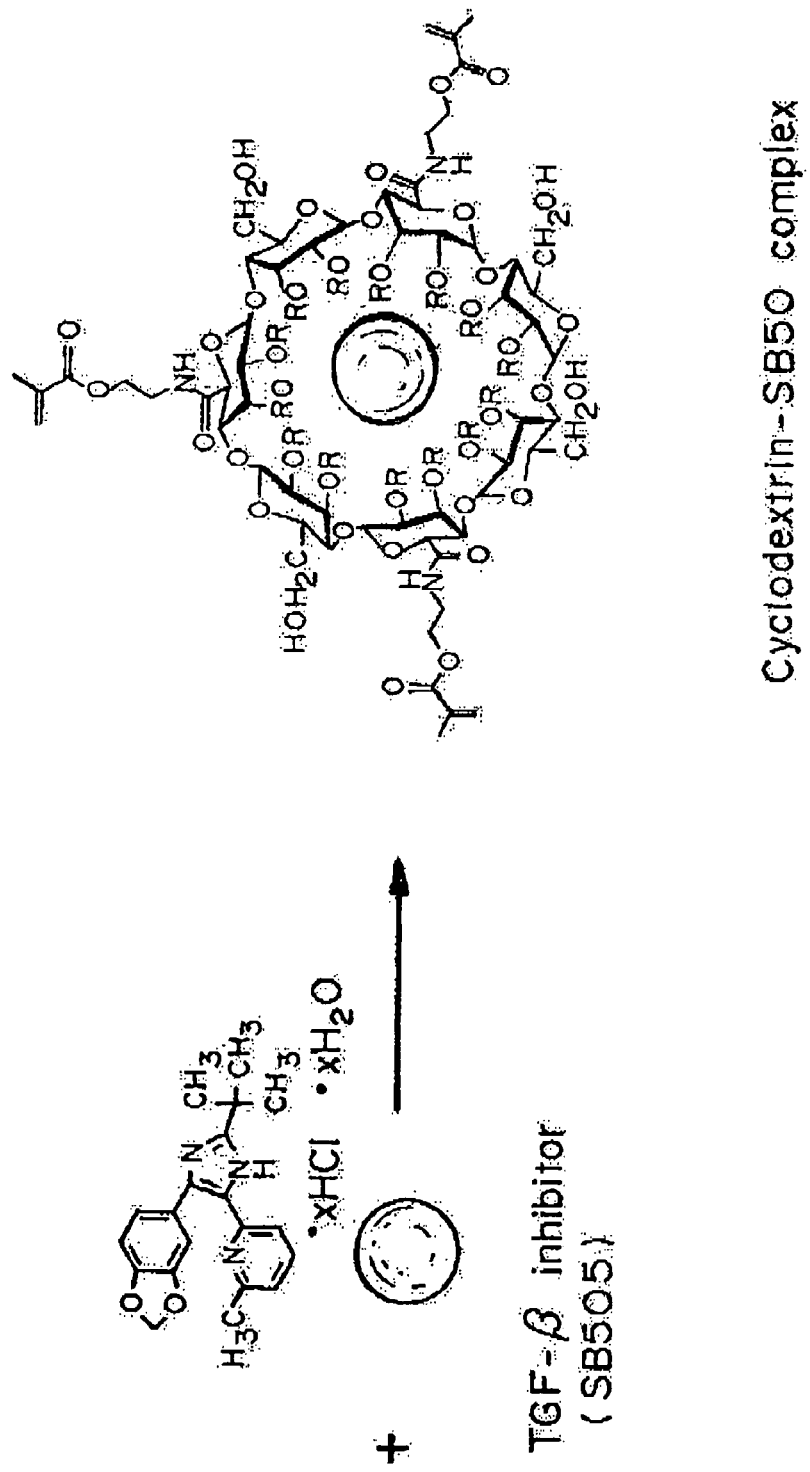

"Nanolipogel," as used herein, refers to a core-shell nanoparticle having a polymer matrix core, which can contain a host molecule, within a liposomal shell, which may be unilamellar or bilamellar, optionally crosslinked.

"Host molecule," as used herein, refers to a molecule or material which reversibly associates with an active agent to form a complex. In particular embodiments, the host is a molecule that forms an inclusion complex with an active agent. Inclusion complexes are formed when an active agent (i.e., the guest) or portion of an active agent inserts into a cavity of another molecule, group of molecules, or material (i.e., the host). The host may be a small molecule, an oligomer, a polymer, or combinations thereof. Exemplary hosts include polysaccharides such as amyloses, cyclodextrins, and other cyclic or helical compounds containing a plurality of aldose rings, for example, compounds formed through 1,4 and 1,6 bonding of monosaccharides (such as glucose, fructose, and galactose) and disaccharides (such as sucrose, maltose, and lactose). Other exemplary host compounds include cryptands, cryptophanes, cavitands, crown ethers, dendrimers, ion-exchange resins, calixarenes, valinomycins, nigericins, catenanes, polycatenanes, carcerands, cucurbiturils, and spherands.

"Small molecule," as used herein, refers to molecules with a molecular weight of less than about 2000 g/mol, more preferably less than about 1500 g/mol, most preferably less than about 1200 g/mol.

"Hydrogel," as used herein, refers to a water-swellable polymeric matrix formed from a three-dimensional network of macromolecules held together by covalent or non-covalent crosslinks, that can absorb a substantial amount of water (by weight) to form a gel.

"Hydrodynamic radius" of a particle, as used herein, is the radius of a hard and perfectly spherical object of the same mass and having the same rate of diffusion as the particle. This may also be referred to, interchangeably, as the Stokes radius or as the Stokes-Einstein radius. Diameter is typically two times the radius.

"Nanoparticle", as used herein, generally refers to a particle having a diameter from about 10 nm up to, but not including, about 1 micron, preferably from 100 nm to about 1 micron. The particles can have any shape. Nanoparticles having a spherical shape are generally referred to as "nanospheres".

"Molecular weight" as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size" as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% of the distribution lies within 15% of the median particle size, more preferably within 10% of the median particle size, most preferably within 5% of the median particle size.

"Active Agent", as used herein, refers to a physiologically or pharmacologically active substance that acts locally and/ or systemically in the body. An active agent is a substance that is administered to a patient for the treatment (e.g., therapeutic agent), prevention (e.g., prophylactic agent), or diagnosis (e.g., diagnostic agent) of a disease or disorder.

The term "immune cell" refers to cells of the innate and acquired immune system including neutrophils, eosinophils, basophils, monocytes, macrophages, dendritic cells, lymphocytes including B cells, T cells, and natural killer cells.

II. Nanolipogels

Nanolipogels are core-shell nanoparticulates that combine the advantages of both liposomes and polymer-based particles for sustained delivery of active agents. As discussed in more detail below, typically, the outer shell protects cargo, provides biocompatibility and a surface for functionalization with targeting molecule(s). The outer shell encapsulates components such that they are not exposed until desired, for example, in response to environmental conditions or stimuli, creatings monodisperse, reproducible particle populations, and mediating internalization into desired cell types. The inner core, which can be a dendrimer or other polymer, has separate and additive functionalities to outer shell. For example, the inner shell allows for secondary deposition of drug, vaccine, or imaging agent; increases loading of components with different physiochemical properties into the particle; allows for tunable release of contents from particles; increases cytosolic availability of DNA/RNA, drug, and/or protein by disrupting endosomes, all leading to enhanced drug effects, antigen presentation, and transfection/silencing.

Nanolipogels have a polymer matrix core containing one or more host molecules. The polymeric matrix is preferably a hydrogel, such as a crosslinked block copolymer containing one or more poly(alkylene oxide) segments, such as polyethylene glycol, and one or more aliphatic polyester segments, such as polylactic acid. One or more host molecules, such as a cyclodextrin, dendrimer, or ion exchange resin, is dispersed within or covalently bound to the polymeric matrix. The hydrogel core is surrounded by a liposomal shell.

Nanolipogels can be constructed to incorporate a variety of active agents that can subsequently be released in a controlled fashion. Active agents can be dispersed within the hydrogel matrix, associated with one or more host molecules, dispersed within the liposomal shell, covalently attached to the liposomal shell, and combinations thereof. Active agents can be selectively incorporated at each of these locales within the nanolipogel. Furthermore, the release rate of active agents from each of these locales can be independently tuned. Because each of these locales possesses distinct properties, including size and hydrophobicity/hydrophilicity, the chemical entities independently incorporated at each of these locales can differ dramatically with respect to size and composition. For example, nanolipogels can be loaded with one or more proteins dispersed within the polymeric matrix as well as small molecule hydrophobic drugs associated with host molecules.

In this way, nanolipogels can provide simultaneous sustained release of agents that differ widely in chemical composition and molecular weight. In a non-limiting example, nanolipogels may be loaded with both a hydrophobic, small molecule antigen associated with a host molecule and an immunoadjuvant, such as an immunostimulatory protein, dispersed within the polymeric matrix. These nanolipogels can provide sustained release of the antigen together with the adjuvant, to optimize an immune response.

In a particular example, simultaneous sustained delivery by nanolipogels of an immunostimulatory protein, Interleukin-2 (IL-2), as well as a low molecular weight organic molecule, 2-(5-benzo[1,3]dioxol-5-yl-2-tert-butyl-3H-imidazol-4-yl)-6-methylpyridine hydrochloride, an inhibitor of transforming growth factor-β (TGF-β), was achieved. This construct leads to an anti-tumor response in a murine system that is far superior to that achievable with the administration in solution of either agent alone or a combination of the two. Additionally, nanolipogels can favorably modulate biodistribution of one or more active agents encapsulated therein.

Nanolipogels are typically spherical in shape, with average particle sizes ranging between about 50 nm and about 1000 nm, more preferably between about 75 nm and about 300 nm, most preferably between about 90 nm and about 200 nm. In certain embodiments, the nanolipogels possess an average particle size between about 100 nm and about 140 nm. Particles may be non-spherical.

Depending upon the nature of the lipids present in the liposomal shell of the nanolipogels, the nanolipogels having a positive, negative, or near neutral surface charge may be prepared. In certain embodiments, the nanolipogels possess a near neutral surface charge. In certain embodiments, the nanolipogels possess a ζ-potential of between about 10 mV and about −10 mV, more preferably between about 5 mV and about −5 mV, more preferably between about 3 mV and about −3 mV, most preferably between about 2 mV and about −2 mV.

A. Core

The nanolipogel core is formed from a polymeric matrix and one or more host molecules. The nanolipogel core may further include one or more active agents. The active agents may be complexed to the host molecules, dispersed with polymeric matrix, or combinations thereof.

1. Polymeric Matrix

The polymeric matrix of the nanolipogels may be formed from one or more polymers or copolymers. By varying the composition and morphology of the polymeric matrix, one can achieve a variety of controlled release characteristics, permitting the delivery of moderate constant doses of one or more active agents over prolonged periods of time.

The polymeric matrix may be formed from non-biodegradable or biodegradable polymers; however, preferably, the polymeric matrix is biodegradable. The polymeric matrix can be selected to degrade over a time period from ranging from one day to one year, more preferably from seven days to 26 weeks, more preferably from seven days to 20 weeks, most preferably from seven days to 16 weeks.

In general, synthetic polymers are preferred, although natural polymers may be used. Representative polymers include poly(lactic acid), poly(glycolic acid), poly(lactic acid-co-glycolic acids), polyhydroxyalkanoates such as poly3-hydroxybutyrate or poly4-hydroxybutyrate; polycaprolactones; poly(orthoesters); polyanhydrides; poly (phosphazenes); poly(lactide-co-caprolactones); poly(glycolide-co-caprolactones); polycarbonates such as tyrosine polycarbonates; polyamides (including synthetic and natural polyamides), polypeptides, and poly(amino acids); polyesteramides; other biocompatible polyesters; poly(dioxanones); poly(alkylene alkylates); hydrophilic polyethers; polyurethanes; polyetheresters; polyacetals; polycyanoacrylates; polysiloxanes; poly(oxyethylene)/poly(oxypropylene) copolymers; polyketals; polyphosphates; polyhydroxyvalerates; polyalkylene oxalates; polyalkylene succinates; poly (maleic acids), polyvinyl alcohols, polyvinylpyrrolidone; poly(alkylene oxides) such as polyethylene glycol (PEG); derivatized celluloses such as alkyl celluloses (e.g., methyl cellulose), hydroxyalkyl celluloses (e.g., hydroxypropyl cellulose), cellulose ethers, cellulose esters, nitrocelluloses, polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate) (jointly referred to herein as "polyacrylic acids"), as well as derivatives, copolymers, and blends thereof.

As used herein, "derivatives" include polymers having substitutions, additions of chemical groups and other modifications to the polymeric backbones described above routinely made by those skilled in the art. Natural polymers, including proteins such as albumin, collagen, gelatin, prolamines, such as zein, and polysaccharides such as alginate and pectin, may also be incorporated into the polymeric matrix. While a variety of polymers may be used to form the polymeric matrix, generally, the resulting polymeric matrix will be a hydrogel. In certain cases, when the polymeric matrix contains a natural polymer, the natural polymer is a biopolymer which degrades by hydrolysis, such as a polyhydroxyalkanoate.

In preferred embodiments, the polymeric matrix contains one or more crosslinkable polymers. Preferably, the crosslinkable polymers contain one or more photo-polymerizable groups, allowing for the crosslinking of the polymeric matrix following nanolipogel formation. Examples of suitable photo-polymerizable groups include vinyl groups, acrylate groups, methacrylate groups, and acrylamide groups. Photo-polymerizable groups, when present, may be incorporated within the backbone of the crosslinkable polymers, within one or more of the sidechains of the crosslinkable polymers, at one or more of the ends of the crosslinkable polymers, or combinations thereof.

The polymeric matrix may be formed from polymers having a variety of molecular weights, so as to form nanolipogels having properties, including drug release rates, optimal for specific applications. Generally, the polymers which make up the polymeric matrix possess average molecular weights of about 500 Da and 50 kDa. In cases where the polymeric matrix is formed from non-crosslinkable polymers, the polymers typically possess average molecular weights ranging between about 1 kDa and about 50 kDa, more preferably between about 1 kDa and about 70 kDa, most preferably between about 5 kDa and about 50 kDa. In cases where the polymeric matrix is formed from crosslinkable polymers, the polymers typically possess lower average molecular weights ranging between about 500 Da and about 25 kDa, more preferably between about 1 kDa and about 10 kDa, most preferably between about 3 kDa and about 6 kDa. In particular embodiments the polymeric matrix is formed from a crosslinkable polymer having an average molecular weight of about 5 kDa.

In some embodiments, the polymeric matrix is formed from a poly(alkylene oxide) polymer or a block copolymer containing one or more poly(alkylene oxide) segments. The poly(alkylene oxide) polymer or poly(alkylene oxide) polymer segments may contain between 8 and 500 repeat units, more preferably between 40 and 300 repeat units, most preferably between 50 and 150 repeat units. Suitable poly (alkylene oxides) include polyethylene glycol (also referred to as polyethylene oxide or PEG), polypropylene 1,2-glycol, poly(propylene oxide), polypropylene 1,3-glycol, and copolymers thereof.

In some embodiments, the polymeric matrix is formed from an aliphatic polyester or a block copolymer containing one or more aliphatic polyester segments. Preferably the polyester or polyester segments are poly(lactic acid) (PLA), poly(glycolic acid) PGA, or poly(lactide-co-glycolide) (PLGA).

In preferred embodiments, the polymeric matrix is formed from a block copolymer containing one or more poly (alkylene oxide) segments, one or more aliphatic polyester segments, and optionally one or more photo-polymerizable groups. In these cases, the one or more poly(alkylene oxide) segments imbue the polymer with the necessary hydrophilicity, such that the resultant polymer matrix forms a suitable hydrogel, while the polyester segments provide a polymeric matrix with tunable hydrophobicity/hydrophilicity and/or the desired in vivo degradation characteristics.

The degradation rate of the polyester segments, and often the corresponding drug release rate, can be varied from days (in the case of pure PGA) to months (in the case of pure PLA), and may be readily manipulated by varying the ratio of PLA to PGA in the polyester segments. In addition, the poly(alkylene oxides), such as PEG, and aliphatic polyesters, such as PGA, PLA, and PLGA have been established as safe for use in humans; these materials have been used in human clinical applications, including drug delivery system, for more than 30 years.

In certain embodiments, the polymeric matrix is formed from a tri-block copolymer containing a central poly(alkylene oxide) segment, adjoining aliphatic polyester segments attached to either end of the central poly(alkylene oxide) segment, and one or more photo-polymerizable groups. Preferably, the central poly(alkylene oxide) segment is PEG, and aliphatic polyesters segments are PGA, PLA, or PLGA.

Generally, the average molecular weight of the central poly(alkylene oxide) segment is greater than the average molecular weight of the adjoining polyester segments. In certain embodiments, the average molecular weight of the central poly(alkylene oxide) segment is at least three times greater than the average molecular weight of one of the adjoining polyester segments, more preferably at least five times greater than the average molecular weight of one of the adjoining polyester segments, most preferably at least ten times greater than the average molecular weight of one of the adjoining polyester segments.

In some cases, the central poly(alkylene oxide) segment possesses an average molecular weight ranging between about 500 Da and about 10,000 Da, more preferably between about 1,000 Da and about 7,000 Da, most preferably between about 2,500 Da and about 5,000 Da. In particular embodiments, average molecular weight of the central poly(alkylene oxide) segment is about 4,000 Da. Typically, each adjoining polyester segment possesses an average molecular weight ranging between about 100 Da and about 5,000 Da, more preferably between about 100 Da and about 1,000 Da, most preferably between about 100 Da and about 500 Da.

In a preferred embodiment, the polymeric matrix is formed from the tri-block copolymer shown below

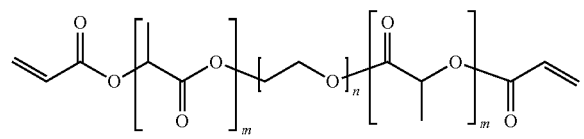

where m and n are, independently for each occurrence, integers between 1 and 500, more preferably between 10 and 150.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the microparticles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of preferred non-biodegradable polymers include ethylene vinyl acetate, poly(meth)acrylic acid, polyamides, copolymers and mixtures thereof.

The matrix can also be made of gel-type polymers, such as alginate, produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for twenty to thirty minutes in order to allow sufficient time for gelation to occur. Microparticle particle size is controlled by using various size extruders or varying either the nitrogen gas or polymer solution flow rates. Chitosan microparticles can be prepared by dissolving the polymer in acidic solution and crosslinking it with tripolyphosphate. Carboxymethyl cellulose (CMC) microparticles can be prepared by dissolving the polymer in acid solution and precipitating the microparticle with lead ions. In the case of negatively charged polymers (e.g., alginate, CMC), positively charged ligands (e.g., polylysine, polyethyleneimine) of different molecular weights can be ionically attached.

Perhaps the most widely used are the aliphatic polyesters, specifically the hydrophobic poly (lactic acid) (PLA), more hydrophilic poly (glycolic acid) PGA and their copolymers, poly (lactide-co-glycolide) (PLGA). The degradation rate of these polymers, and often the corresponding drug release rate, can vary from days (PGA) to months (PLA) and is easily manipulated by varying the ratio of PLA to PGA. Second, the physiologic compatibility of PLGA and its hompolymers PGA and PLA have been established for safe use in humans; these materials have a history of over 30 years in various human clinical applications including drug delivery systems. PLGA nanoparticles can be formulated in a variety of ways that improve drug pharmacokinetics and biodistribution to target tissue by either passive or active targeting. The microparticles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. Specifically the hydrophobic poly (lactic acid) (PLA), more hydrophilic poly (glycolic acid) PGA and their copolymers, poly (lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

2. Host Molecules

Host molecules are molecules or materials which reversibly associate with an active agent to form a complex. By virtue of their ability to reversibly form complexes with active agents, host molecules can function to control the release of a complexed active agent in vivo.

In some cases, the host molecule is a molecule that forms an inclusion complex with an active agent. Inclusion complexes are formed when an active agent (i.e., the guest), or portion of an active agent, inserts into a cavity of another molecule, group of molecules, or material (i.e., the host). Typically, the guest molecule associates with the host molecule without affecting the framework or structure of the host. For example, in the case of inclusion complexes, the size and shape of the available cavity in the host molecule remain substantially unaltered as a consequence of complex formation.

The host molecule may be a small molecule, an oligomer, a polymer, or combinations thereof. Exemplary hosts include polysaccharides such as amyloses, cyclodextrins, and other cyclic or helical compounds containing a plurality of aldose rings, for example, compounds formed through 1,4 and 1,6 bonding of monosaccharides (such as glucose, fructose, and galactose) and disaccharides (such as sucrose, maltose, and lactose). Other exemplary host compounds include cryptands, cryptophanes, cavitands, crown ethers, dendrimers, ion-exchange resins, calixarenes, valinomycins, nigericins, catenanes, polycatenanes, carcerands, cucurbiturils, and spherands.

In still other embodiments, organic host compounds or materials include carbon nanotubes, fullerenes, and/or graphene-based host materials. Carbon nanotubes (CNTs) are allotropes of carbon with a cylindrical nanostructure. Nanotubes are members of the fullerene structural family, which also includes the spherical buckyballs, and the ends of a nanotube may be capped with a hemisphere of the buckyball structure. Their name is derived from their long, hollow structure with the walls formed by one-atom-thick sheets of carbon, called graphene. These sheets are rolled at specific and discrete ("chiral") angles, and the combination of the rolling angle and radius decides the nanotube properties. Nanotubes can be categorized as single-walled nanotubes (SWNTs) and multi-walled nanotubes (MWNTs). Nanotubes and/or fullerenes can serve as hosts, for example, by encapsulating or entrapping the material to be delivered (i.e., the guest) within the tubes or fullerenes. Alternatively, the exterior and/or interior of the tubes and/or fullerenes can be functionalized with functional groups which can complex to the guest to be delivered. Complexations include, but are not limited to, ionic interactions, hydrogen bonding, Van der Waals interactions, and pi-pi interactions, such as pi-stacking.

Graphenes are also an allotrope of carbon. The structure of graphene is a one-atom-thick planar sheet of $sp^2$-bonded carbon atoms that are densely packed in a honeycomb crystal lattice. Graphene is the basic structural element of some carbon allotropes including graphite, charcoal, carbon nanotubes and fullerenes. The guest to be delivered can associate with and/or complex to graphene or functionalized graphene as described above for nanotubes and fullerenes.

The host material can also be an inorganic material, including but not limited to, inorganic phosphates and silica.

Suitable host molecules are generally selected for incorporation into nanolipogels in view of the identity of the active agent(s) to be delivered and the desired drug release profile. In order to form a complex with the active agent being delivered, the host molecule is generally selected to be complimentary to the active agent both in terms of sterics (size) and electronics (charge and polarity). For example, in the case of host molecules that form inclusion complexes with the active agent to be delivered, the host molecule will typically possess an appropriately-sized cavity to incorporate the active agent. In addition, the host molecule typically possesses a cavity of appropriate hydrophobicity/hydrophilicity to promote complex formation with the active agent.

The strength of the guest-host interaction will influence the drug release profile of the active agent from the nanolipogel, with stronger guest-host interactions generally producing more prolonged drug release.

Generally, the host molecules are dispersed within the polymeric matrix that forms the nanolipogel core. In some cases, one or more host molecules are covalently coupled to the polymeric matrix. For example, the host molecules may be functionalized with one or more pendant reactive functional groups that react with the polymer matrix. In particular embodiments, the host molecules contain one or more pendant reactive functional groups that react with the polymer matrix to crosslink the polymer matrix. Examples of suitable reactive functional groups include methacrylates, acrylates, vinyl groups, epoxides, thiiranes, azides, and alkynes.

In certain embodiments, the host molecule is a cyclodextrin. Cyclodextrins are cyclic oligosaccharides containing six (α-cyclodextrin), seven β-cyclodextrin), eight (γ-cyclodextrin), or more α-(1,4)-linked glucose residues. The hydroxyl groups of the cyclodextrins are oriented to the outside of the ring while the glucosidic oxygen and two rings of the non-exchangeable hydrogen atoms are directed towards the interior of the cavity. As a result, cyclodextrins possess a hydrophobic inner cavity combined with a hydrophilic exterior. Upon combination with a hydrophobic active agent, the active agent (i.e., the guest) inserts into the hydrophobic interior of the cyclodextrin (i.e., the host).

The cyclodextrin may be chemically modified such that some or all of the primary or secondary hydroxyl groups of the macrocycle, or both, are functionalized with one or more pendant groups. The pendant groups may be reactive functional groups that can react with the polymeric matrix, such as methacrylates, acrylates, vinyl groups, epoxides, thiiranes, azides, alkynes, and combinations thereof. The pendant groups may also serve to modify the solubility of the cyclodextrin. Exemplary groups of this type include sulfinyl, sulfonyl, phosphate, acyl, and $C_1$-$C_{12}$ alkyl groups optionally substituted with one or more (e.g., 1, 2, 3, or 4) hydroxy, carboxy, carbonyl, acyl, oxy, and oxo groups. Methods of modifying these alcohol residues are known in the art, and many cyclodextrin derivatives are commercially available.

Examples of suitable cyclodextrins include α-cyclodextrin; β-cyclodextrin; γ-cyclodextrin; methyl α-cyclodextrin; methyl β-cyclodextrin; methyl γ-cyclodextrin; ethyl β-cyclodextrin; butyl α-cyclodextrin; butyl β-cyclodextrin; butyl γ-cyclodextrin; pentyl γ-cyclodextrin; hydroxyethyl β-cyclodextrin; hydroxyethyl γ-cyclodextrin; 2-hydroxypropyl α-cyclodextrin; 2-hydroxypropyl β-cyclodextrin; 2-hydroxypropyl γ-cyclodextrin; 2-hydroxybutyl β-cyclodextrin; acetyl α-cyclodextrin; acetyl β-cyclodextrin; acetyl γ-cyclodextrin; propionyl β-cyclodextrin; butyryl β-cyclodextrin; succinyl α-cyclodextrin; succinyl β-cyclodextrin; succinyl γ-cyclodextrin; benzoyl β-cyclodextrin; palmityl β-cyclodextrin; toluenesulfonyl β-cyclodextrin; acetyl methyl β-cyclodextrin; acetyl butyl β-cyclodextrin; glucosyl α-cyclodextrin; glucosyl β-cyclodextrin; glucosyl γ-cyclodextrin; maltosyl α-cyclodextrin; maltosyl β-cyclodextrin; maltosyl γ-cyclodextrin; α-cyclodextrin carboxymethylether; β-cyclodextrin carboxymethylether; γ-cyclodextrin carboxymethylether; carboxymethylethyl β-cyclodextrin; phosphate ester α-cyclodextrin; phosphate ester β-cyclodextrin; phosphate ester γ-cyclodextrin; 3-trimethylammonium-2-hydroxypropyl β-cyclodextrin; sulfobutyl ether β-cyclodextrin; carboxymethyl α-cyclodextrin; carboxymethyl β-cyclodextrin; carboxymethyl γ-cyclodextrin, and combinations thereof.

Preferred cyclodextrins include α-cyclodextrins, β-cyclodextrins, and γ-cyclodextrins functionalized with one or more pendant acrylate or methacrylate groups. In a particular embodiment, the host molecule is a β-cyclodextrin functionalized with multiple methacrylate groups. An exemplary host molecule of this type is illustrated below, wherein R represents a $C_1$-$C_6$ alkyl group.

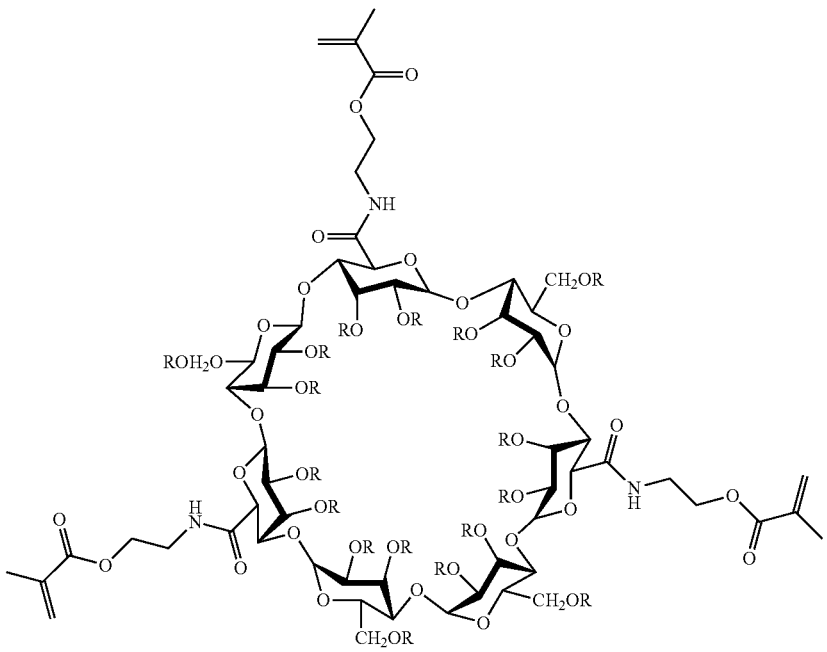

As a further example, the host molecule may also be a material that temporarily associates with an active agent via ionic interactions. For example, conventional ion exchange resins known in the art for use in controlled drug release may serve as host molecules. See, for example, Chen, et al. "Evaluation of ion-exchange microspheres as carriers for the anticancer drug doxorubicin: in vitro studies." *J. Pharm. Pharmacol.* 44(3):211-215 (1992) and Farag, et al. "Rate of release of organic carboxylic acids from ion exchange resins" *J. Pharm. Sci.* 77(10):872-875(1988).

By way of exemplification, when the active agent being delivered is a cationic species, suitable ion exchange resins may include a sulfonic acid group (or modified sulfonic acid group) or an optionally modified carboxylic acid group on a physiologically acceptable scaffold. Similarly, where the active agent is an anionic species, suitable ion exchange resins may include amine-based groups (e.g., trimethylamine for a strong interaction, or dimethylethanolamine for a weaker interaction). Cationic polymers, such as polyethyleneimine (PEI), can function as host molecules for complex oligonucleotides such as siRNA.

In other cases, the host molecule is a dendrimer, such as a poly(amidoamine) (PAMAM) dendrimer. Cationic and anionic dendrimers can function as host materials by ionically associating with active agents, as described above. In addition, medium-sized dendrimers, such as three- and four-generation PAMAM dendrimers, may possess internal voids spaces which can accommodate active agents, for example, by complexation of nucleic acids.

In some embodiments the host molecule is a dendrimer conjugated to a cyclodextrin. In some embodiments, the cyclodextrin(s) shields primary amines of dendrimer. Suitable dendrimers and cyclodextrins are discussed above. Unmodified dendrimer (i.e., generation 4 PAMAM dendrimer (G4)) was empirically better at endosomal disruption than dendrimer conjugated with cyclodexrin (CD) (See the Examples below). Without being bound by theory, it is believed that terminal amine groups on PAMAM dendrimers provide endosomal buffering and disrupt endosomes by the proton sponge effect. Accordingly, increasing CD results in a decrease in endosomal disruption. As discussed in the Examples below, different combinations of dendrimers and cyclodextrins can be used to modulate the transfection efficiency and level of endosomal disruption in the cell.

Preferably, the one or more host molecules are present in an amount of from about 0.1% to about 40% w/w of the polymeric matrix, more preferably from about 0.1% to about 25% w/w of the overall formulation.

3. Active Agents

Active agents to be delivered include therapeutic, nutritional, diagnostic, and prophylactic agents. The active agents can be small molecule active agents or biomacromolecules, such as proteins, polypeptides, or nucleic acids. Suitable small molecule active agents include organic and organometallic compounds, as well as steroids, chemotherapeutic or cytoxic compounds, radioisotype or radioactive material, macrolides, both naturally occurring and synthetic analogs, derivative, or other forms of these compounds . . . . The small molecule active agents can be a hydrophilic, hydrophobic, or amphiphilic compound.

Exemplary therapeutic agents that can be incorporated into nanolipogels include tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors to activate the innate immune system, molecules that mobilize and optimize the adaptive immune system, molecules that activate or up-regulate the action of cytotoxic T lymphocytes, natural killer cells and helper T cells, and molecules that deactivate or down-regulate suppressor or regulatory T cells), agents that promote uptake of nanolipogels into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

Exemplary diagnostic agents include paramagnetic molecules, fluorescent compounds, magnetic molecules, and radionuclides, x-ray imaging agents, and contrast agents.

In certain embodiments, the nanolipogel includes one or more anti-cancer agents. Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), anti-metabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

In certain embodiments, the nanolipogel includes one or more immunomodulatory agents. Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

In one embodiment, the active agent is a therapeutic used to treat autoimmune diseases such as rheumatoid arthritis and lupus.

Nonsteroidal anti-inflammatory drugs (NSAIDs), which are administered to help ease symptoms like pain, swelling and stiffness, can be used. The most common used NSAIDs are ibuprofen and naproxen. Disease-modifying anti-rheumatic drugs (DMARDs), are agents which slow down—or even halt—the progress of a disease. The workhorse of this group is methotrexate. Other DMARDs include sulfasalazine (brand name Azulfidine) and leflunomide (Arava).

The major category within biologics is tumor necrosis factor (TNF) blockers, which counteract high levels of inflammatory proteins. Etanercept (Enbrel), infliximab (Remicade) and adalimumab (Humira) are the most widely used. Another promising group is interleukin-1 (IL-1) blockers like anakinra (Kineret).

Corticosteroids include prednisolone, hydrocortisone, methylprednisolone, dexamethasone, cortisone, triamcinolone, and betamethasone.

Mycophenolate mofetil (MMF) and its active metabolite mycophenolic acid (MPA) are both very effective immunosuppressive agent. MMF has been used to treat autoimmune and inflammatory skin diseases. Lipsky, *Lancet,* 348:L1357-1359 (1996) and has become a valuable therapeutic option in children with autoimmune disease. Filler, et al., *Pediatric Rheumatol.,* 8:1 (2010). Mycophenolic acid (MPA) is a relatively new adjuvant drug that selectively inhibits T and B lymphocyte proliferation by suppressing de novo purine synthesis. Other steroid sparing immunosuppressive agents include azathioprine, methotrexate and cyclophosphamide. In a preferred embodiment, the active immunosuppressant is MPA. The examples show hydrogel-based nanoparticles that were loaded with the immunosuppressant drug mycophenolic acid (MPA).

MPA is the active form of mycophenolate mofetil, which is currently used as an immunosuppressant in humans for lupus and other autoimmune disease therapy (Ginzler, et al., *N Engl J Med,* 353(21):2219-28 (2005)). We chose to encapsulate MPA in nanoparticles because it has broad immunosuppressive effects on several immune cell types. MPA blocks the de novo synthesis pathway of guanine nucleotides. T and B cell proliferation is acutely impaired by MPA because these cells lack the biosynthetic salvage pathways that could circumvent impaired de novo guanine production (Jonsson, et al., *Clin Exp Immunol,* 124(3): 486-91 (2001); Quemeneur, et al., *J Immunol,* 169(5):2747-55 (2002); Jonsson, et al., *Int Immunopharmacol,* 3(1):31-7 (2003); and Karnell, et al., *J Immunol,* 187(7): 3603-12 (2011). Furthermore, MPA can impair the activation of dendritic cells and their ability to stimulate alloantigen responses (Mehling, et al., *J Immunol,* 165(5):2374-81 (2000); Lagaraine, et al., *Int Immunol,* 17(4):351-63 (2005); and Wadia, et al., *Hum Immunol,* 70(9):692-700 (2009)), and has been suggested to promote the development of tolerogenic dendritic cells (Lagaraine, et al., *J Leukoc Biol,* 84(4):1057-64 (2008)). Like many immunosuppressant drugs, MPA is very hydrophobic, with a reported partition coefficient (log P value) of 3.88 (Elbarbry, et al., *J Chromatogr B Analyt Technol Biomed Life Sci,* 859(2): 276-81 (2007)).

In a preferred embodiment demonstrated by the examples, the host molecule is used to deliver a hydrophobic agent for example, the immunosuppressant, MPA. An immunosuppressant may include any small molecule that suppresses the function of the immune system or that increases susceptibility to infectious diseases. In certain preferred embodiments, the immunosuppressant is an inhibitor of T cell proliferation, an inhibitor of B cell proliferation, or an inhibitor of T cell and B cell proliferation. In certain embodiments the T cell or B cell proliferation inhibitors inhibit or regulate the synthesis of guanine monophosphate. For example, the immunosuppressant can be mycophenolic acid, the structure of which is shown below.

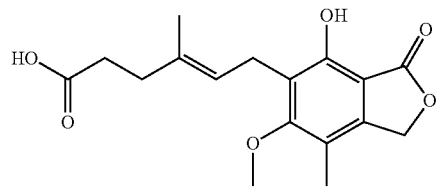 [SMILES: COc1c(C)c2c(c(O)c1C/C=C(\C)CCC(=O)O)C(=O)OC2]

Alternatively, the immunosuppressant is a prodrug of mycophenolic acid including, but not limited to, mycophenolate mofetil (marketed under the trade names CELL-CEPT® by the Swedish company F. Hoffmann-La Roche Ltd.), the structure of which is shown below.

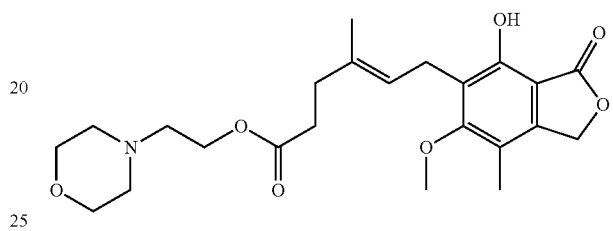

A salt of the immunosuppressant may also be used, for example, a salt of mycophenolic acid includes, but is not limited to, the mycophenolate sodium (marketed under the trade name MYFORTIC® by Novartis). In certain preferred embodiments the immunosuppressant is a synthetically modified analogue of mycophenolic acid.

In some embodiments, the immunosuppressant is a purine analogue including, but not limited to, azathioprine (marketed under a variety of trade names including AZASAN® by Salix and IMURAN® by GlaxoSmithKline) or mercaptopurine (marketed under the trade name PURINETHOL® ((Mercaptopurine). In some embodiments the immunosuppressant is an antimetabolite that inhibits the use and/or the synthesis of purines, such as a purine nucleoside phosphorylase inhibitor.

Intravenous immunoglobulin (IVIg), which is a blood product made up of antibodies that is delivered by IV, is used to get the immune system back on track without suppressing its normal function.

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A. In a specific embodiment, the immunological adjuvant is MPL. In another embodiment, the immunological adjuvant is LPS. TLR ligands can also include, but are not limited to, TLR3 ligands (e.g., polyinosinic-polycytidylic acid (poly(I:C)), TLR7 ligands (e.g., imiquimod and resiquimod), and TLR9 ligands.

The nanolipogel may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

In certain embodiments, the nanolipogel core contains two or more active agents. In preferred embodiments, the nanolipogel core contains both a small molecule hydrophobic active agent, preferably associated with one or more suitable host molecules, and a hydrophilic active agent dispersed within the polymeric matrix. In particular embodiments, the hydrophilic active agent is a protein, such as a therapeutic cytokine. By incorporating a hydrophobic active agent in association with a host molecule and a hydrophilic molecule dispersed within the polymeric matrix, controlled release of two or more active agents, including two or more active agents with varied physiochemical characteristics (such as solubility, hydrophobicity/hydrophilicity, molecular weight, and combinations thereof) can be achieved.

In a preferred embodiment demonstrated by the examples, the host molecule is used to deliver a low molecular weight compounds such as an chemotherapeutic, where the host molecule retards release of the low molecular weight compound, and a larger hydrophilic compound, such as a cytokine, so that release of both molecules occurs over a similar time period.

B. Shell Components

Nanolipogels include a liposomal shell composed of one or more concentric lipid monolayers or lipid bilayers. The shell can further include one or active agents, targeting molecules, or combinations thereof.

1. Lipids

Nanolipogels include a liposomal shell composed of one or more concentric lipid monolayers or lipid bilayers. The composition of the liposomal shell may be varied to influence the release rate of one or more active agents in vivo. The lipids may also be covalently crosslinked, if desired, to alter in vivo drug release.

The lipid shell can be formed from a single lipid bilayer (i.e., the shell may be unilamellar) or several concentric lipid bilayers (i.e., the shell may be multilamellar). The lipid shell may be formed from a single lipid; however, in preferred embodiments, the lipid shell is formed from a combination of more than one lipid. The lipids can be neutral, anionic or cationic lipids at physiologic pH.

Suitable neutral and anionic lipids include sterols and lipids such as cholesterol, phospholipids, lysolipids, lysophospholipids, and sphingolipids. Neutral and anionic lipids include, but are not limited to, phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids, such as sphingomyelin; sphingoglycolipids (also known as 1-ceramidyl glucosides), such as ceramide galactopyranoside, gangliosides and cerebrosides; fatty acids, sterols containing a carboxylic acid group such as cholesterol or derivatives thereof; and 1,2-diacyl-sn-glycero-3-phosphoethanolamines, including 1,2-dioleoyl-sn-Glycero-3-phosphoethanolamine or 1,2-dioleolylglyceryl phosphatidylethanolamine (DOPE), 1,2-dihexadecylphosphoethanolamine (DHPE), 1,2-distearoylphosphatidylcholine (DSPC), 1,2-dipalmitoylphosphatidylcholine (DPPC), and 1,2-dimyristoylphosphatidylcholine (DMPC). Also suitable are natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of these lipids.

Suitable cationic lipids include N-[1-(2,3-dioleoyloxy)propyl]-N,N,N-trimethyl ammonium salts, also referred to as TAP lipids, for example as a methylsulfate salt. Suitable TAP lipids include, but are not limited to, DOTAP (dioleoyl-), DMTAP (dimyristoyl-), DPTAP (dipalmitoyl-), and DSTAP (distearoyl-). Other suitable cationic lipids include dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxyl)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyltrimethylammonium bromide (CTAB), $diC_{14}$-amidine, N-tert-butyl-N'-tetradecyl-3-tetradecylamino-propionamidine, N-(alpha-trimethylammonio-acetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide, 1-[2-(acyloxy)ethyl]2-alkyl(alkenyl)-3-(2-hydroxyethyl)-imidazolinium chloride derivatives, such as 1-[2-(9 (Z)-octadecenoyloxy)ethyl]-2-(8(Z)-heptadecenyl-3-(2-hydroxyethyl)imidazolinium chloride (DOTIM) and 1-[2-(hexadecanoyloxy)ethyl]-2-pentadecyl-3-(2-hydroxyethyl) imidazolinium chloride (DPTIM), and 2,3-dialkyloxypropyl quaternary ammonium derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Other suitable lipids include PEGylated derivatives of the neutral, anionic, and cationic lipids described above. Incorporation of one or more PEGylated lipid derivatives into the lipid shell can result in a nanolipogel which displays polyethylene glycol chains on its surface. The resulting nanolipogels may possess increased stability and circulation time in vivo as compared to nanolipogels lacking PEG chains on their surfaces. Examples of suitable PEGylated lipids include distearoylphosphatidylethanlamine-polyethylene glycol (DSPE-PEG), including DSPE PEG (2000 MW) and DSPE PEG (5000 MW), dipalmitoyl-glycero-succinate polyethylene glycol (DPGS-PEG), stearyl-polyethylene glycol and cholesteryl-polyethylene glycol.

In preferred embodiments, the lipid shell is formed from a combination of more than one lipid. In certain embodiments the lipid shell is formed from a mixture of at least three lipids. In particular embodiments, the lipid shell is formed from a mixture of phosphatidyl choline (PC), 1,2-distearoyl-sn-glycero-3-phosphoethanolamine-N-[amino (polyethylene glycol)-2000] (DSPE-PEG), and cholesterol.

In some embodiments, the lipid shell is formed from a mixture of one or more PEGylated phospholipids and one or more additional lipids or sterols. In certain instances, the molar ratio of the one or more PEGylated lipids to the one or more additional lipids or sterols ranges from about 1:1 to about 1:6, more preferably from about 1:2 to about 1:6, most preferably from about 1:3 to about 1:5. In particular embodiments, the molar ratio of the one or more PEGylated lipids to the one or more additional lipids or sterols is about 1:4.

In some embodiments, the lipid shell is formed from a mixture of one or more phospholipids and one or more additional lipids or sterols. In certain instances, the molar ratio of the one or more phospholipids to the one or more additional lipids or sterols ranges from about 1:1 to about 6:1, more preferably from about 2:1 to about 6:1, most preferably from about 3:1 to about 5:1. In particular embodiments, the molar ratio of the one or more phospho lipids to the one or more additional lipids or sterols is about 4:1.

In a preferred embodiments, the lipid shell is formed from a mixture of a phospholipid, such as phosphatidyl choline (PC), a PEGylated phospholipid, such as 1,2-distearoyl-sn-glycero-3-phosphoethanolamine-N-[amino(polyethylene glycol)-2000] (DSPE-PEG), and cholesterol. In particular embodiments, the lipid shell is formed from a mixture of phosphatidyl choline, 1,2-distearoyl-sn-glycero-3-phosphoethanolamine-N-[amino(polyethylene glycol)-2000] (DSPE-PEG), and cholesterol in a 3:1:1 molar ratio.

2. Targeting Molecules and Molecules Decreasing RES Uptake

The surface of the nanolipogels, or the core host, can be modified to facilitate targeting through the attachment of targeting molecules. Exemplary target molecules include proteins, peptides, nucleic acids, lipids, saccharides, or polysaccharides that bind to one or more targets associated with an organ, tissue, cell, or extracellular matrix, or specific type of tumor or infected cell. The degree of specificity with which the nanolipogels are targeted can be modulated through the selection of a targeting molecule with the appropriate affinity and specificity. For example, a targeting moiety can be a polypeptide, such as an antibody that specifically recognizes a tumor marker that is present exclusively or in higher amounts on a malignant cell (e.g., a tumor antigen). Suitable targeting molecules that can be used to direct nanoparticles to cells and tissues of interest, as well as methods of conjugating target molecules to nanoparticles, are known in the art. See, for example, Ruoslahti, et al. *Nat. Rev. Cancer*, 2:83-90 (2002). Targeting molecules can also include neuropilins and endothelial targeting molecules, integrins, selectins, and adhesion molecules. Targeting molecules can be covalently bound to nanolipogels using a variety of methods known in the art.

In certain embodiments, the liposomal shell includes one or more PEGylated lipids. The PEG, or other hydrophilic polyalkylene oxide, avoids uptake of the lipogels by the reticuloendothelial system ("RES"), thereby prolonging in vivo residence time.

The surface of the nanolipogels can be modified to facilitate targeting through the attachment of targeting molecules. These can be proteins, peptides, nucleic acid molecules, saccharides or polysaccharides that bind to a receptor or other molecule on the surface of a targeted cell. The degree of specificity can be modulated through the selection of the targeting molecule. For example, antibodies are very specific. These can be polyclonal, monoclonal, fragments, recombinant, or single chain, many of which are commercially available or readily obtained using standard techniques. T-cell specific molecules and antigens which are bound by antigen presenting cells as well as tumor targeting molecules can be bound to the surface of the nanolipogel and/or to the host molecule. The targeting molecules may be conjugated to the terminus of one or more PEG chains present on the surface of the liposomal shell.

3. Active Agents

The shell of the nanolipogels may optionally contain one or more active agents, including any of the active agents described above.

Hydrophobic active agents, such as proteins, may be covalently connected to the surface of the nanolipogel, whereas hydrophilic active agents may be covalently connected to the surface of the nanolipogel or dispersed within the liposomal shell. In certain embodiments, the liposomal shell includes one or more PEGylated lipids. In these cases, one or more active agents may be conjugated to the terminus of one or more PEG chains present on the surface of the liposomal shell. In particular embodiments, one or more active agents are covalently connected to the surface of the nanolipogel via a linking group that is cleaved in response to an external chemical or physical stimulus, such as a change in ambient pH, so as to trigger release of the active agent at a desired physiological locale.

III. Methods of Manufacture, Loading, and Pharmaceutical Compositions

A. Methods of Manufacture and Loading

"Nanolipogel", a nanoparticle that combines the advantages of both liposomes and polymer-based particles for sustained delivery of nucleic acids, proteins and small molecules. The nanolipogel can be in the form of spheres, discs, rods or other geometries with different aspect ratios. The nanosphere can be larger, i.e., microparticles. The nanolipogel is typically formed of synthetic or natural polymers capable of encapsulating agents by remote loading and tunable in properties so as to facilitate different rates of release. Release rates are modulated by varying the polymer to lipid ratio from 0.05 to 5.0, more preferably from 0.5 to 1.5.

Nanolipogels are designed to be loaded with agents either prior to, during or after formation and subsequently function as controlled-release vehicles for the agents. The nanolipogel can be loaded with more than one agent such that controlled release of the multiplicity of agents is subsequently achieved.

The nanolipogel is loaded with one or more first agents during formation and one or more second agents following formation by the process of rehydration of the nanolipogel in the presence of the second agents. For example, the nanolipogel is loaded with a molecule that serves as an adjuvant and the nanolipogel thereafter incorporates one or more target antigens after formation, for the controlled release of adjuvant together with the antigens. Alternatively, the nanolipogel loaded with adjuvant is inserted into the site of a tumor in a patient, the tumor is ablated, the nanolipogel is loaded with released tumor antigens and the nanolipogel releases the tumor antigens together with adjuvant into the body of the patient in a controlled manner.

In another embodiment, the nanolipogel is loaded with an antigen, a molecule that serves as an adjuvant and a targeting molecule for antigen presenting cells, the nanolipogel is taken up by antigen presenting cells and the antigen is appropriately processed and presented to T-helper and cytotoxic T-cells to promote a cell-mediated immune response.

In yet another embodiment, the nanolipogel loaded with a molecule that serves as an adjuvant and a targeting molecule for antigen presenting cells is inserted into the site of a tumor in a patient, the tumor is ablated and the nanolipogel is loaded with released tumor antigens, the nanolipogel is taken up by antigen presenting cells and the released tumor antigens are appropriately processed and presented to T-helper and cytotoxic T-cells to promote a cell-mediated immune response.

B. Pharmaceutical Compositions

Pharmaceutical compositions including nanolipogels are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example, by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the nanolipogels to the immediate area of the implant.

The nanolipogels can be provided to the cell either directly, such as by contacting it with the cell, or indirectly, such as through the action of any biological process. For example, the nanolipogels can be formulated in a physiologically acceptable carrier or vehicle, and injected into a tissue or fluid surrounding the cell. The nanolipogels can cross the cell membrane by simple diffusion, endocytosis, or by any active or passive transport mechanism.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower. Generally, the total amount of the nanolipogel-associated active agent administered to an individual will be less than the amount of the unassociated active agent that must be administered for the same desired or intended effect.

1. Formulations for Parenteral Administration

In a preferred embodiment the nanolipogels are administered in an aqueous solution, by parenteral injection.

The formulation can be in the form of a suspension or emulsion. In general, pharmaceutical compositions are provided including effective amounts of one or more active agents optionally include pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical and Mucosal Administration

The nanolipogels can be applied topically. Topical administration can include application to the lungs, nasal, oral (sublingual, buccal), vaginal, or rectal mucosa. These methods of administration can be made effective by formulating the shell with transdermal or mucosal transport elements. For transdermal delivery such elements may include chemical enhancers or physical enhancers such as electroporation or microneedle delivery. For mucosal delivery PEGylation of the outer shell or addition of chitosan or other mucosal permeants or PH protective elements for oral delivery.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to, nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets, capsules, or lozenges. Oral formulations may include excipients or other modifications to the particle which can confer enteric protection or enhanced delivery through the GI tract, including the intestinal epithelia and mucosa (see Samstein, et al., *Biomaterials,* 29(6): 703-8 (2008).

Transdermal formulations may also be prepared. These will typically be ointments, lotions, sprays, or patches, all of which can be prepared using standard technology. Transdermal formulations can include penetration enhancers. Chemical enhancers and physical methods including electroporation and microneedles can work in conjunction with this method.

IV. Methods of Treatment

The methods of treatment disclosed herein typically include using a nanolipogel loaded with one or more active agents, to deliver the one or more active agents into a cell, or to a cell's microenvironment. The methods typically include contacting the active agent-loaded nanolipogel with one more cells. The contacting can occur in vivo or in vitro.

Administration of a drug or other cargo to cells or a subject using nanolipogels can be compared to a control, for example, delivery of the drug or other cargo to cells or a subject using conventional delivery methods such as free cargo/drug delivery, delivery using conventional PLGA nanoparticles, or delivery using conventional liposomal methods such as LIPOFECTAMINE®. Nanolipogels can be used to deliver cargo to a target cells with increased efficacy compared to conventional delivery methods. In some embodiments less cargo or drug is required when delivered using nanolipogels compared to conventional delivery methods to achieve the same or greater therapeutic benefit.

In some embodiments toxicity is reduced or absent compared to conventional delivery methods. For example, in some embodiments, white blood cell, platelet, hemoglobin, and hematocrit levels were within normal physiological ranges; no liver or renal toxicities are observed; body weight and serum concentrations for alkaline phosphatase, alanine transferase, total bilirubin, and blood urea nitrogen are normal; or combinations thereof following administration of loaded nanolipogels to the subject.

A. In Vivo Methods

The disclosed compositions can be used in a method of delivering active agents to cells in vivo. In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

1. Drug Delivery

The particles described herein can be used to deliver an effective amount of one or more therapeutic, diagnostic, and/or prophylactic agents to a patient in need of such treatment. The amount of agent to be administered can be readily determine by the prescribing physician and is dependent on the age and weight of the patient and the disease or disorder to be treated.

The particles are useful in drug delivery (as used herein "drug" includes therapeutic, nutritional, diagnostic and prophylactic agents), whether injected intravenously, subcutaneously, or intramuscularly, intraperitoneally, administered to the nasal or pulmonary system, injected into a site of inflammation, administered to a mucosal surface (vaginal, rectal, buccal, sublingual), or encapsulated for oral delivery. The particles may be administered as a dry powder, as an aqueous suspension (in water, saline, buffered saline, etc), in a hydrogel, organogel, in capsules, tablets, troches, or other standard pharmaceutical excipients. The preferred embodiments are aqueous suspensions and dry powders that have been resuspended into aqueous/gel form.

As discussed herein, compositions can be used to as delivery vehicles for a number of active agents including small molecules, nucleic acids, proteins, and other bioactive agents. The active agent or agents can be encapsulated within, dispersed within, and/or associated with the surface of the nanolipogel particle. In some embodiments, the nanolipogel packages two, three, four, or more different active agents for simultaneous delivery to a cell.

2. Transfection

The disclosed compositions can be for cell transfection of polynucleotides. As discussed in more detail below, the transfection can occur in vitro or in vivo, and can be applied in applications including gene therapy and disease treatment. The compositions can be more efficient, less toxic, or a combination thereof when compared to a control. In some embodiments, the control is cells treated with an alternative transfection reagent such as LIPOFECTAMINE 2000.

The particular polynucleotide delivered by the nanolipogel can be selected by one of skill in the art depending on the condition or disease to be treated. The polynucleotide can be, for example, a gene or cDNA of interest, a functional nucleic acid such as an inhibitory RNA, a tRNA, an rRNA, or an expression vector encoding a gene or cDNA of interest, a functional nucleic acid a tRNA, or an rRNA. In some embodiments two or more polynucleotides are administered in combination. In some embodiments, the polynucleotide encodes a protein.

In some embodiments, the polynucleotide is not integrated into the host cell's genome (i.e., remains extrachromosomal). Such embodiments can be useful for transient or regulated expression of the polynucleotide, and reduce the risk of insertional mutagenesis. Therefore, in some embodiments, the nanolipogels are used to deliver mRNA or non-integrating expression vectors that are expressed transiently in the host cell.

In some embodiments, the polynucleotide is integrated into the host cell's genome. For example, gene therapy is a technique for correcting defective genes responsible for disease development. Researchers may use one of several approaches for correcting faulty genes: (a) a normal gene can be inserted into a nonspecific location within the genome to replace a nonfunctional gene. This approach is most common; (b) an abnormal gene can be swapped for a normal gene through homologous recombination; (c) an abnormal gene can be repaired through selective reverse mutation, which returns the gene to its normal function; (d) the regulation (the degree to which a gene is turned on or off) of a particular gene can be altered.

Gene therapy can include the use of viral vectors, for example, adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

Gene targeting via target recombination, such as homologous recombination (HR), is another strategy for gene correction. Gene correction at a target locus can be mediated by donor DNA fragments homologous to the target gene (Hu, et al., *Mol. Biotech.*, 29:197-210 (2005); Olsen, et al., *J. Gene Med.*, 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oligonucleotides can interact with either double-stranded or single-stranded nucleic acids.

Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406. Highly stable PNA:DNA:PNA triplex structures can be formed from strand invasion of a duplex DNA with two PNA strands. In this complex, the PNA/DNA/PNA triple helix portion and the PNA/DNA duplex portion both produce displacement of the pyrimidine-rich triple helix, creating an altered structure that has been shown to strongly provoke the nucleotide excision repair pathway and to activate the site for recombination with the donor oligonucleotide. Two PNA strands can also be linked together to form a bis-PNA molecule.

The triplex-forming molecules are useful to induce site-specific homologous recombination in mammalian cells when used in combination with one or more donor oligonucleotides which provides the corrected sequence. Donor oligonucleotides can be tethered to triplex-forming molecules or can be separate from the triplex-forming molecules. The donor oligonucleotides can contain at least one nucleotide mutation, insertion or deletion relative to the target duplex DNA.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406. Pseudocomplementary oligonucleotides are complementary oligonucleotides that contain one or more modifications such that they do not recognize or hybridize to each other, for example due to steric hindrance, but each can recognize and hybridize to complementary nucleic acid strands at the target site. In some embodiments, pseudocomplementary oligonucleotides are pseudocomplemenary peptide nucleic acids (pcPNAs). Pseudocomplementary oligonucleotides can be more efficient and provide increased target site flexibility over methods of induced recombination such as triple-helix oligonucleotides and bis-peptide nucleic acids which require a polypurine sequence in the target double-stranded DNA.

B. In Vitro Methods

The disclosed compositions can be used in a method of delivering active agents to cells in vitro. For example, the nanolipogels can be used for in vitro transfection of cells. The method typically involves contacting the cells with nanolipogel including a polynucleotide in an effective amount to introduce the polynucleotide into the cell's cytoplasm. In some embodiments, the polynucleotide is delivered to the cell in an effective amount to change the genotype or a phenotype of the cell. The cells can primary cells isolated from a subject, or cells of an established cell line. The cells can be of a homogenous cell type, or can be a heterogeneous mixture of different cells types. For example, the polyplexes can be introduced into the cytoplasm of cells from a heterogenous cell line possessing cells of different types, such as in a feeder cell culture, or a mixed culture in various states of differentiation. The cells can be a transformed cell line that can be maintained indefinitely in cell culture. Exemplary cell lines are those available from American Type Culture Collection including tumor cell lines.

Any eukaryotic cell can be transfected to produce cells that express a specific nucleic acid, for example a metabolic gene, including primary cells as well as established cell lines. Suitable types of cells include but are not limited to undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Suitable differentiated cells include somatic cells, neuronal cells, skeletal muscle, smooth muscle, pancreatic cells, liver cells, and cardiac cells. In another embodiment, siRNA, antisense polynucleotides (including siRNA or antisense polynucleotides) or inhibitory RNA can be transfected into a cell using the compositions described herein.

The methods are particularly useful in the field of personalized therapy, for example, to repair a defective gene, de-differentiate cells, or reprogram cells. For example, target cells are first isolated from a donor using methods known in the art, contacted with the nanolipogel including a polynucleotide causing a change to the in vitro (ex vivo), and administered to a patient in need thereof. Sources or cells include cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200, or 1000 orders of magnitude. Once target cells have been isolated, they may be propagated by growing in suitable medium according to established methods known in the art. Established cell lines may also be useful in for the methods. The cells can be stored frozen before transfection, if necessary.

Next the cells are contacted with the disclosed composition in vitro to repair, de-differentiate, re-differentiate, and/or re-program the cell. The cells can be monitored, and the desired cell type can be selected for therapeutic administration.

Following repair, de-differentiation, and/or re-differentiation and/or reprogramming, the cells are administered to a patient in need thereof. In the most preferred embodiments, the cells are isolated from and administered back to the same patient. In alternative embodiments, the cells are isolated from one patient, and administered to a second patient. The method can also be used to produce frozen stocks of altered cells which can be stored long-term, for later use. In one embodiment, fibroblasts, keratinocytes or hematopoietic stem cells are isolated from a patient and repaired, de-differentiated, or reprogrammed in vitro to provide therapeutic cells for the patient.

C. Treatment of Inflammatory and Autoimmune Diseases

Chronic and persistent inflammation is a major cause of the pathogenesis and progression of systemic autoimmune diseases such as rheumatoid arthritis (RA) and systemic lupus erythematosus (SLE). Accordingly, methods of treating inflammatory and autoimmune diseases and disorders can include administering to a subject in need thereof, an effective amount of a loaded nanolipogel formulation or a pharmaceutical composition thereof, to reduce or ameliorate one or more symptoms of the disease or condition.

For example, the nanolipogel can include active agents that facilitate inhibition of cell cycle progression of T cells, for example, activated T cells (i.e., $CD44^{hi}$ T cells). The reduction can be in activated peripheral blood CD4+ T cells, splenic CD4+ T cells, or a combination thereof. In some embodiments, IFN-γ producing T cells are reduced. Preferably there is little or no reduction in regulatory T cells. In some embodiments there is an increase in regulatory T cells (Tregs).

In some embodiments, the composition is administered in an effective amount to induce or increase immunosuppression by modulating immune cell function or activation state rather than by lymphodepletion. For example, in some embodiments, the composition reduces activation of CD4+ T cells, reduces the stimulatory capacity of antigen presenting cells such as dendritic cells, or a combination thereof. Lymphodepletion/immune cell depletion may also be achieved with increases in dosing or with the use of other drugs.

In some embodiments the composition is administered in an effective amount to increase differentiation of CD4+ T cells into Fox3+CD25+ Tregs.

In some embodiments the composition is administered in an effective amount to reduce the amount of one or more proinflammatory molecules, the expression of major histocompatibility complex (MHC) I or II, or a combination thereof. Exemplary proinflammatory molecules include, but are not limited to IL-1β, TNF-α, TGF-beta, IFN-γ, IFN-α, IL-17, IL-6, IL-23, IL-22, IL-21, IL-12 and MMPs In a preferred embodiment, the composition is administered in an effective amount to reduce dendritic cell production of TNF-α, IFN-γ, or IL-12, or reduce dendritic cell expression of MHC I or MHC II, or combinations thereof. In some embodiment CD4+ T cell production of IFN-γ is reduced.

In some embodiments, the composition mediates T cell depletion in conjunction with the modulation of antigen presenting cells so that they are less potent stimulators or become more tolerogenic.

The Examples below show that nanolipogels effectively traffic to immune cells (i.e., in the lymph and spleen, etc.) without a targeting moiety. Accordingly, a targeting moiety is not required to target nanolipogels to dendritic cells or T cells. However, in some embodiments, a targeting moiety is added to the nanolipogel particle to increase targeting to a specific immune cell type, or tissue within the body. For example, depletion of activated CD4-positive T cells, in conjunction with the modulation of antigen presenting cells, such as dendritic cells, so that they are less potent stimulators or become tolerogenic, could reduce one or more disease symptoms or increase the duration of disease remission by suppressing T cell mediated autoimmunity through two distinct but additive pathways. Thus it could be advantageous to use a balance of nanoparticle targeting to both T cells (i.e., activate CD4+ T cells) and dendritic cells.

In some embodiments this is accomplished by co-administering two different particles, one decorated with a targeting moiety that enhances delivery to T cells and one with a targeting moiety that enhances delivery to antigen presenting cells such as dendritic cells. In one embodiment, the targeting moiety that directs particles to the CD4 cells is a CD4 antibody or antigen binding fragment thereof one or a moiety specifically targeting the T cell receptor. A targeting moiety that directs particles to dendritic cells such as by targeting to the DEC-205 receptor, any toll-like receptor, cell surface marker or receptor or other C-type lectins on dendritic cells can also be used. The particles can include one or more active agents. For example, the active agent(s) targeted to T cells can reduce proliferation or activation of T cells, while the active agent(s) can induce dendritic cells to be tolerogenic or suppress their antigen presenting ability or T cell inducing activity. The two different nanolipogels can be loaded with the same or different active agent(s). In a preferred embodiment, at least one of the active agents is mycophenolic acid (MPA), or a derivative or analogue thereof.

In some embodiments, nanoparticles designed with enhanced penetration to the white pulp of the secondary lymphoid organs to better inhibit T and B lymphocyte proliferation.

The disclosed nanolipogels typically carry one or more active agents effective for treating one or more symptoms of an inflammatory or autoimmune disease or disorder for delivery to a cell or tissue in a subject in need thereof. Therapeutic agents include, but are not limited to, immunosuppressive agents, e.g., antibodies against other lymphocyte surface markers (e.g., CD40) or against cytokines, other fusion proteins, e.g., CTLA4Ig, or other immunosuppressive drugs (e.g., cyclosporin A, FK506-like compounds, rapamycin compounds, or steroids), anti-proliferatives, cytotoxic agents, or other compounds that may assist in immunosuppression.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO 95122972, WO 95116691, WO 95104738, U.S. Pat. No. 6,015,809; U.S. Pat. No. 5,989,591; U.S. Pat. Nos. 5,567,709; 5,559,112; 5,530,006; 5,484,790; 5,385,908; 5,202,332; 5,162,333; 5,780,462; 5,120,727).

"FK506 compounds" includes FK506, and FK506 derivatives and analogs, e.g., compounds with structural similarity to FK506, e.g., compounds with a similar macrocyclic structure which have been modified to enhance their therapeutic effectiveness. Examples of FK506 compounds include, for example, those described in WO 00101385. The language "rapamycin compound" as used herein does not include FK506-like compounds.

Other suitable therapeutics include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chloroprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

In some embodiments, the active agent is an anti-inflammatory cytokine or chemokine, for example, interleukin (IL)-1 receptor antagonist, IL-4, IL-6, IL-10, IL-11, and IL-13. Specific cytokine receptors for IL-1, tumor necrosis factor-alpha, and IL-18 also function as pro-inflammatory cytokine inhibitors. The nature of anti-inflammatory cytokines and soluble cytokine receptors are known in the art and discussed in Opal and DePalo, Chest, 117(4):1162-72 (2000).

Retinoic acid is an additional therapeutic compound that could be used as an antinflammatory agent. See, for example, Capurso, et a. Self/Nonself, 1:4, 335-340 (2010).

Alternatively, antigens/epitopes specific to an autoimmune condition for which tolerance is lost may be added for antigen-specific immunosuppression.

As discussed in more detail below and in the Examples, a preferred active agent is MPA.

1. Autoimmune Disease

The autoimmune disease systemic lupus erythematosus (SLE) is characterized by multi-organ damage that is caused by T and B cells that promote autoantibody production and innate immune cells that mediate inflammation. The ability to target and inactivate these immune cells with immunosuppressive drugs is a much sought after modality for lupus therapies and autoimmune disease in general.

The examples demonstrate that nanogels loaded with mycophenolic acid (MPA), a commonly used immunosuppressant drug, extended the survival of lupus-prone NZB/W F1 mice by 12 weeks compared to an equivalent dose of free drug. A 16-fold greater dose of MPA administered in buffer could not achieve the same therapeutic effect as MPA-loaded nanogels. Strikingly, the nanogel mechanism of therapy was dependent on efficient trafficking to lymphoid organs, and their association with CD4 T cells as well as conventional and plasmacytoid dendritic cells. Cells which have bound or internalized nanogels were shown to be less proliferative and have reduced production of inflammatory cytokines. The results reveal for the first time a comprehensive study in the potential use of nanoparticles for lupus therapy and implicate a mechanism for enhancing therapeutic immunosuppression in autoimmune disease by targeting both T cells and antigen-presenting cells.

Strikingly, the nanogel mechanism of therapy was dependent on efficient trafficking to lymphoid organs. Nanolipogels associated with CD4 T cells as well as conventional and plasmacytoid dendritic cells. Cells which have bound or internalized nanogels were shown to be less proliferative and have reduced production of inflammatory cytokines.

Accordingly, in a preferred embodiment, the nanolipogel is used to deliver MPA to a CD4 T cells, dendritic cells, or a combination thereof in an effective amount to a reduce one or more symptoms of SLE.

Mesangial cells in the kidney promote the glomerular damage associated with lupus mortality, and methods that inhibit these cells represent an alternative, and potentially synergistic, mechanism of therapy. Accordingly, in some embodiments, nanolipogels carrying an active agent that inhibits mesangial cells, for example MPA, are targeted to kidney.

In some embodiments, the compositions reduce one or more symptoms of SLE. For example, the composition can prevent, delay, or reduce the severity of proteinuria; reduce the production of anti-nuclear autoantibodies (ANA); reduce abnormal lympoproliferation; prevent, delay or reduce glomerular nephritis; reduce, prevent or delay elevated blood urea levels; or combinations thereof. Treatment is similar for other types of autoimmune disease such as psoriasis and rheumatoid arthritis.

2. Allergies

A similar methodology can be used to treat allergies, substituting the allergen of interest for the autoimmune stimulus.

Allergies are abnormal reactions of the immune system that occur in response to otherwise harmless substances. Allergies are among the most common of medical disorders. It is estimated that 60 million Americans, or more than one in every five people, suffer from some form of allergy, with similar proportions throughout much of the rest of the world. Allergy is the single largest reason for school absence and is a major source of lost productivity in the workplace.

An allergy is a type of immune reaction. Normally, the immune system responds to foreign microorganisms or particles by producing specific proteins called antibodies. These antibodies are capable of binding to identifying molecules, or antigens, on the foreign particle. This reaction between antibody and antigen sets off a series of chemical reactions designed to protect the body from infection. Sometimes, this same series of reactions is triggered by harmless, everyday substances such as pollen, dust, and animal danders. When this occurs, an allergy develops against the offending substance (an allergen.)

Mast cells, one of the major players in allergic reactions, capture and display a particular type of antibody, called immunoglobulin type E (IgE) that binds to allergens. Inside mast cells are small chemical-filled packets called granules. Granules contain a variety of potent chemicals, including histamine.

Immunologists separate allergic reactions into two main types: immediate hypersensitivity reactions, which are predominantly mast cell-mediated and occur within minutes of contact with allergen; and delayed hypersensitivity reactions, mediated by T cells (a type of white blood cells) and occurring hours to days after exposure.

Inhaled or ingested allergens usually cause immediate hypersensitivity reactions. Allergens bind to IgE antibodies on the surface of mast cells, which spill the contents of their granules out onto neighboring cells, including blood vessels and nerve cells. Histamine binds to the surfaces of these other cells through special proteins called histamine receptors. Interaction of histamine with receptors on blood vessels causes increased leakiness, leading to the fluid collection, swelling and increased redness. Histamine also stimulates pain receptors, making tissue more sensitive and irritable. Symptoms last from one to several hours following contact.

In the upper airways and eyes, immediate hyper-sensitivity reactions cause the runny nose and itchy, bloodshot eyes typical of allergic rhinitis. In the gastrointestinal tract, these reactions lead to swelling and irritation of the intestinal lining, which causes the cramping and diarrhea typical of food allergy. Allergens that enter the circulation may cause hives, angioedema, anaphylaxis, or atopic dermatitis.

Allergens on the skin usually cause delayed hypersensitivity reaction. Roving T cells contact the allergen, setting in motion a more prolonged immune response. This type of allergic response may develop over several days following contact with the allergen, and symptoms may persist for a week or more.

Allergens enter the body through four main routes: the airways, the skin, the gastrointestinal tract, and the circulatory system. Airborne allergens cause the sneezing, runny nose, and itchy, bloodshot eyes of hay fever (allergic rhinitis). Airborne allergens can also affect the lining of the lungs, causing asthma, or conjunctivitis (pink eye). Exposure to cockroach allergens has been associated with the development of asthma. Airborne allergens from household pets are another common source of environmental exposure. Allergens in food can cause itching and swelling of the lips and throat, cramps, and diarrhea. When absorbed into the bloodstream, they may cause hives (urticaria) or more severe reactions involving recurrent, non-inflammatory swelling of the skin, mucous membranes, organs, and brain (angioedema). Some food allergens may cause anaphylaxis, a potentially life-threatening condition marked by tissue swelling, airway constriction, and drop in blood pressure. Allergies to foods such as cow's milk, eggs, nuts, fish, and legumes (peanuts and soybeans) are common. Allergies to fruits and vegetables may also occur. In contact with the skin, allergens can cause reddening, itching, and blistering, called contact dermatitis. Skin reactions can also occur from allergens introduced through the airways or gastrointestinal tract. This type of reaction is known as atopic dermatitis. Dermatitis may arise from an allergic Dermatitis may arise from an allergic response (such as from poison ivy), or exposure to an irritant causing nonimmune damage to skin cells (such as soap, cold, and chemical agents). Injection of allergens, from insect bites and stings or drug administration, can introduce allergens directly into the circulation, where they may cause system-wide responses (including anaphylaxis), as well as the local ones of swelling and irritation at the injection site.

3. Other Inflammatory and Autoimmune Disease and Disorders

The results in the Examples below demonstrate the use of nanoparticles for lupus therapy and illustrate a mechanism that can be used for therapeutic immunosuppression strategies useful in the treatment of inflammatory diseases or disorders, autoimmune diseases or disorders, inducing or increase graft tolerance, treating graft rejection, and treating allergies and other alignments with symptoms that can be reduced or ameliorated by regulating the activity of T cells, antigen-presenting cells, or combinations thereof.

Representative inflammatory responses or autoimmune diseases that can be detected or assessed for severity include, but are not limited to, rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, *pemphigus vulgaris*, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

Graft Tolerance

These results are also indicative of efficacy in treating graft rejection and allergies. For example, the compositions can be used in the maintenance of transplants, in which drug combinations are desirable to prevent rejection.

The transplanted material can be cells, tissues, organs, limbs, digits or a portion of the body, preferably the human body. The transplants are typically allogenic or xenogenic. Nanolipogels are administered to a subject in an effective amount to reduce or inhibit transplant rejection. Nanolipogels can be administered systemically or locally by any acceptable route of administration. In some embodiments, the nanolipogel particles are administered to a site of transplantation prior to, at the time of, or following transplantation. In one embodiment, the nanolipogel particles are administered to a site of transplantation parenterally, such as by subcutaneous injection.

In other embodiments nanolipogel particles are administered directly to cells, tissue or organ to be transplanted ex vivo. In one embodiment, the transplant material is contacted with nanolipogel particles prior to transplantation, after transplantion, or both.

In other embodiments nanolipogel particles are administered to immune tissues or organs, such as lymph nodes or the spleen.

The transplant material can be treated with enzymes or other materials that remove cell surface proteins, carbohydrates, or lipids that are known or suspected in being involved with immune responses such as transplant rejection.

a. Cells

Populations of any types of cells can be transplanted into a subject. The cells can be homogenous or heterogeneous. Heterogeneous means the cell population contains more than one type of cell. Exemplary cells include progenitor cells such as stem cells and pluripotent cells which can be harvested from a donor and transplanted into a subject. The cells are optionally treated prior to transplantation as mention above.

Ex vivo methods of nucleic acid delivery can include, for example, the steps of harvesting cells from a subject, culturing the cells, transducing them with an expression vector using nanolipogel particles, and maintaining the cells under conditions suitable for expression of the encoded polypeptides. These methods are known in the art of molecular biology.

b. Tissues

Any tissue can be used as a transplant. Exemplary tissues include skin, adipose tissue, cardiovascular tissue such as veins, arteries, capularies, valves; neural tissue, bone marrow, pulmonary tissue, ocular tissue such as corneas and lens, cartilage, bone, and mucosal tissue. The tissue can be modified as discussed above.

c. Organs

Exemplary organs that can be used for transplant include, but are not limited to kidney, liver, heart, spleen, bladder, lung, stomach, eye, tongue, pancreas, intestine, etc. The organ to be transplanted can also be modified prior to transplantation as discussed above.

One embodiment provides a method of inhibiting or reducing chronic transplant rejection in a subject by administering an effective amount of nanolipogel particles to inhibit or reduce chronic transplant rejection relative to a control.

5. Graft-Versus-Host Disease (GVHD)

Nanolipogel particles can also be used to treat graft-versus-host disease (GVHD) by administering an effective amount of nanolipogel particles including an active agent to alleviate one or more symptoms associated with GVHD. GVHD is a major complication associated with allogeneic hematopoietic stem cell transplantation in which functional immune cells in the transplanted marrow recognize the recipient as "foreign" and mount an immunologic attack. It can also take place in a blood transfusion under certain circumstances. Symptoms of GVD include skin rash or change in skin color or texture, diarrhea, nausea, abnormal liver function, yellowing of the skin, increased susceptibility to infection, dry, irritated eyes, and sensitive or dry mouth.

6. Diabetes

The nanolipogel particles can also be used to treat diabetes. The method includes transplanting insulin producing cells in a subject and administering to the subject an effective amount of nanolipogel particles including an active agent to reduce or inhibit transplant rejection. In another method, the pancreatic islet antigens can be encapsulated together with a tolerogenic agent and used as to induce tolerance against the insulin producing cells. Preferably the insulin producing cells are beta cells or islet cells. In certain embodiments, the insulin producing cells are recombinant cells engineered to produce insulin.

The insulin producing cells can be encapsulated within a matrix, such as a polymeric matrix, using suitable polymers, including, but not limited to alginate, agarose, hyaluronic acid, collagen, synthetic monomers, albumin, fibrinogen, fibronectin, vitronectin, laminin, dextran, dextran sulfate, chondroitin sulfate, dermatan sulfate, keratan sulfate, chitin, chitosan, heparan, heparan sulfate, or a combination thereof.

D. Exemplary Disease Treatment Strategies

Exemplary therapies and strategies of autoimmune diseases and other inflammatory conditions are outlined in Table I below. The table presents a pathological aberrance that is addressed by the therapy; the cells target(s) of the therapy; one, two, or three therapeutic molecules that can be delivered by the nanolipogels alone or in any combination thereof; a desired target or targeting moiety can be used to target the nanoliposomes; the preferred delivery mechanism; and intended effects of the therapy.

TABLE 1

Exemplary Therapies and Strategies for Treating Inflammatory and Autoimmune Diseases and Disorders

| Disease | Pathological Abberrance | Cell Target(s) | Delivered Molecule (DM) 1: | DM 2: | DM 3: | Targeting Strategy | Delivery Mechanism | Effect |
|---|---|---|---|---|---|---|---|---|
| Autoimmunity (i.e., type 1 diabetes, arthritis, food allergy, encephalitis, Crohn's IBD) | inflammatory response against self Ag | Antigen Presenting Cells (APCs) | plasmid for tolerogenic cytokine such as IL-10 | self-antigen (collagen, insulin, etc) | | | | create antigen-specific, tolerogenic APCs that amplify tolerance |
| Graft vs. Host Disease | T cells reacting against graft | T cells (naïve) | Foxp3 plasmid | tolerogenic drug like rapamycin | protein, peptide, something Ag-specific | anti-CD7 for human | | change inflammatory T cells to Ag-specific, tolerogenic type |
| Malaria | parasite infects RBCs | infected RBCs | plasmid DNA | more plasmid DNA | | | Choukri Mamoun plasmids | transform parasite, identify drug resistant infected RBCs |

TABLE 1-continued

Exemplary Therapies and Strategies for Treating Inflammatory and Autoimmune Diseases and Disorders

| Disease | Pathological Abberrance | Cell Target(s) | Delivered Molecule (DM) 1: | DM 2: | DM 3: | Targeting Strategy | Delivery Mechanism | Effect |
|---|---|---|---|---|---|---|---|---|
| Leishmania | parasite lives in macrophages | infected macrophages | myriad small molecule drugs | excess dendrimer to help break endosome | | mannose, Fc fragment, etc | | expel parasite from endolysosome, kill it |
| Arthritis | immune system is reactive against collagen | APCs | HDACi | collogen autoantigen | maybe tolerogenic drug | | | abrogate autoimmune environment |
| Th-2-cell mediated inflammatory disease | Th2-committed cells are hijacked by different pathogens | at-risk T cells | HDACi for prescribed transcription factors | | | | | |
| Th17-mediated diseases | Th17 cells | Th17 cells | HDACi against outlined targets | siRNA against outlined targets | | | | |

The present invention will be further understood by reference to the following non-limiting examples.

Example 1

Preparation of Nanolipogels for Delivery of Anti-Tumor Molecules

Materials and Methods
Nanolipogel Synthesis.

Figure 1B:
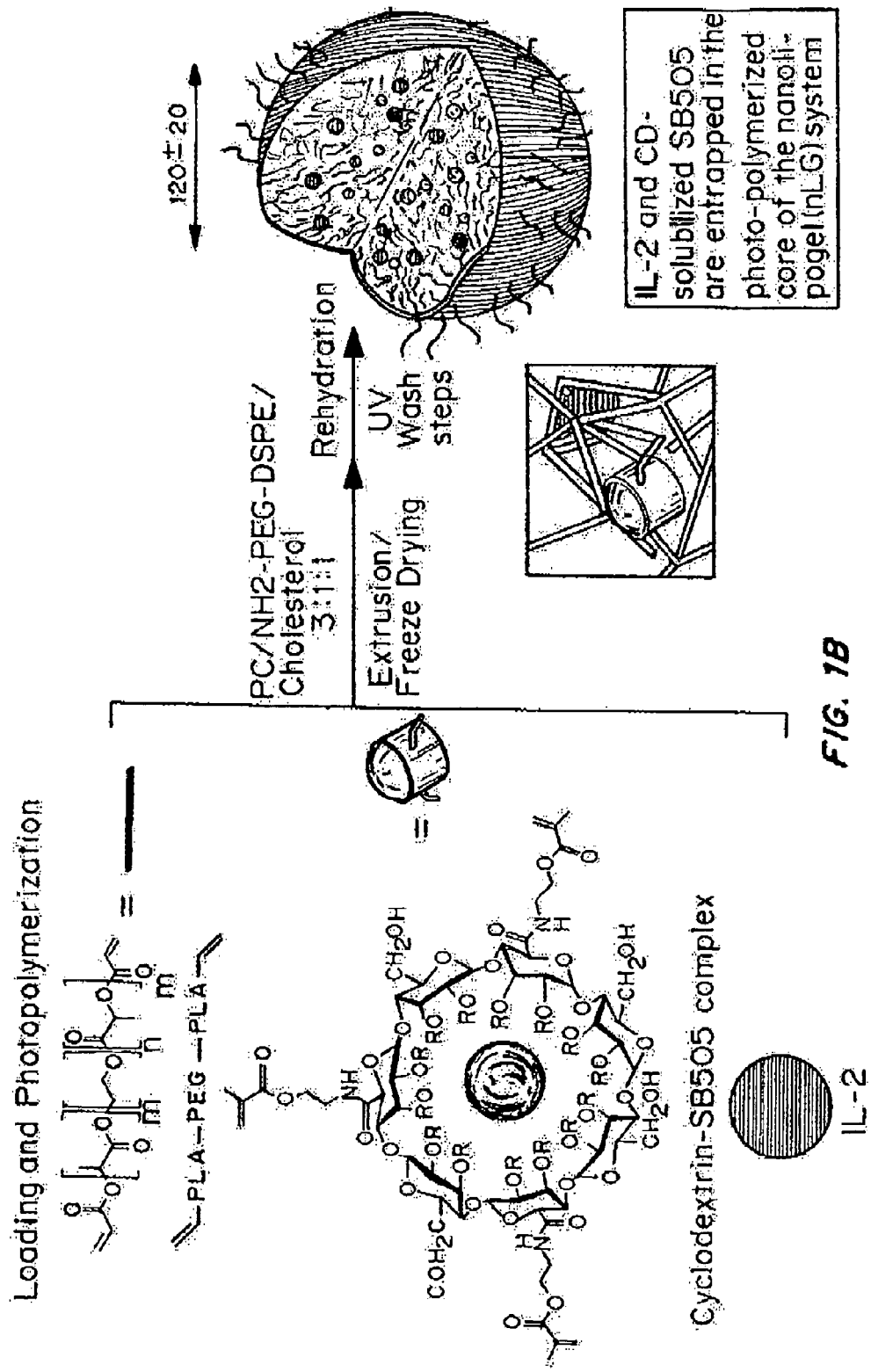
Figure 1C:
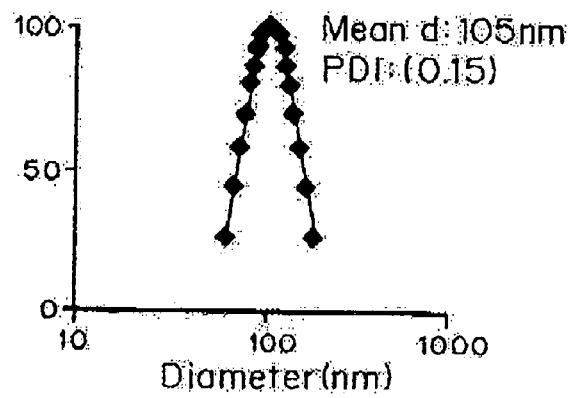
Figure 1C:
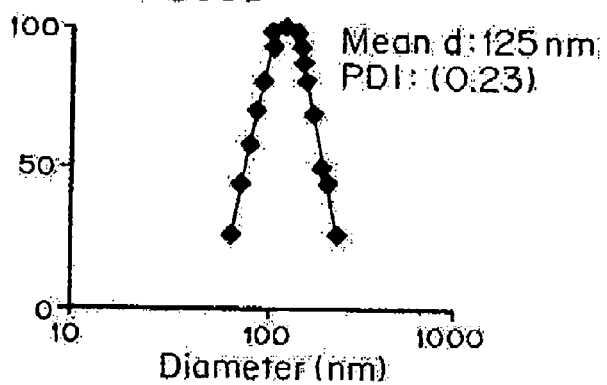
Figure 1C:
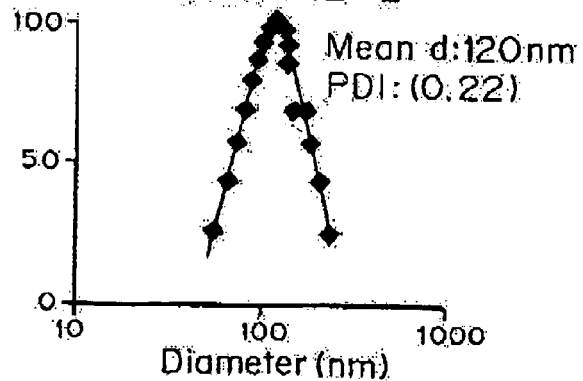

"Nanolipogel" (sometimes referred to as "nLG") particles due to its nature as a lipid bilayer surrounding a hydrogel core was fabricated from a degradable polymer (FIG. 1B). Liposomes were used as nanoscale molds for photo-initiated hydrogel formation. To achieve sustained release of the hydrophobic drug in conjunction with encapsulated proteins, methacrylate-conjugated β-cyclodextrins (CDs) were incorporated into the interior of the liposomes. β-cyclodextrins have a long history as solublization agents for hydrophobic compounds and are key excipients in various pharmaceutical formulations. This formulation procedure enabled co-encapsulation of both proteins as well as small hydrophobic drugs within the interior of the lipid bilayer (FIG. 1A-1B).

Conjugated CDs were created by reaction of succinylated-CDs with photosensitive methacrylate groups through hydrolysable ester groups. (FIG. 1A) Complexation of SB or rhodamine (for imaging) with functionalized CD was verified by proton nuclear magnetic resonance ($^1$H NMR) on a 500 MHz Bruker spectrometer. All samples were dissolved in 1-10 mg/ml in D$_2$O for characterization with the solvent as a reference.

PLA-PEG-PLA diacrylate was synthesized in two steps according to Sawhney, et al. *Macromole* 26, 581-587 (1993). All chemicals were purchased from Sigma unless otherwise noted and were of ACS grade or higher. α,ω-dihydroxy poly(ethylene oxide) with a molecular weight of 4000 g/mol, 3,6-dimethyl-1,4-dioxane-2,5-dione (dl-lactide), and tin(II) 2-ethylhexanoate (stannous octoate) were charged into a round-bottom flask under nitrogen in a 5:1:0.0075 mol ratio and the reaction was stirred under vacuum at 200° C. for 4 hours, followed by stirring at 160° C. for 2 hours. After cooling to room temperature, the resulting copolymer was dissolved in dichloromethane and precipitated in anhydrous ether. This intermediate was dissolved in dichloromethane (10 g/mL) and cooled to 0° C. in an ice bath. Per 10 g of polymer intermediate, 440 μL triethylamine and 530 μL acryloyl chloride were added under nitrogen and the reaction mixture was stirred for 12 hours at 0° C. and 12 hours at room temperature. The mixture was filtered and the resulting polymer was precipitated in diethyl ether. The final polymer was redissolved in dichloromethane, re-precipitated in hexanes and characterized by FTIR and NMR.

The complexation of Rhodamine and SB505124 with cyclodextrins was examined by proton nuclear magnetic resonance ($^1$H NMR) spectroscopy on a 500 MHz Bruker spectrometer.

Nanolipogel Formulation.

All lipids were obtained from Avanti Polar Lipids and used without further preparation. Phosphatidyl choline (PC), 1,2-distearoyl-sn-glycero-3-phosphoethanolamine-N-[amino(polyethylene glycol)-2000] (DSPE-PEG), and cholesterol were mixed in chloroform in a 3:1:1 molar ratio and liposomes were formulated using a remote loading technique of Peer, et al. *Science* 319, 627-630 (2008). Lipid-labeled fluorescent liposomes were formulated by incorporation of 10% 1,2-distearoyl-sn-glycero-3-phosphoethanolamine-N-[poly(ethylene glycol)2000-N'-carboxyfluorescein] (DSPE-PEG-Fluorescein). Briefly, the dissolved lipids were mixed in a glass scintillation vial, followed by complete solvent removal with a directed nitrogen stream. This formed a thin lipid film on the inner glass surfaces, which was rehydrated by the addition of 1× phosphate buffered saline (PBS). Cycles of thirty second vortexing followed by 5 min idle sitting at room temperature were repeated ten times and the resulting multilamellar liposomes were extruded 10 times through a 5 μm polycarbonate membrane (Whatman), 10 times through a 1 μm membrane and finally 11 times through a 100 nm using a LIPEX extruder (Northern Lipids, Inc.). The resulting unilamellar liposomes were then frozen and lyophilized.

Lyophilized liposomes were reconstituted with a solution containing 5% (w/v) polymer (FIG. 1B) and 2.5 mg/mL Ciba Irgacure 2959 as the photoinitiator and: no other additive (nLG-Empty), 9 mg f-CD-solubilized SB/100 mg nLG (nLG-SB; SB505124, Sigma), 1 μg IL-2/100 mg lipids (LG-IL-2; Aldesleukin Proleukin, Novartis), or both f-CD-solubilized SB and IL-2 (nLG-SB+IL-2). CD (randomly succinylated β-CD; CTD, Inc.) was functionalized with 2-aminoethyl methacrylate by stirring a 1:3 molar ratio of the compounds in 1×PBS for 1 hour at room temperature. SB was incorporated into f-CD by adding the drug dissolved in methanol to the f-CD. After 20 minutes of vigorous stirring at room temperature to form the complexes, the methanol was evaporated with a directed stream of nitrogen. The reconstitution step proceeded with 30 minutes of vortexing to rehydrate the liposomes. The liposomes were then irradiated under UV light for 8 minutes with a Blak-Ray long wave ultraviolet lamp (Model B 100) at a 10 cm working distance. Directly prior to UV irradiation, the samples were diluted fivefold to prevent macroscale gellation. The resulting nanolipogels were pelleted by centrifugation (five minutes at 7200 rcf) and resuspended in 1×PBS. This centrifugation/resuspension procedure was repeated three times. Nanolipogels were aliquotted and frozen at −20° C. until further use. For consistency, all nanolipogels were frozen prior to use (in vitro or in vivo). Final size and dispersity was confirmed by resuspending nanolipogels in 1×PBS for analysis on a ZetaPALS dynamic light scattering instrument. The zeta potential of PC/cholesterol liposomes, PC/cholesterol/PE-PEG-NH$_2$ liposomes, and nanolipogels were evaluated in 0.1×PBS using a Malvern nanosizer.

For TEM analysis, nanolipogel samples were stained with osmium tetroxide and then imaged on an FEI Tenai Biotwin microscope. Lipid-specific osmium tetroxide staining of cryosectioned samples had a localized staining pattern confined to the exterior membrane of the particle.

Results

Liposomes were used as nanoscale molds for photo-initiated hydrogel formation. To achieve sustained release of the hydrophobic drug in conjunction with encapsulated proteins, methacrylate-conjugated β-cyclodextrins (CDs) were incorporated into the interior of the liposomes. β-cyclodextrins have a long history as solublization agents for hydrophobic compounds and are key excipients in various pharmaceutical formulations.

Complexation of SB or rhodamine (for imaging) with functionalized CD was verified using $^1$H NMR. The functionalized CD (f-CD) becomes covalently bound to the liposome-encapsulated polymer matrix during photo-induced polymerization, thus the SB can only be released upon f-CD/SB hydrolysis of the polymer ester groups and subsequent diffusion out of the nanolipogel, enabling sustained release compared to the burst-dominated release of SB in the absence of gelled CD. This system enabled control over the release of remotely loaded IL-2 without compromising its bioactivity and enabled simultaneous release of both protein and drug compared to single component release. The release profile of SB/IL-2-loaded nanolipogels was not altered by incubation in serum and release was substantively completed by 7 days.

To demonstrate the impact of polymerization in the nLG on the release profile of SB and IL-2, release kinetics of both agents were compared with release from liposomes and solid poly(lactide-co-glycolide) nanoparticles (PLGA NPs) encapsulating both agents. Incorporation of photocured polymer in the nanolipogel vehicle enabled a more sustained release of SB compared to liposomes and a more complete release compared to conventional 50:50 (PLGA NPs) of the same diameter. The release kinetics of the drug is seen to be intermediate between that of diffusion dependent release from liposomes and hydrolysis dependent release from PLGA. Comparative cumulative release of IL-2 from liposomes, nanolipogels, and PLGA NPs demonstrated that encapsulation of IL-2 in nanolipogels enabled better sustained release of cytokine.

The bioactivity of the SB and IL-2 were unaffected by lipogel incorporation. Encapsulation of IL-2 (80%) and/or drug (36%) did not significantly affect nanolipogel diameter; dynamic light scattering analysis revealed a mean diameter of 120 nm and polydispersity index of 0.2. Liposomes and nanolipogels incorporating amine-terminated PEGylated phosphatidyl ethanolamine demonstrated a neutral zeta potential, compared to the approximately −22±10 mV zeta potential of liposomes formulated with only phosphatidyl choline and cholesterol. Cryo-TEM of nanolipogels showed the formation of spherical liposomal structures, detectable by light scattering even after disruption of the liposomal exterior by detergent, validating an inner gel core with approximately the same diameter as the intact nanolipogel. The in vitro cytotoxicity of this system was negligible.

To investigate the biodistribution and clearance of this platform, CD-solubilized rhodamine was used as a fluorescent surrogate marker model for SB; rhodamine complexation with CD had been previously used to qualify guest-host interactions with CDs. This was confirmed here by $^1$H NMR.

Figure 1D:
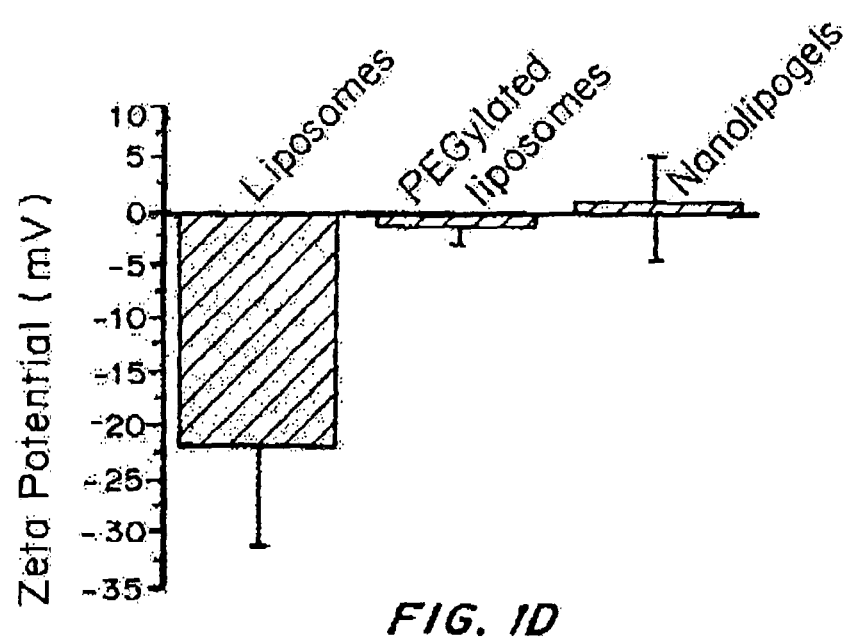
Figure 1F:
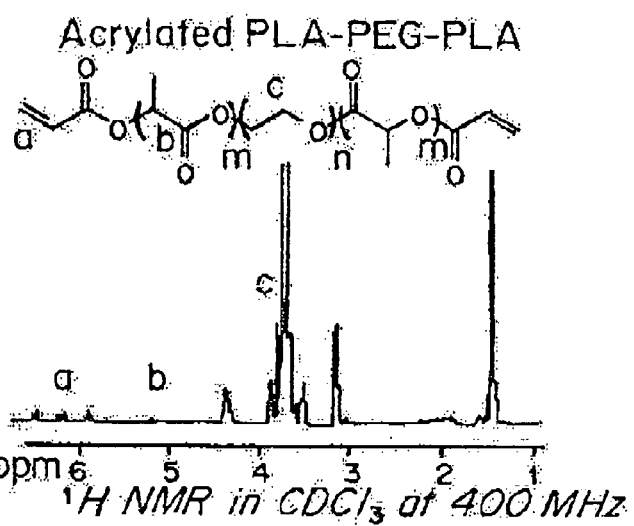
Figure 1G:
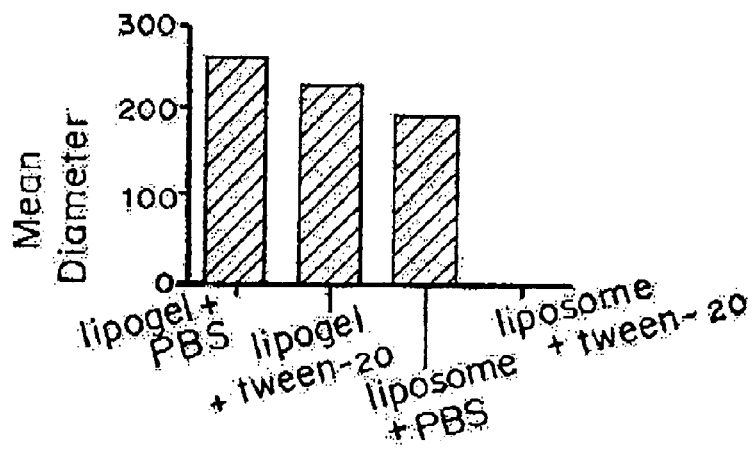

Encapsulation of SB or SB+IL-2 had no significant effect on particle mean diameter or polydispersity. FIG. 1D shows that the zeta potential of liposomes and nanolipogels incorporating amine-terminated PE-PEG was found to be close to neutral. FIG. 1E shows the composition and formulation properties of the nanolipogel formulation. FIG. 1F shows the polymer structure verified by $^1$H NMR. Cryo-TEM of nanolipogels demonstrated the formation of spherical liposomal structures. FIG. 1G shows that the photopolymerized polymer/CD forms nanoparticulate hydrogel structures that are detectable by light scattering even after disruption of the liposomal exterior by detergent.

Example 2

In Vitro Release and Bioactivity Studies

Materials and Methods
Controlled Release Studies.

To demonstrate the advantage of nanolipogel vehicles for controlled release of encapsulated agents over prolonged periods of time, a series of studies were conducted to evaluate in vitro release of nanolipogel particles containing SB and/or IL-2. Release studies were performed at 37° C. with constant agitation in 1×PBS+10% fetal bovine serum. At each time point the complete volume was removed and replaced with fresh buffer after centrifugation (five minutes at 7200 rcf). Nanolipogels were resuspended by manual pipetting. Absorbance measurements to determine SB concentrations were performed with a Beckman Coulter plate reader at 300 nm. Absorbance readings from nLG-Empty particles were subtracted from those obtained from nLG-SB particles to ensure readings were due only to encapsulated SB. IL-2 release was determined using an IL-2 ELISA kit (BD Biosciences) with humanized capture (BD, 555051) and biotinylated-detection (BD, 555040) antibodies according to the manufacturer's instructions. For IL-2 used in these studies, the international unit conversion was 22 MU=1.3 mg.

The functionalized CD (f-CD) becomes covalently bound to the liposome-encapsulated polymer matrix during photo-induced polymerization, thus the SB can only be released upon f-CD/SB hydrolysis of the polymer ester groups and subsequent diffusion out of the nanolipogel, enabling sustained release compared to the burst-dominated release of SB in the absence of gelled CD.

Bioactivity Studies.

Cumulative release of nLG-IL-2 was performed at 1, 3, 5, and 7 days in complete media [RPMI media (Gibco) with 10% fetal bovine serum (Atlanta Biological) and penicillin/streptomycin (Sigma) supplemented with L-glutamine (Sigma), non-essential amino acids (Gibco), Hepes buffer (Sigma), gentamicin (Sigma), and β-mercaptoethanol (Sigma)]. Splenocytes were isolated from a B6 mouse and $1 \times 10^6$ cells were added in 500 µL T cell media to each well of a 24 well plate previously coated with 10 µg/mL anti-CD3 (coated overnight in 1×PBS at 4° C.) and 5 µg/mL soluble anti-CD28 (BD Biosciences). The media from release studies was filtered through a 0.22-µm syringe filter (Whatman) and 500 µL was added to the wells. Additionally all wells contained 5 µg/mL soluble anti-CD28 (BD Biosciences). Soluble IL-2 was added at varying concentrations to control wells to as a standard. Cells were incubated at 37° C. and cellular stimulation was assessed after 72 hours using an IFN-γ ELISA (BD Biosciences).

Results

Figure 2A:
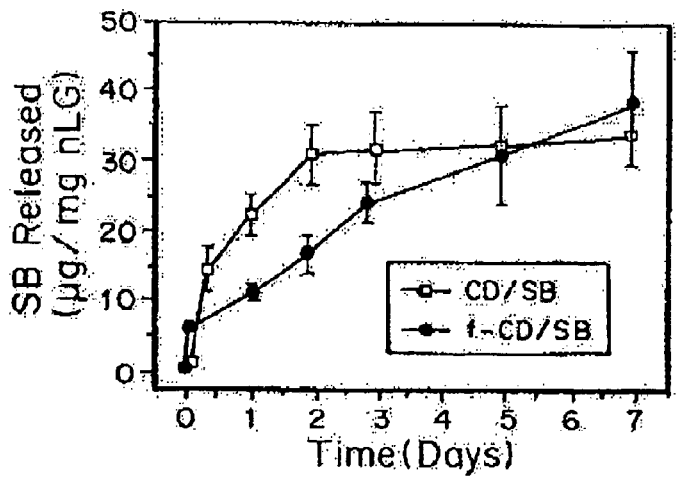
Figure 2B:
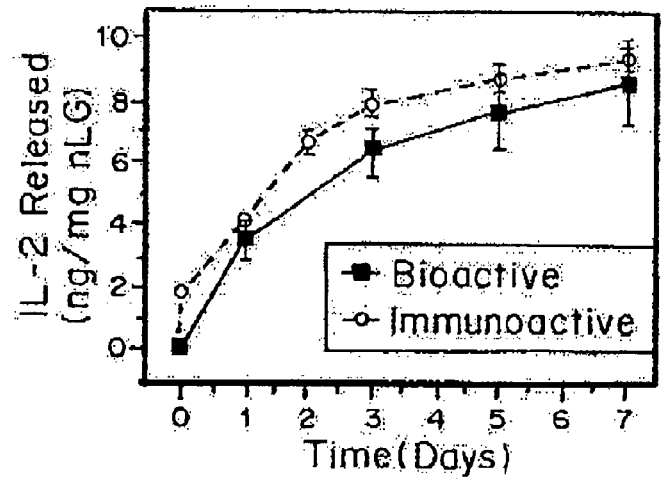
Figure 2C:
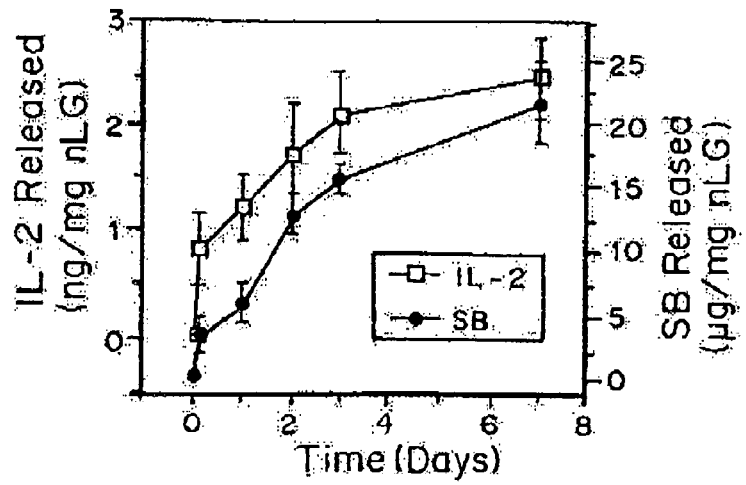

FIGS. 2A-2E are comparative release profiles from nLG, lipsomes and solid polymer nanoparticles (PLGA). Cumulative CD- or methacrylate functionalized-CD (f-CD)-solubilized SB released from nLGs normalized by initial carrier mass demonstrated that polymerization of nanolipogels improved the sustained nature of SB release (FIG. 2A). Hydroxypropyl β-CD was used for SB complexation with the unfunctionalized CD. Cumulative IL-2 released determined by ELISA (immunoactive) and by a bioactivity study (bioactive) from nLGs normalized by initial nanolipogel mass demonstrated that bioactivity of IL-2 was unaffected by encapsulation (FIG. 2B). Release of SB and IL-2 was not affected by incubation of 10 mg nLG in 1 ml full serum (FIG. 2C). Comparative cumulative release of SB from liposomes, nanolipogels, and degradable polymeric (poly lactide-co-glycolide) nanoparticles (PLGA NPs) demonstrated that incorporation of photo-cured polymer in the nanolipogel vehicle enabled better sustained release and more complete release of cyclodextrin-solubilized SB (FIG. 2D). PLGA NPs (mean diameter=150±50 nm) were prepared by using a modified water/oil/water double emulsion technique. Liposomes were prepared in an identical manner as the nLG without the polymer core. Liposomes were loaded with IL-2 and SB similar to nanolipogels. The diminished percent of encapsulated SB released from PLGA NPs is attributed to the interaction of the relatively hydrophobic polymer with SB. All particulate formulations were dissolved in 0.1N NaOH+1% SDS to determine 100% release at 7 days (arrow) (FIG. 2D). Comparative cumulative release of IL-2 from liposomes, nanolipogels, and PLGA NPs demonstrated that encapsulation of IL-2 in nanolipogels enabled better sustained release of cytokine Cumulative release is presented as % of total IL-2 released through 7 days. (FIG. 2E) Data in all graphs represent mean of triplicate samples±1 standard deviation. FIG. 2F compares the sizes and loading of IL-2 and SB in PLGA, nanolipogels and liposomes.

This system enabled control over the release of remotely loaded IL-2 without compromising its bioactivity. Loading of IL-2 in the polymer hydrogel space outside of the CD enabled simultaneous release of both protein and drug. The decreased total release of both components (FIG. 2C) compared to single component release was likely due to steric limitations within the interior of the nanolipogel or decreased loading efficiency of SB and IL-2. The release profile of SB/IL-2-loaded nanolipogels was not altered by incubation in serum and release was substantively completed by 7 days.

To demonstrate the impact of polymerization in the nanolipogel on the release profile of SB and IL-2 the release kinetics of both agents were compared with release from liposomes and solid poly(lactide-co-glycolide) nanoparticles (PLGA NPs) encapsulating both agents. Incorporation of photocured polymer in the nanolipogel vehicle enabled a more sustained release of SB compared to liposomes and a more complete release compared to conventional 50:50 (PLGA NPs) of the same diameter. The release kinetics of the drug is seen to be intermediate between that of diffusion-dependent release from liposomes and hydrolysis-dependent release from PLGA. Comparative cumulative release of IL-2 from liposomes, nanolipogels, and PLGA NPs demonstrated that encapsulation of IL-2 in nanolipogels enabled better sustained release of cytokine.

Bioactivity.

Nanolipogel vehicles provide the wherewithal to control release of encapsulated agents without compromising bioactivity. The bioactivity of the SB and IL-2 were unaffected by lipogel incorporation. IFN-γ production was correlated with IL-2 concentration to determine bioactivity.

Example 3

Characterization of Nanolipogels

Encapsulation of IL-2 (80%) and/or drug (36%) did not significantly affect nanolipogel diameter; dynamic light scattering analysis revealed a mean diameter of 120 nm and polydispersity index of 0.2. Liposomes and nanolipogels incorporating amine-terminated PEGylated phosphatidyl ethanolamine demonstrated a neutral zeta potential, compared to the −22±10 mV zeta potential of liposomes formulated with only phosphatidyl choline and cholesterol. Cryo-TEM of nanolipogels showed the formation of spherical liposomal structures, detectable by light scattering even after disruption of the liposomal exterior by detergent, validating an inner gel core with approximately the same diameter as the intact nanolipogel. The in vitro cytotoxicity of this system was negligible.

Example 4

Biodistribution

To investigate the biodistribution and clearance of this platform, CD-solubilized rhodamine was as a fluorescent surrogate marker model for SB; rhodamine complexation with CD had been previously used to qualify guest-host interactions with CDs. This was confirmed by $^1$H NMR. The in vivo pharmacokinetics of rhodamine following systemic administration was evaluated in healthy mice receiving a single intravenous administration of nLG-rhod, an equivalent dose of free rhodamine, or PBS control via tail vein injection.

Results

Spectrofluorometric analysis of rhodamine extracted from blood showed 15.7±4.1% and 7.7±3.7% (mean±s.d.) of the initial dose of nanolipogel remaining at 1 and 24 hours respectively post-injection. Free rhodamine was rapidly cleared and was not detectable in blood at any of the time points taken following injection.

Figure 3A:
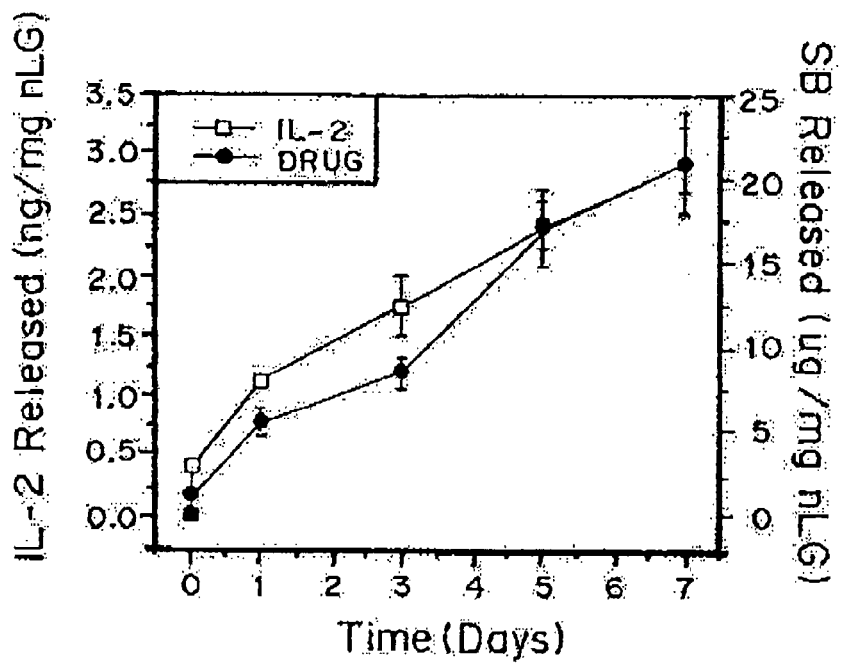
Figure 3B:
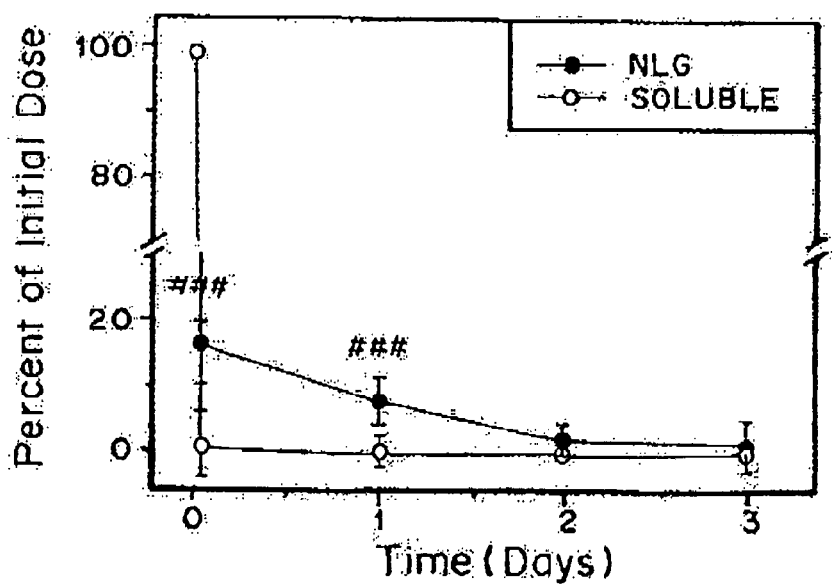
Figure 3C:
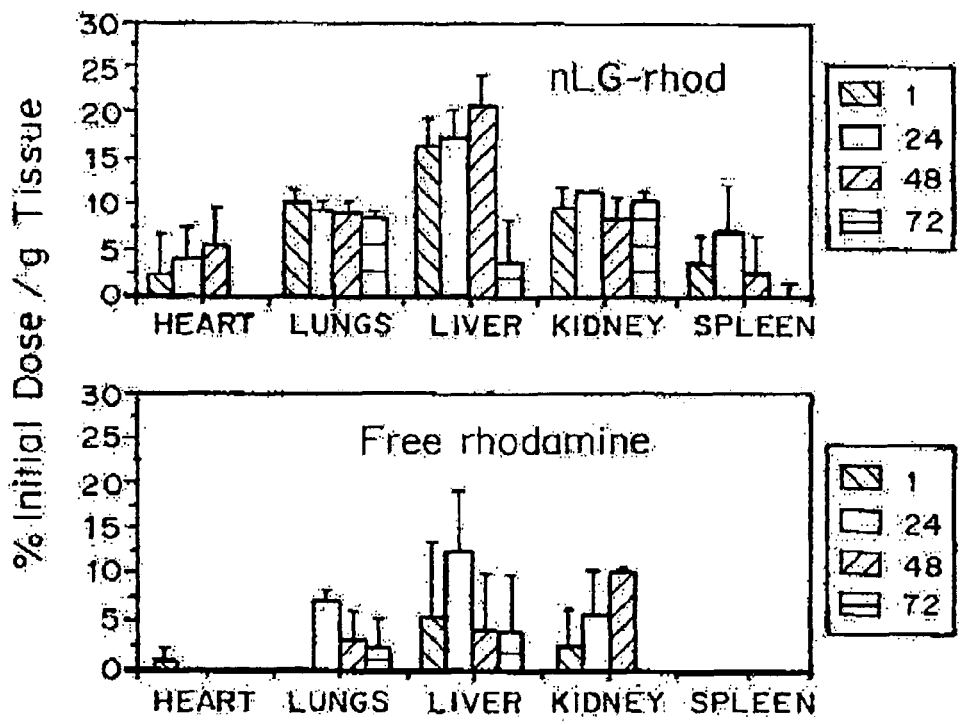

FIGS. 3A-3G are graphs showing controlled release, clearance, and biodistribution. The distribution of both nanolipogel carrier and encapsulated drug payload was investigated using dual-labeled NLG; fluorescein-labeled phosphoethanolamine was incorporated into the lipid component of rhodamine-loaded nanolipogels. Spectrofluorimetric analysis at 540/625 nm and 490/517 nm show dose-dependent fluorescence with no spectral overlap. FIG. 3A is a graph of cumulative IL-2 (ng/mg nLG) and drug (µg SB/mg nLG) released from co-loaded nLGs normalized by carrier mass. Error bars in all plots represent ±1 standard deviation. FIG. 3B is a graph showing clearance (percent of initial dose) of drug dose over time in days: Encapsulation in nanolipogels significantly increased the remaining percentage of initial dose in the blood at 1 and 24 hours post-injection (two population t test, p<0.01 ###). FIG. 3C is a graph of whole body distribution. Mice received a single dose of rhodamine-loaded nanolipogel or soluble rhodamine (in saline) via intravenous tail vein injection. Animals were sacrificed at 1, 24, 48, and 72 hours post-injection for extraction and quantification of fluorescence.

Figure 3D:
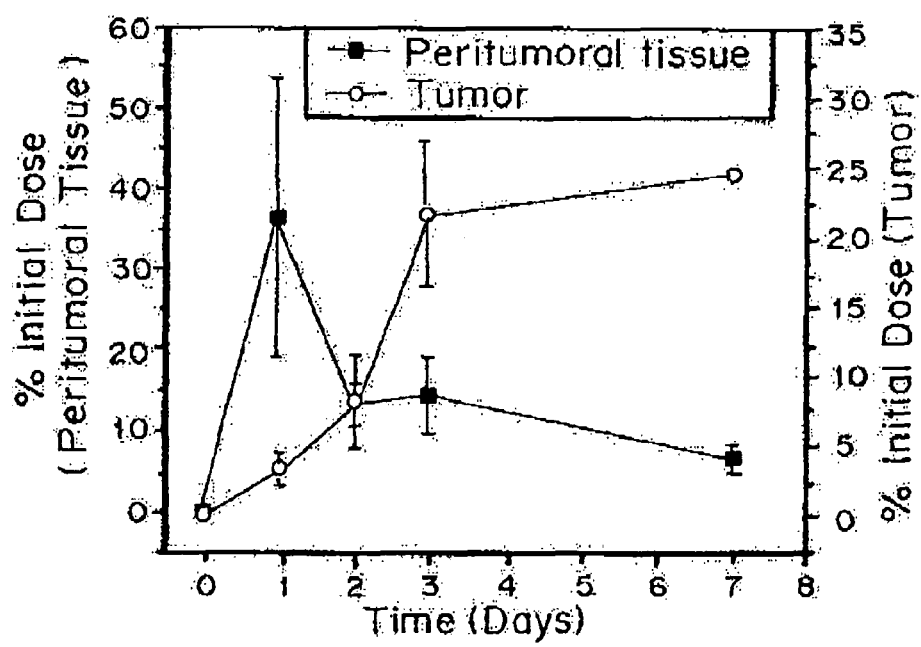

Whole body biodistribution was determined with rhodamine labeling. Significantly higher (two population t test, p<0.01) amounts of rhodamine were detected in the major organs of nanolipogel-treated animals compared to animals injected with free dye. FIG. 3D is a graph of time dependent accumulation in subcutaneous tumor, showing cumulative rhodamine tumor penetration (circles) after B16 peritumoral injection in B6 mice. Peritumoral tissue was collected to quantify the remaining dose of nLG surrounding the tumor (squares). Controlled release demonstrates release of rhodamine, but not lipid (FIG. 3E). Mice bearing subcutaneous B16 tumors received a single IV (tail vein) injection of dual-labeled NLG. Animals were sacrificed at 1, 2, 3, and 7 days post injection and tissues collected for homogenization, extraction, and quantification of rhodamine and fluorescein-PE. Analysis of serum showing prolonged circulation of both encapsulant and delivery vehicle. Similar patterns of biodistribution were observed between lipid (FIG. 3F) and drug payload (FIG. 3G), with highest accumulations of drug occurring in the lungs and liver.

Analysis of the biodistribution to major organs showed that the lungs, liver and kidney were primary sites of accumulation of both nanolipogel-encapsulated rhodamine and free rhodamine. Encapsulation in nanolipogel increased both the total initial dose to most tissues as well as the cumulative dose over three days.

Example 5

Cytotoxic and Safety Studies

Materials and Methods

Cell titer blue (Invitrogen) was used as a cell viability marker according to the manufacturer's instructions. Chinese Hamster Ovary (CHO) cells (ATCC) were placed in 96 well plates at a density of $5 \times 10^4$ cells/well (except the standard, which contained a serial dilution of the number of cells). Cells were incubated for 24 hours at 37° C. with serial dilutions of 1×PBS (positive control), sodium azide (negative control; Sigma), liposomes, or nanolipogels. Liposomes were fabricated similarly to nanolipogels but, after lyophilization, were reconstituted with pure 1×PBS and were not subjected to UV irradiation. Nanolipogels were from the nLG-Empty group. After 24 hours the cell titer blue reagent was added (20 µL/100 µL volume). The cells were further incubated for 4 hours at 37° C., after which they were pelleted and the fluorescence of the supernatant was measured. 100% cell survival is defined as the average of survival from the 1×PBS group and 0% survival that from the azide group. All samples were run in triplicate and the experiment was repeated three times with similar results.

To examine the in vivo safety of nanolipogel particles, C57/Bl6 mice were administered a single intravenous dose of nanolipogels and acute toxicology was measured 7 days later. Lung toxicity was evaluated by histology to determine if systemically administered nanolipogels induced any acute inflammation.

Results

No statistically significant toxic effects were observed from the administration of empty nanolipogels or nanolipogels co-encapsulated with SB505124 (SB) or IL-2. No hepatotoxicity was observed, as measured by serum levels of alkaline phosphatase and alanine aminotransferase. Normal physiological reference ranges given by the IDEXX VetTest® system for mouse alkaline phosphatase and alanine aminotransferase were 62-209 IU/L and 28-132 IU/L, respectively. Furthermore, no renal toxicity was observed, as blood urea nitrogen levels were within the normal mouse reference range of 18-29 mg/dL. A complete blood count was also performed to identify any hematological toxicity. Leukocyte counts, platelet counts, and hemoglobin content were all within normal physiological ranges for mouse (leukocytes: $1.8-10.7 \times 10^3$ cells/uL; platelets: $592-2971 \times 10^3$ cells/uL; hemoglobin: 11.0-15.1 g/dL). Hematoxylin and eosin staining of lungs demonstrated no obvious pulmonary toxicity. Bronchiolar and alveolar structures appeared normal, and no disruption to epithelial layers or inflammatory infiltrates were observed in lung sections.

The in vitro results demonstrate that nanolipogels have similar negligible toxicities to liposomes.

Healthy C57/B16 mice were administered a single intravenous dose of nanoparticle combination therapy or controls and acute toxicology measured 7 days later. No significant toxicities were observed in serum measurements of alkaline phosphatase or serum alanine aminotransferase. Normal physiological ranges for mouse alkaline phosphatase are approximately 62-209 IU/L and for alanine aminotransferase approximately 28-132 IU/L. No renal toxicity was observed, as blood urea nitrogen levels were within the normal mouse reference range of 18-29 mg/dL. Complete blood counts demonstrated that normal physiological ranges leukocyte counts, platelet counts, and hemoglobin content. Lung toxicity was evaluated by histology to determine presence of acute inflammation. Hematoxylin and eosin staining of lungs demonstrated no obvious pulmonary toxicity or inflammatory infiltrates; bronchiolar and alveolar structures appeared normal with no disruption to epithelial layers.

Example 6

Comparative Distribution of Nanolipogel Carrier and Encapsulant

Materials and Methods

The distribution of both nanolipogel carrier and encapsulated drug payload was investigated using dual-labeled nanolipogels. Fluorescein-labeled phosphoethanolamine was incorporated into the lipid component of rhodamine-loaded nanolipogels. Spectrofluorimetric analysis at 540/625 nm and 490/517 nm demonstrated a dose-dependent fluorescence with no spectral overlap. There was controlled release of rhodamine, but not lipid.

Mice bearing subcutaneous B16 tumors received a single IV (tail vein) injection of dual-labeled NLG. Animals were sacrificed at 1, 2, 3, and 7 days post injection and tissues collected for homogenization, extraction, and quantification of rhodamine and fluorescein-PE.

Results

Analysis of serum showed prolonged circulation of both encapsulant and delivery vehicle. Similar patterns of biodistribution were observed between lipid and drug payload, with highest accumulations of drug occurring in the lungs and liver.

Example 7

Lipid Encapsulated Dendrimers for Combined Delivery of Nucleic Acids, Proteins, and Drugs The nanolipogel encapsulates a dendrimer. The main shell is a liposome encapsulating a drug and siRNA/dendrimer complex which inserts in cells. Dendritic polymers (dendrimers) are a class of monodisperse polymers distinguished by their repeated branching structure emanating from a central core. This branching, which is inherent in the divergent synthesis of dendrimers, leads to a geometric growth of the polymer that can nearly approximate a sphere with increased branchings or higher generations (generation 6 or above). This branching creates a core ideally suited for entrapment of a variety of small hydrophobic molecules such as drugs as well as complexation of nucleic acids. For example, Superfect®, a commercially available activated dendrimer transfection agent. Combined with their narrow molecular weight distribution and small size (less than 10 nm), dendrimers have been utilized for a large number of applications including drug and gene delivery. Dendrimers complexed with nucleic acids can be cleared rapidly upon in vivo administration and hence protective targeting of this complex would be a more attractive modality for site-specific delivery. The liposomal formulation serves two functions: 1) Protective encapsulation of siRNA complexed liposomes and 2) facilitating delivery of small molecule hydrophilic drugs such as rivoavrin or proteins such as IFNα. Complexation of the inner dendrimer core with siRNA: Nucleic acids are generally stabilized by cationic polymers in a polyplex formation akin to the physiological packaging of nucleic acids around histones. Cationic polyamidoamine (PAMAM) dendrimers, generation 5 (G5) 5.4 nm, serves this purpose.

Materials and Methods siRNA/Dendrimer polyplexes are formed by combining G5 PAMAM and siRNA at an amine to phosphate (N/P) ratio of 1:1 to 10:1. The precise ratio which will yield optimal silencing can be determined by mixing stock siRNA and PAMAM at different molar ratios for 30 min at room temperature in sterile 10 mM HEPES buffer, pH 7.2 with light vortexing. This procedure yields a siRNA-dendrimer polyplex with a charge (zeta potential) of +20 or above and effective diameter of 10 nm, which is suitable for encapsulation in liposomes.

Next, the polyplex is co-encapsulated with the drug (IFNα and/or Ribavirin) in the liposomal particle. A dehydrated lipid film comprised of distearoyl-glycero-phosphocholine (DSPC), cholesterol, and distearoylglycero-phosphoethanolamine (DSPE) with an amine terminated polyethylene glycol (PEG2000) spacer (DSPE-PEG2000-NH2) is first mixed in the molar ratio of 65:30:5, then rehydrated under sonication with a 10 mg/ml solution of siRNA/Dendrimer polyplex and drug. The ratio of drug to siRNA/dendrimer in solution can be tuned during formulation. Optimal ratio is dictated by in vitro and in vivo efficacy studies. The intrinsic "built-in" lipid PEGylation facilitates a longer circulation time compared to particles without PEG. PEG incorporation yields a steric hydration barrier shield which facilitates long-lived in vivo circulation. (i.e avoidance of the reticuloendothelial system and non-specific uptake by macrophages).

Following the mixing of drug and siRNA/Dendrimer polyplex in presence of lipids, the solution is extruded through a series of filters. First three times through a 5 μm filter, three times through 1 μm filter, and five times through a 200 nm filter collecting extrudate in a sterile tube. Excess siRNA complex, drug and lipids are removed by spinning for 45 minutes at 24000 rpm at 4 C (3×) in an ultracentrifuge.

Figure 4A:
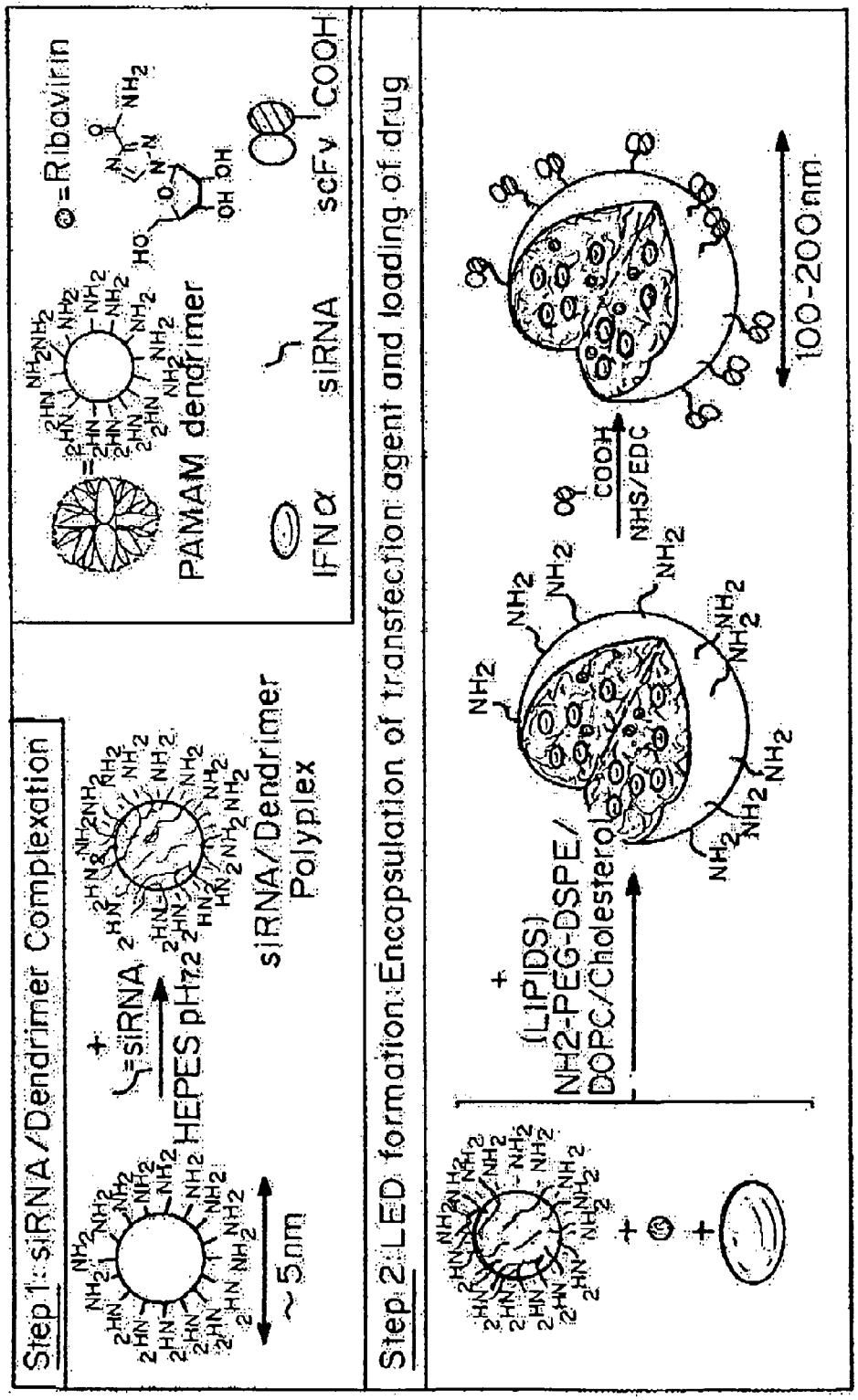
FIG. 4A is a schematic of LED preparation encapsulating siRNA/Dendrimer polyplex and drug combinations, with covalent modification of the outer shell with targeting antibodies or single chain variable fragments (scFv).

FIG. 4A is a schematic of LED preparation encapsulating siRNA/dendrimer polyplex and drug combinations, with covalent modification of the outer shell with targeting antibodies or single chain variable fragments (scFv). Attachment of antibodies or scFv to the amine terminated liposome is achieved by activating the protein in 0.1 MES buffer (pH 5.5) in the presence of ethyldicarbodiimide and N-hydroxysuccinimide for 10 min followed by addition to particles in buffered saline (pH 7.4). This reaction activates carboxylate groups on the protein for covalent linkage to exposed amine groups on the particles. Initially, the reaction stoichemetery is adjusted to yield an approximate density of 1-10 scFv molecules per particle, however, this density can be easily increased by varying the stoichiometry of the reaction to facilitate maximal internalization. Total time for the reaction is 30 min at room temperature. These reaction conditions have no effect on the integrity or function of encapsulated agents.

Results

Figure 4B:
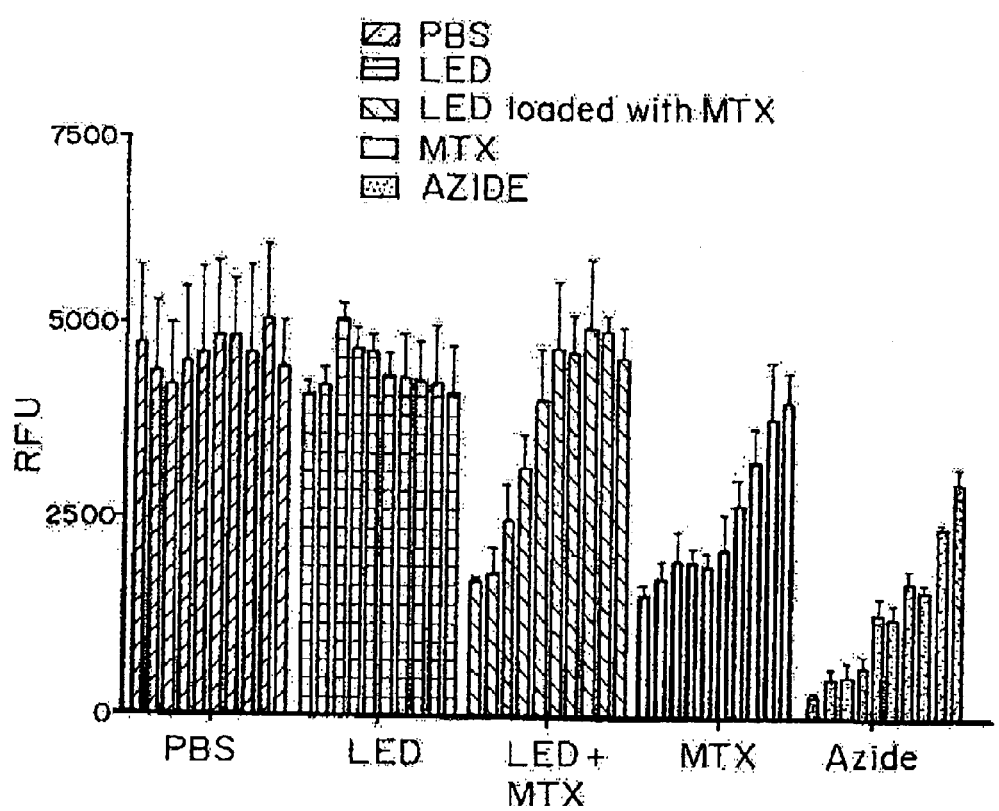
FIG. 4B is a graph of the cytotoxicity of LED and LED encapsulating the model drug methotrexate (MTX). Bars indicate successive dilutions of LED or drug or combinations from 1 mg/ml to 10 μg/ml. Azide is used as a positive control for cell killing.

LEDs can facilitate drug internalization as depicted in FIG. 4A with macrophages inculture. The drug Methotrexate (MTX) was used as a model drug. FIG. 4B shows the cytotoxicity of LED and LED encapsulating the model drug methotrexate (MTX). Bars indicate successive dilutions of LED or drug or combinations starting from (1 mg/ml left to right to 10 ug/ml). Azide is used as a positive control for cell killing. Starting at 10%, left to right, and increasing to 1%. Compared to free drug (MTX), LED containing MTX were slightly less toxic, presumably because of drug sequestration. LEDs alone showed no cytotoxicity. LEDs encapsulating the dye rhodamine facilitate internalization and cytoplasmic localization of the dye and LEDs containing the pGFP plasmid showed enhanced efficiency in transfection of macrophages compared to a standard transfection agent such as lipofectamine.

LEDs encapsulating the dye rhodamine facilitate internalization and cytoplasmic localization of the dye and LEDs containing the pGFP plasmid showed enhanced efficiency in transfection of macrophages compared to a standard transfection agent such as LIPOFECTAMINE®.

Figure 4C:
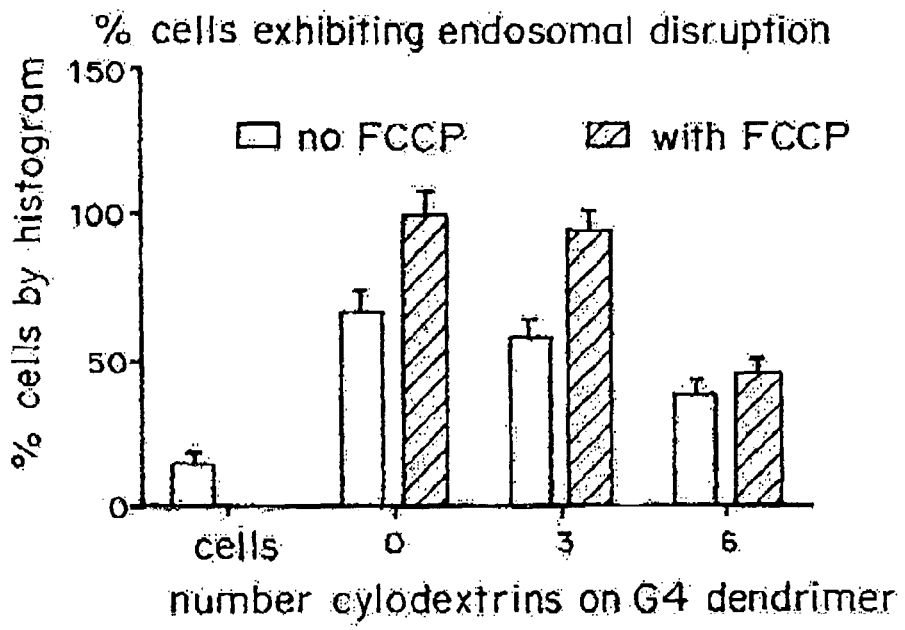
FIG. 4C is a bar graph showing the % cells exhibiting endosomal disruption following treatment with unmodified generation 4 PAMAM dendrimers (G4), or dendrimers conjugated to cyclodextrin molecules (CD) that substituted and shielded primary amines with or with FCCP, a small molecule ionophore, carbonylcyanide p-trifluoromethoxyphenylhydrazone.

To determine if terminal amine groups on PAMAM dendrimers provide endosomal buffering and disrupt endosomes by the proton sponge effect, an Acridine Orange (a dye whose spectral properties change depending on its location in endosomes or cytosol) assay was used with BMDCs, which were treated with unmodified generation 4 PAMAM dendrimers (G4), or dendrimers conjugated to cyclodextrin molecules (CD) that substituted and shielded primary amines with or without ionophore carbonylcyanide-p-trifluoromethoxyphenylhydrazone (FCCP). The results indicate that of the tested combinations, unmodified G4 dendrimer was best at endosomal disruption followed by G4-3CD (FIG. 4C). G4-6CD was the least effective at endosomal disruption of the combinations tested, supporting the idea that proton sponge effect is mediated by primary amines and substituting amines with CD decreases buffering capabilities.

Figure 4D:
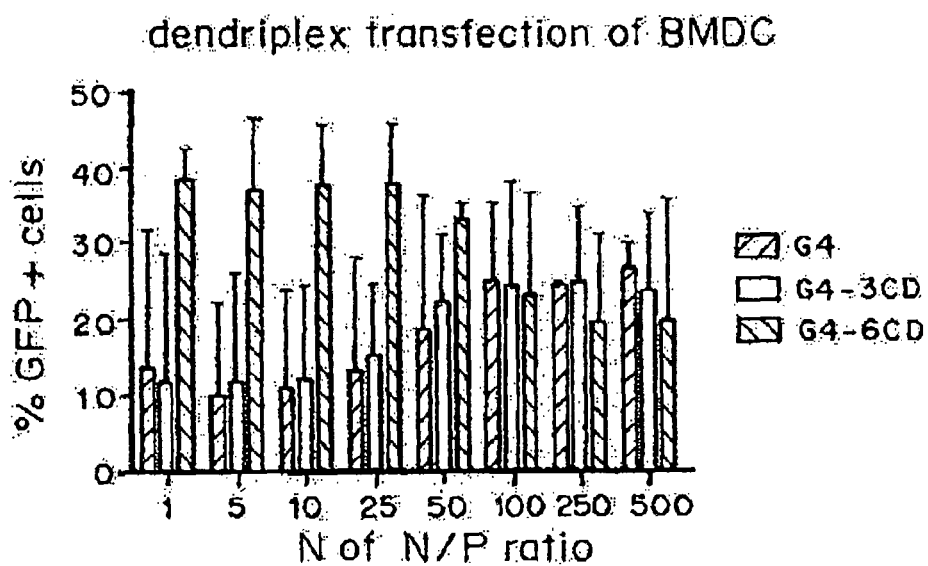
FIG. 4D is a bar graph showing the number of GFP positive cells as a percent of total cells transfected with pGFP using various LEDs (G4, G4-3CD, G4-6CD) at various N/P ratios.

LEDs were also tested using different dendrimer (G)-cyclodextrin conjugates (CDs) and Nitrogen/Phosphorus (N/P) ratio, and compared to vector delivery (pGFP) using LIPOFECTAMINE® 2000 and liposomes in a variety of cells types. CD significantly affected dendriplex (FIG. 4D). Dendriplexes (from modified dendrimers) transfect better than Lipofectamine 2000 in BMDCs. LEDs also transfected better than liposomes encapsulating vector in BMDCs.

Figure 4E:
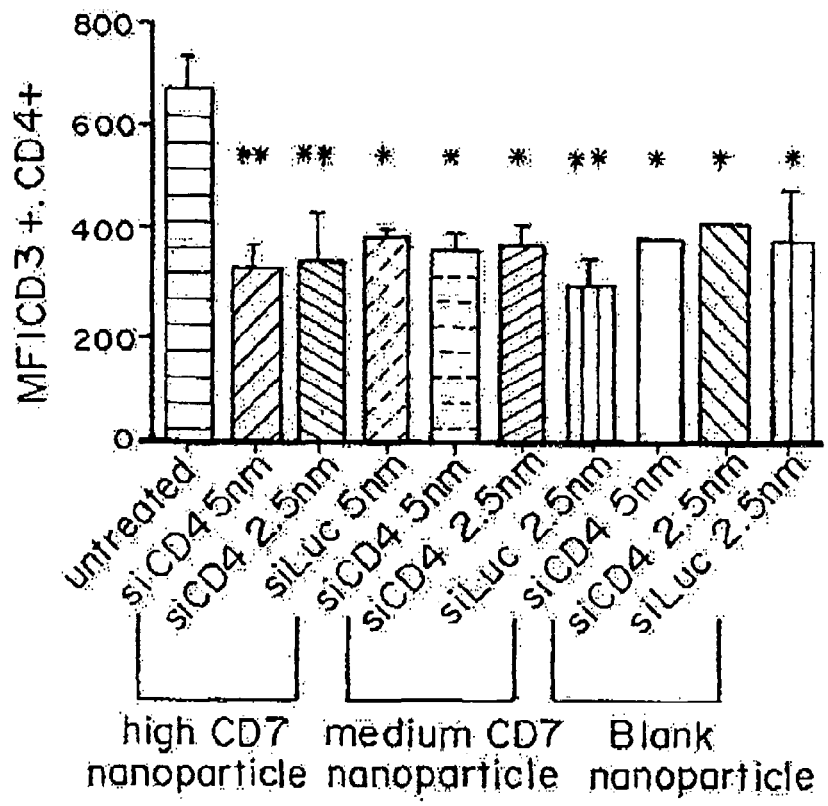
FIG. 4E is a bar graph showing relative number of MFICD3+, CD4+ cells control and various LEDs encapsulating different dosages of CD4 or Luciferase siRNA constructs.

LEDs encapsulating siRNA against CD4 or Luciferase (Luc) and surface functionalized with anti-CD7 were test for the ability to mediate internalization target mRNA knockdown in Jurkat (human T cell line) cells. Results indicated that LED delivered siRNA reduced surface expression of CD4, or Luc relative to controls (FIG. 4E).

Figure 4F:
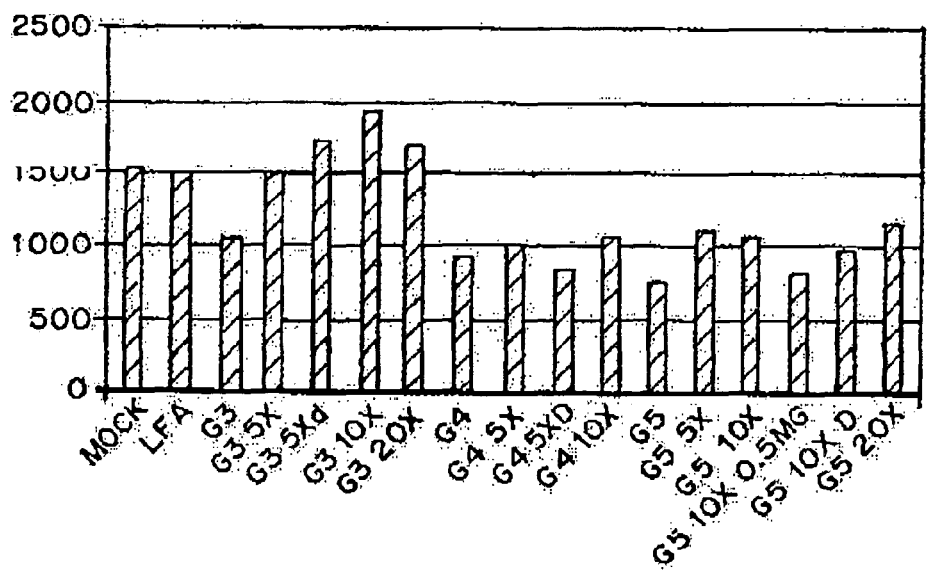
FIG. 4F is a bar graph showing the level of GFP expression in 293T cells stably transfected with eGFP following transfection of an siGFP construct using LIPOFECTAMINE® or various LEDs containing combinations of different dendrimer (G)-cyclodextrin conjugates (CDs). This graph measures the mean fluorescence intensity (MFI) of GFP to assess silencing ability of modified dendrimers complexed with siGFP. The x-axis should read as follows.

In a second experiment, LEDs including 200 ug of dendrimer and 400 pmol siGFP. (Ctl=LFA:siGFP) were utilized to knockdown GFP expression is a stably transfected cell line. Stable 293T-eGFP cells were treated with dendrimers for 4 h in SFDMEM followed by examination of GFP expression. Cells treated with most dendrimer (G)-cyclodextrin conjugates (CDs) combinations exhibited greater reduction in GFP expression compared to mock and LIPOFECTAMINE®:siGFP controls (FIG. 4F).

Example 8

Antigen Cross Presentation with Lipid Encapsulated Dendrimers

Materials and Methods

Mouse Bone Marrow-Derived Dendritic Cells (BMDCs) were incubated with liposomes encapsulating ovalbumin (OVA) alone, dendrimer alone, or both OVA and dendrimer (LED).

Results

Figure 5A:
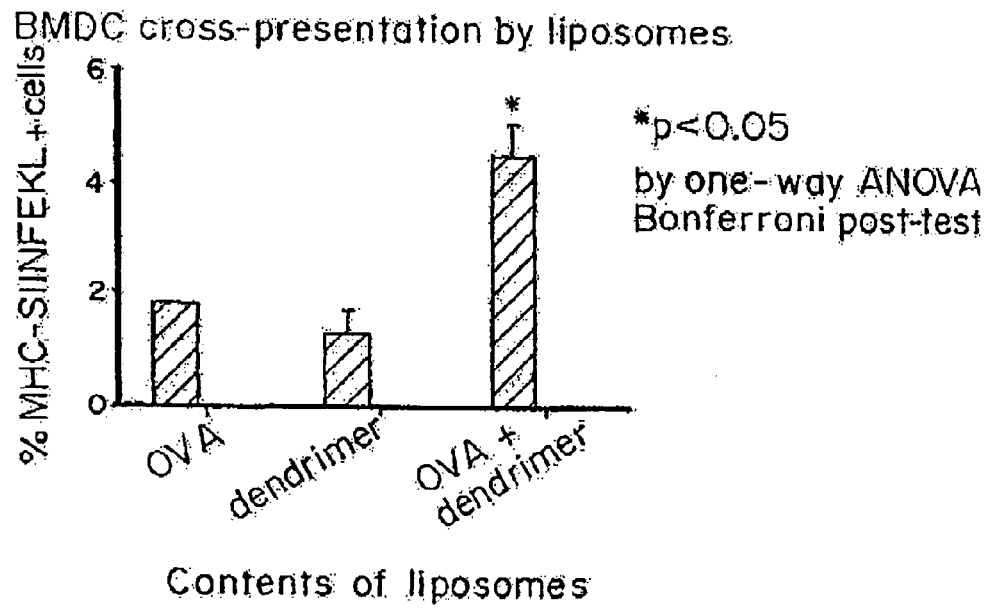
FIG. 5A is a bar graph showing the % MHC-SIINFEKL, murine bone-marrow-derived dendritic cells (BMDCs). MHC-SINFEKL positive cells following treatment with liposomes containing ovalbumin alone (OVA), dendrimer alone, or a combination of OVA and dendrimer. *$p<0.05$ by one-way ANOVA Bonferroni post-test.

Controls of cells and empty liposomes showed undetectable levels of 25.D16 antibody staining, which binds MHC Class I-SIINFEKL complexes. Cells receiving LEDs showed the highest level of antigen cross-presentation. (See FIG. 5A). *p<0.05 by one-way ANOVA Bonferroni post-test.

Example 9

Vaccine Delivery with Lipid Encapsulated Dendrimers

Materials and Methods
Antigen Presentation
$1 \times 10^5$ BMDC/well (96 well plate)+25 uL liposomal particles. Particle groups:
  a. −/−(nothing outside nothing inside particles)
  b. −/OVA (nothing outside, OVA encapsulated)
  c. −/G5+OVA (nothing outside, OVA and G5 dendrimer inside)
  d. −/G5+OVA+CpG
  e. MPLA/− (MPLA outside, nothing inside)
  f. MPLA/OVA
  g. MPLA/OVA+G5
  h. MPLA/OVA+G5+CpG (MPLA outside; OVA, G5 dendrimer, CpG encapsulated)

Where OVA=ovalbumin, MPLA=monophosphoryl lipid A, G5=generation 5 dendrimer, CpG=CpG oligonucleotide (TLR9 ligand).

Treatment was incubated with BMDC for 24 hours followed by 4 day co-incubation with WT splenocyte.

Analysis of Pro-Inflammatory Cytokine Production

BMDCs were incubated with liposomal nanoparticles encapsulating antigen and surface-functionalized with increasing amounts of TLR ligand CpG for 24 hours before supernatant analysis by ELISA.

Results

Figure 5B:
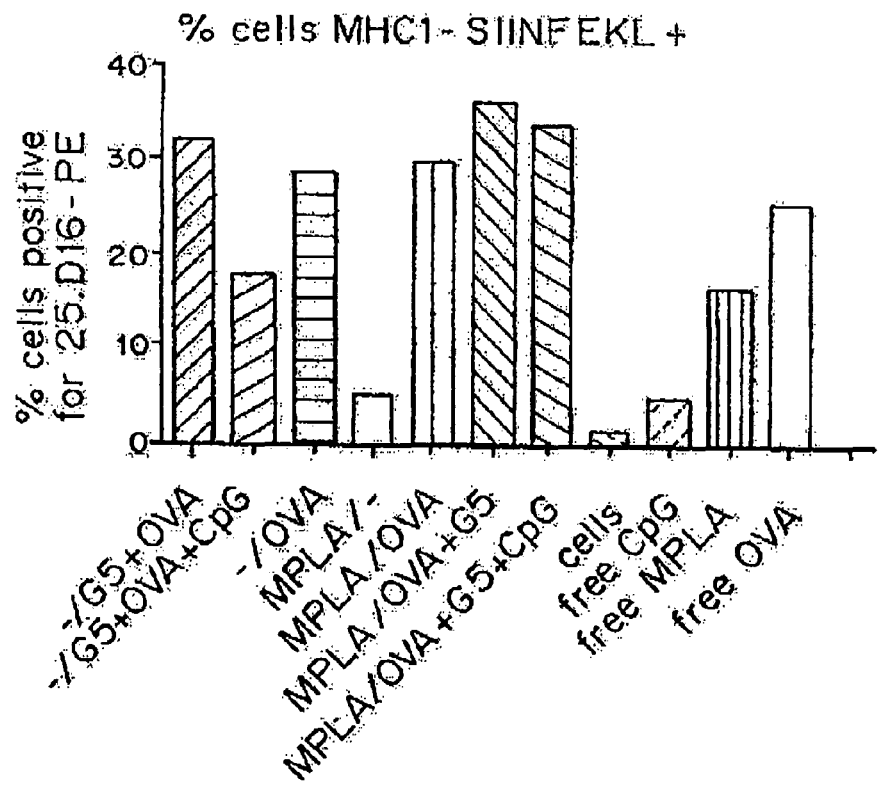
FIG. 5B is a bar graph showing the % MHC-SINFEKL positive cells (by 25.D16-PE staining) following with various controls and liposomes includes one or more of dendrimer (i.e., G5), antigen (i.e., ovalbumin (OVA)), and surface modifications (i.e., MPLA, and/or CpG) as labeled. The particle formulation containing MPLA, OVA, G5, and CpG was not shown since it encapsulated a prohibitively low amount of OVA protein, and normalizing treatment groups by the amount of OVA resulted in cell toxicity because the particle concentration was higher than other groups.

Cells were stained with 25.D16-PE, an antibody that is specific for mouse MHC Class I-SIINFEKL complexes, as assessed for antigen cross-presentation by flow cytometry. The results indicated that −/OVA particles induce some cross-presentation, which was increased by OVA particles containing dendrimer. Particles the combination of MPLA, CpG, and dendrimer induce the highest amount of cross-presentation. (See FIG. 5B).

Figure 5C:
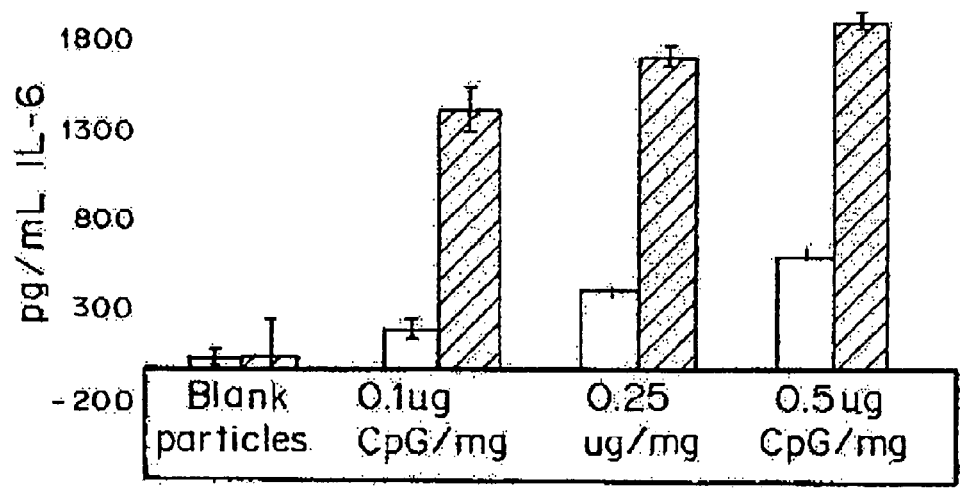
FIG. 5C is a bar graph showing the IL-6 (pg/mL) expressed from bone marrow dendritic cells (BMDC) treated with LED presenting increasing amounts of CpG.

Liposomal nanoparticles surface functionalized with CpG also induced a dose-dependent increase the production of pro-inflammatory cytokine IL-6. (See FIG. 5C).

Example 10

Preparation and Characterization of Nanolipogels Containing Mycophenolic Acid (MPA)

A system consisting of a biodegradable, cyclodextrin-based hydrogel encapsulated within a lipid bilayer, was used to deliver molecules that selectively immunosuppress an individual with an autoimmune disease.

Materials and Methods

Fabrication of Lipo Gel Nanoparticles

Figure 6A:
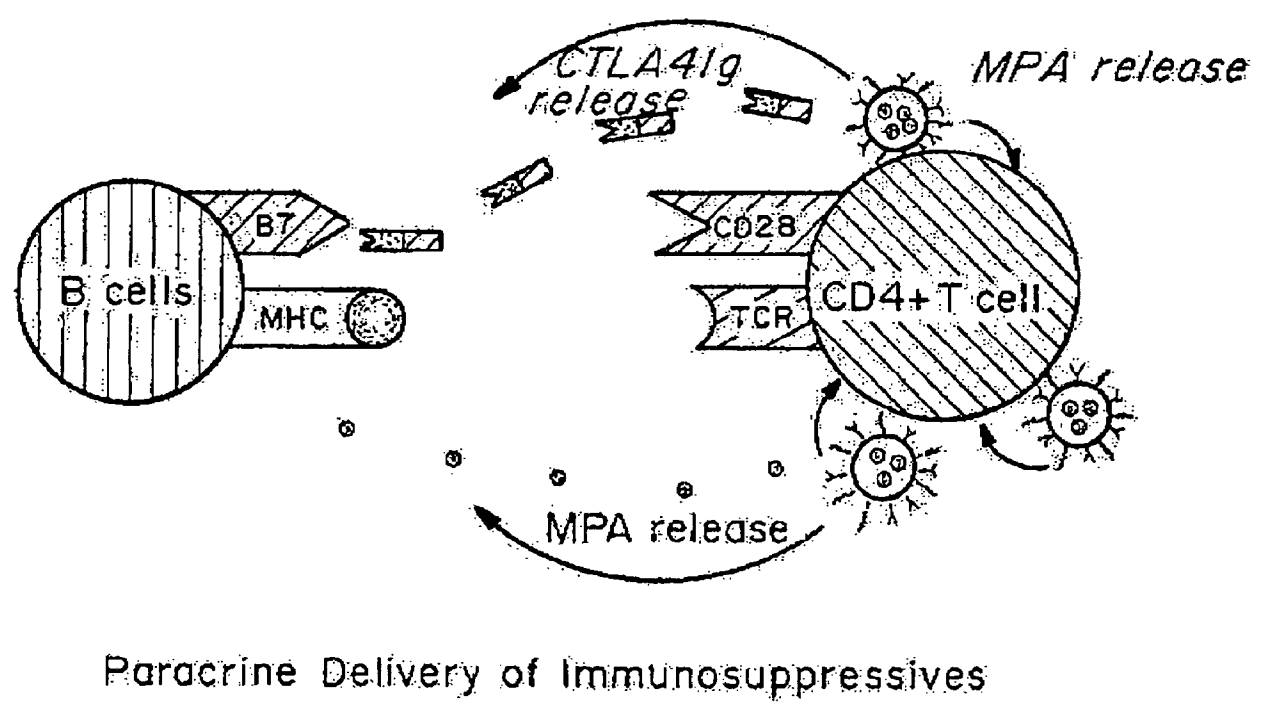
Figure 6B:
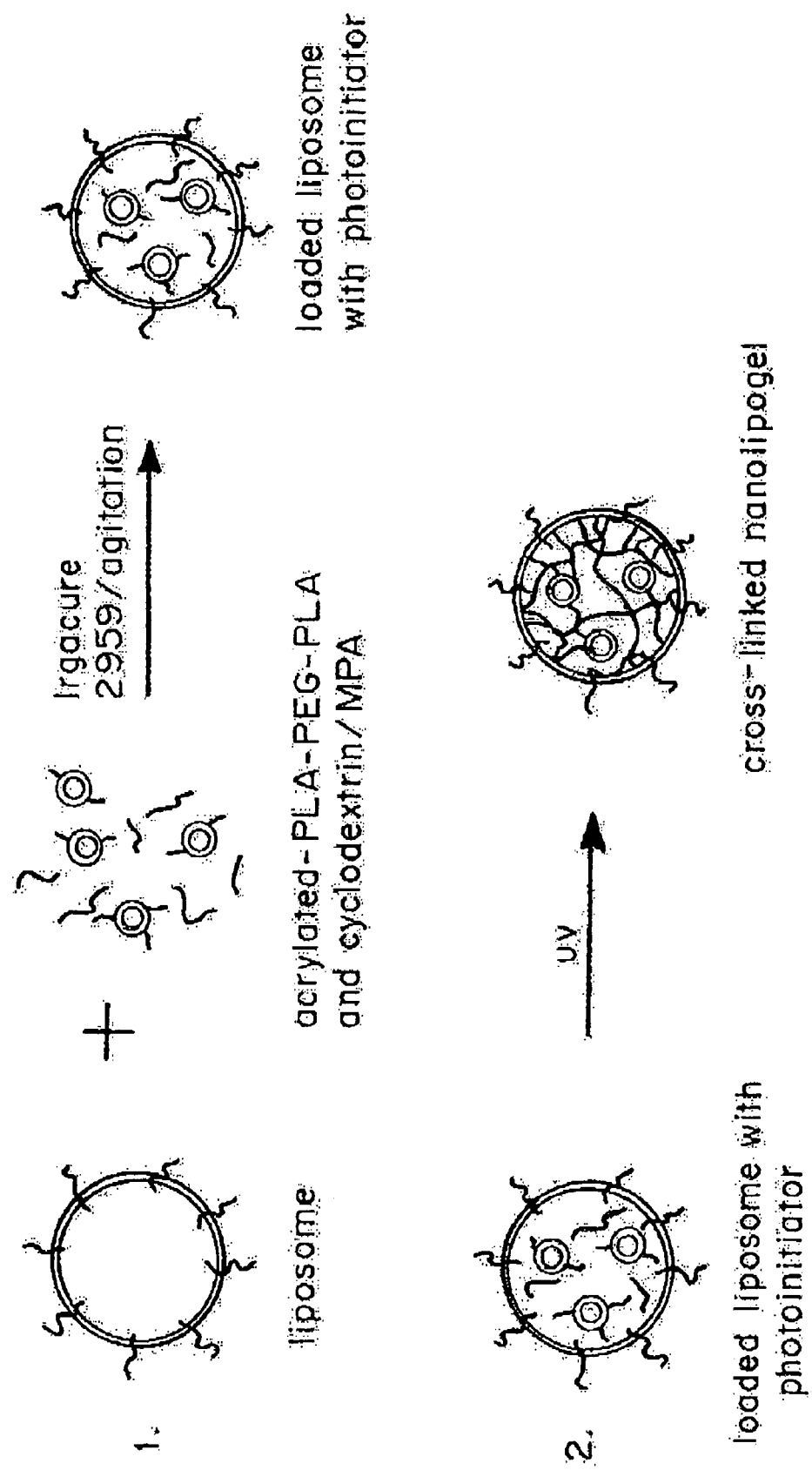
FIG. 6B is a schematic for nanolipogel particle fabrication for delivery of MPA to cells in patients with autoimmune disease.
Figure 6C:
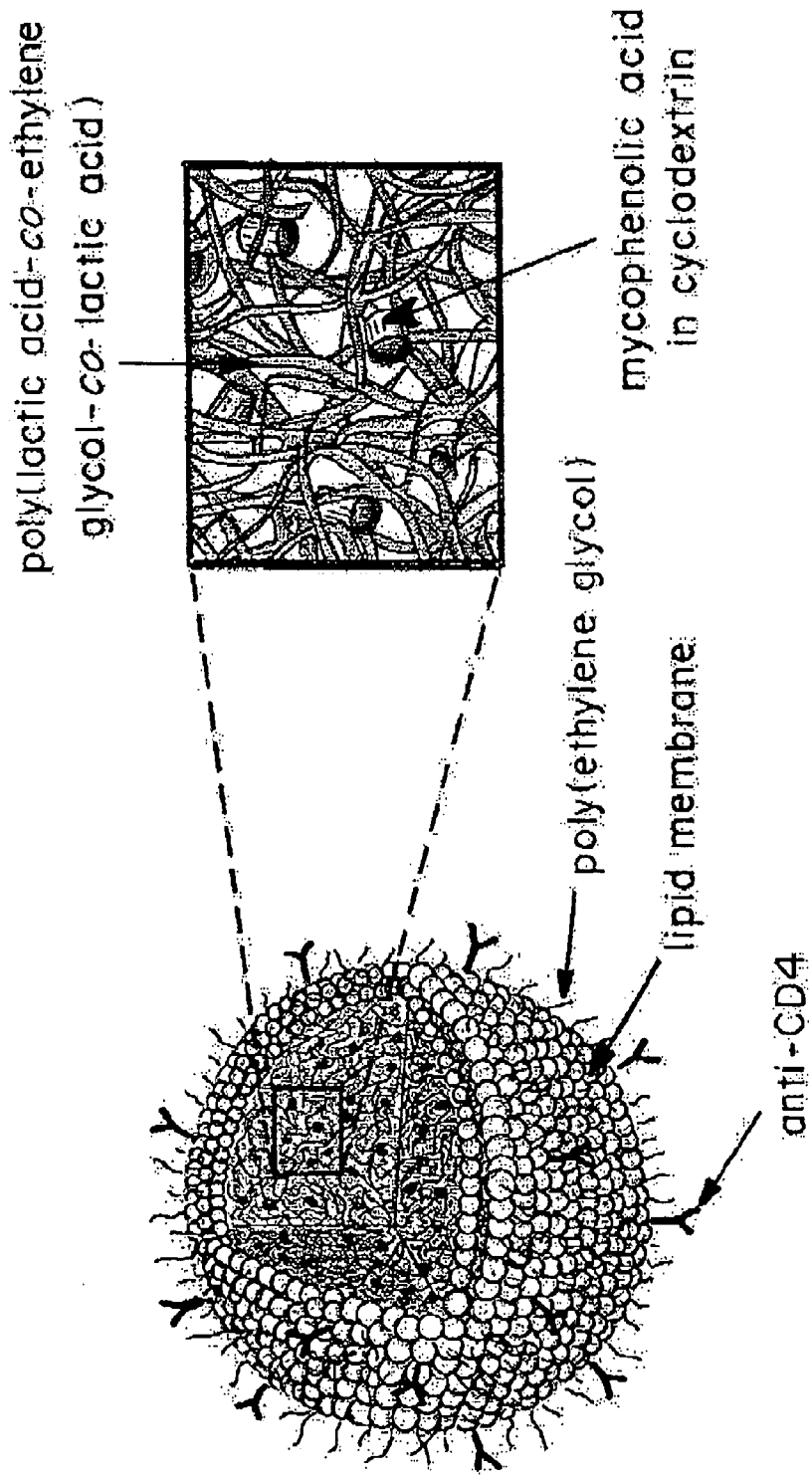
FIG. 6C is a depiction of a mycophenolic acid (MPA)-cyclodextrin loaded nanolipogel.
Figure 7A:
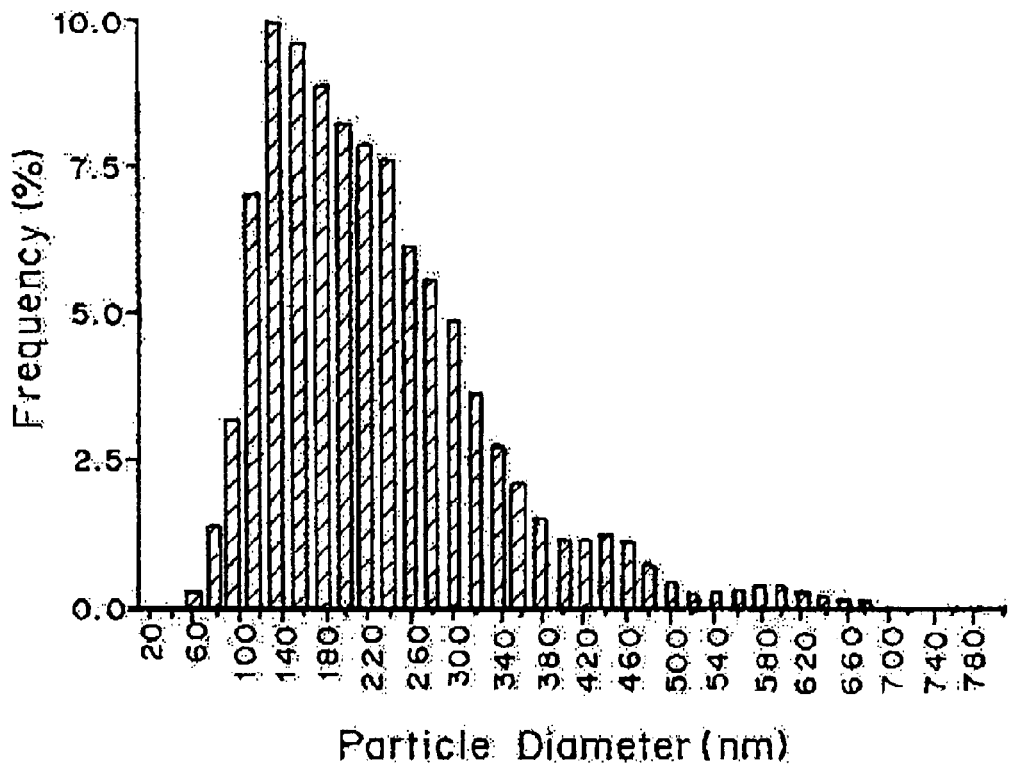
FIG. 7A is a graph showing the particle size distribution of nanolipogels.
Figure 7B:
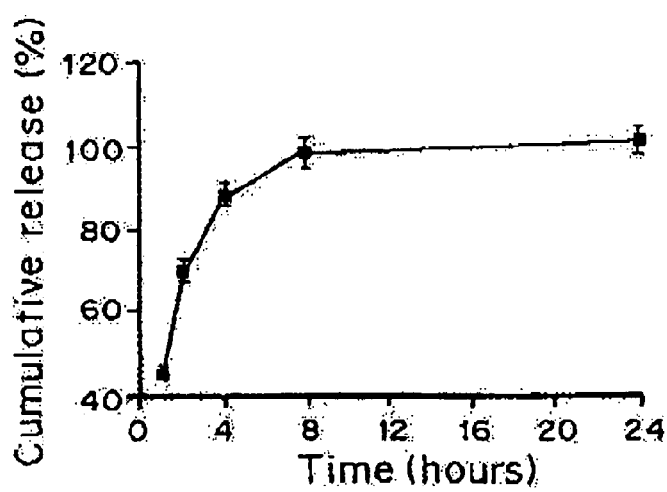
FIG. 7B is a line graph showing release of MPA from MPA-loaded nanolipogels over hours.
Figure 7C:
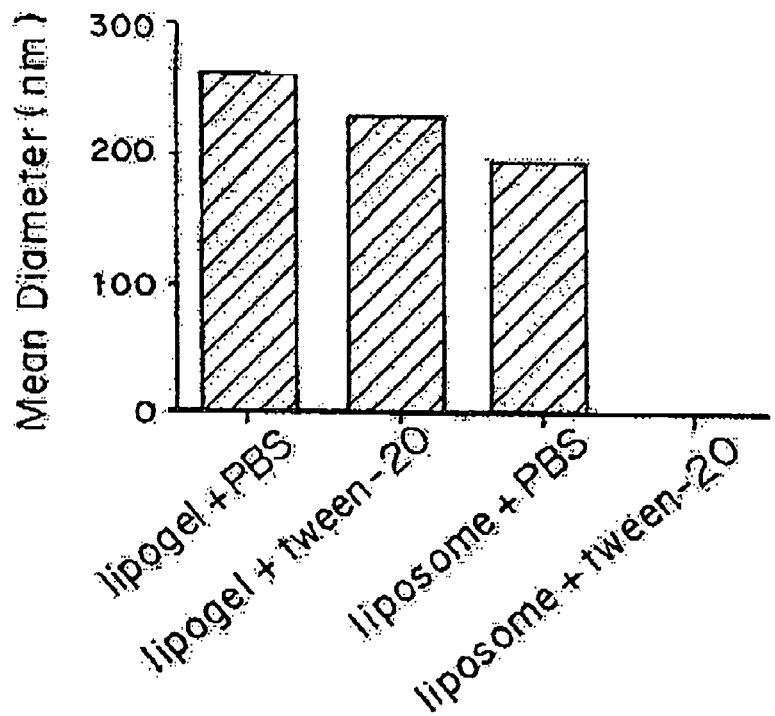
FIG. 7C shows mean diameter (nm), for Nanolipogel in PBS, Nanolipogel in TWEEN 20, liposome in PBS and liposome in TWEEN 20.

Hydrogel-based nanoparticles (nanolipogels) were fabricated by remotely loading liposomes with a diacrylate-terminated co-block polymer of poly(lactic acid) and poly(ethylene glycol) in the presence of a photoinitiator (FIG. 6B). Mycophenolic acid (MPA), which was complexed with a cyclodextrin derivative to improve its aqueous solubility, was also remotely loaded into the liposome. This loading process involved rehydrating lyophilized, preformed liposomes in aqueous solution with these precursors and drug. Photopolymerization of these nanoparticles under UV light induced cross-linkage between the acrylated-precursors and gelation of the particle interior into a stable matrix. These nanolipogels had an average hydrodynamic diameter of 225 nm, with a median diameter of 203 nm and mode diameter of approximately 141 nm. See FIG. 7A.

To prepare liposomes, a mixture of 2:1:0.1 molar ratio of phosphatidylcholine:cholesterol:phosphatidylethanolamine (Avanti Polar) in chloroform was evaporated under nitrogen gas stream and then lyophilized. The resulting dry lipid film was then rehydrated with PBS to form large lipid vesicles. This large lipid vesicle suspension was extruded five times through a 200 nm pore filter (Whatman) and then five more times through a 100 nm pore filter. Lipid nanoparticles were then surface modified with anti-CD4 targeting antibodies (clone RM4-4, BD Biosciences) using sulfo-NHS/EDC (Pierce) covalent conjugation, and then lyophilized overnight.

Next, 20 mg of mycophenolic acid (Sigma) in 400 μL of methanol was complexed to 100 mg of a mixture of aminomethacrylate (Sigma) and succinylatedβ-cyclodextrin (CTD Holdings) and 300 mg of hydroxypropyl β-cyclodextrin (CTD Holdings) in PBS under vigorous mixing for 15 min at room temperature. The methanol was evaporated from the MPA-cyclodextrin mixture, and the remaining cyclodextrin-MPA mixture was resuspended with Irgacure 2959 (Ciba) photoinitiator and a PEG-oligomer consisting of 4000 Da linear poly(ethylene glycol) flanked on each side by approximately 1-2 lactic acid monomers with a terminating acrylate group. The synthesis of this crosslinkable oligomer is described by Sawhney (Sawhney, et al., Macromolecules, 26:581-587 (1993)).

Lyophilized liposomes were then remotely loaded with the aqueous MPA-cyclodextrin-Irgacure-PEG mixture. Vigorous mixing was applied for 30 min. The liposomes were then cross-linked under a 430 W UV lamp with UVA light (315-400 nm transmission filter) for 8 min on ice to form the nanolipogel, then rinsed in PBS and collected by ultracentrifugation at 98,205 rcf for 1 hr at 4° C. Nanolipogels were stored at −20° C. until use.

PLGA nanoparticles encapsulated with MPA were synthesized and characterized as previously described (Shirali, et al., *Am J Transplant*, 11(12):2582-92 (2011).

Nanoparticle Characterization

The hydrodynamic diameter of nanoparticles in PBS was measured with an NS500 nanoparticle tracking system (Nanosight, Amesbury Wilshire, United Kingdom). For transmission electron microscopy analysis, nanolipogel samples were stained with osmium tetroxide and then imaged on an FEI Tenai Biotwin microscope. Scanning electron microscopy was performed on gold-sputtered PLGA nanoparticles, and imaged with an XL-30 ESEM-FEG (FEI, Hillsboro, Oreg.) microscope. The amount of MPA loaded in nanoparticles was determined from the supernatant of nanoparticles dissolved in 1% triton X-100 in 0.1 M NaOH for at least 1 hr at 37° C.; the fluorescence of MPA was measured using an excitation wavelength of 340 nm and an emission wavelength of 450 nm on a SpectraMax plate reader (Molecular Devices).

Results

In Vitro Characterization of a Hydrogel-Based Nanoparticle

These nanolipogels had an average hydrodynamic diameter of 225 nm, with a median diameter of 203 nm and mode diameter of approximately 141 nm.

Figure 7D:
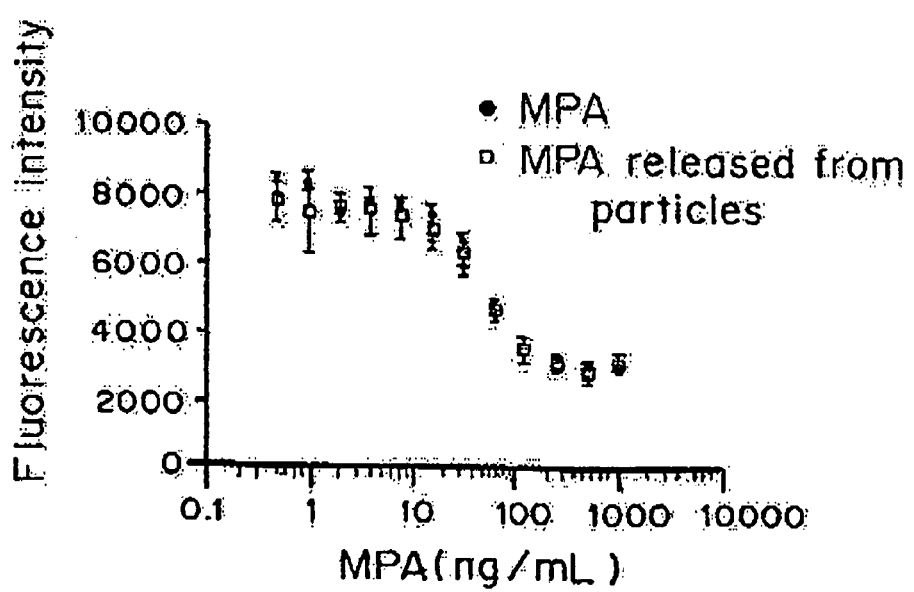
FIG. 7D shows fluorescence intensity in Jurkat cells treated with free MPA (ng/mL) or the supernatant of PBS containing drug releasing nanolipogels. The supernatant contained nanolipogel-release drug, but no nanolipogel particles. Increase of fluorescence intensity correlates with increased proliferation.

Gelation of the nanoparticle interior into a stable matrix was demonstrated by exposing these nanolipogels to surfactant; the photo-cross-linked matrices retained the diameter of the particle whereas conventional liposomes ruptured upon surfactant treatment (FIG. 7D). The representation of these nanolipogels as hydrogel particulates with a lipid exterior was confirmed by transmission electron microscopy, which showed that lipid-specific osmium tetroxide staining of cryosectioned samples had a localized staining pattern confined to the exterior membrane of the particle. These nanolipogels could be loaded with bioactive mycophenolic acid and sustain its release. MPA that was loaded maintained its potency and was released in a sustained fashion for over a week.

Figure 8A:
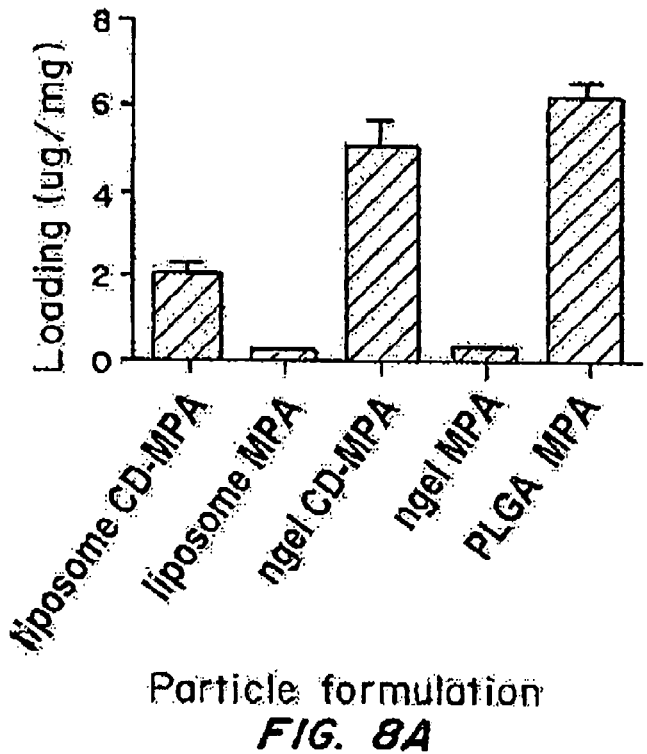
FIGS. 8A and 8B are graphs of loading (microgram/mg) (8A), percent encapsulation efficiency (8B) for liposome CD-MPA, liposome MPA, nanolipogel CD-MPA, Nanolipogel MPA, and PLPGA MPA (A, B) and Nanolipogel.
Figure 8B:
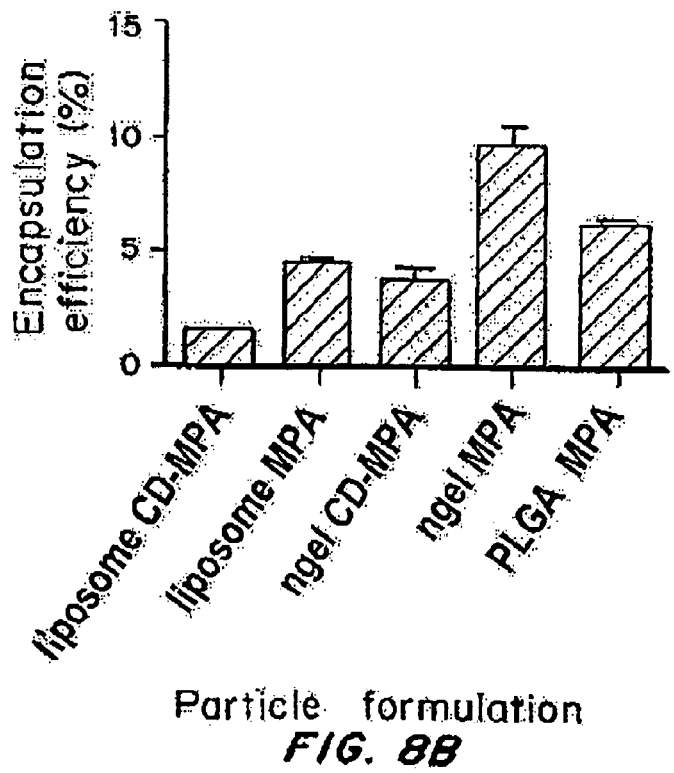
Figure 8C:
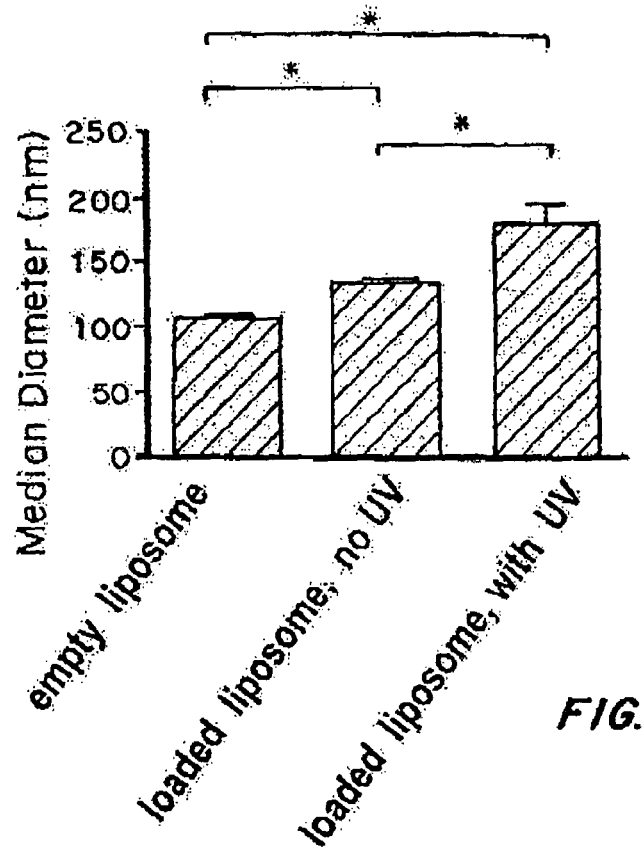
FIGS. 8C-8D are graphs of median diameter (nm) of liposomes—empty, loaded, and loaded and crosslinked 8C), and nanogel+/−triton X-100, or liposome+/−triton X-100 (8D).
Figure 8D:
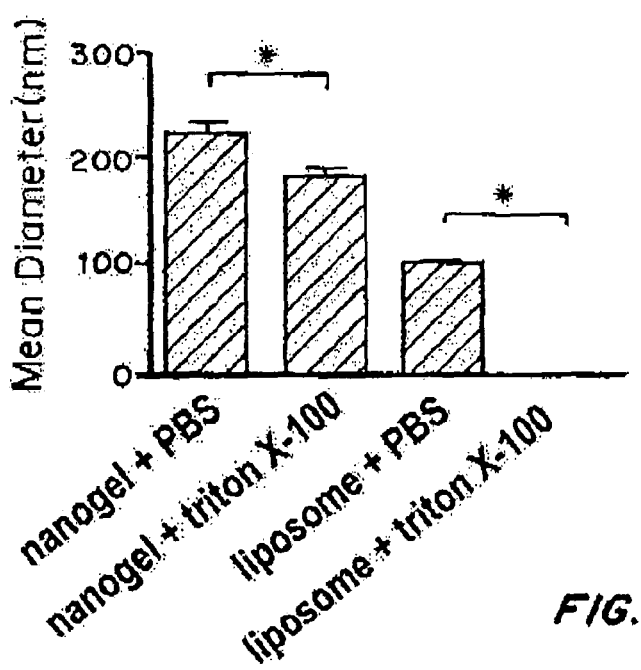
Figure 8E:
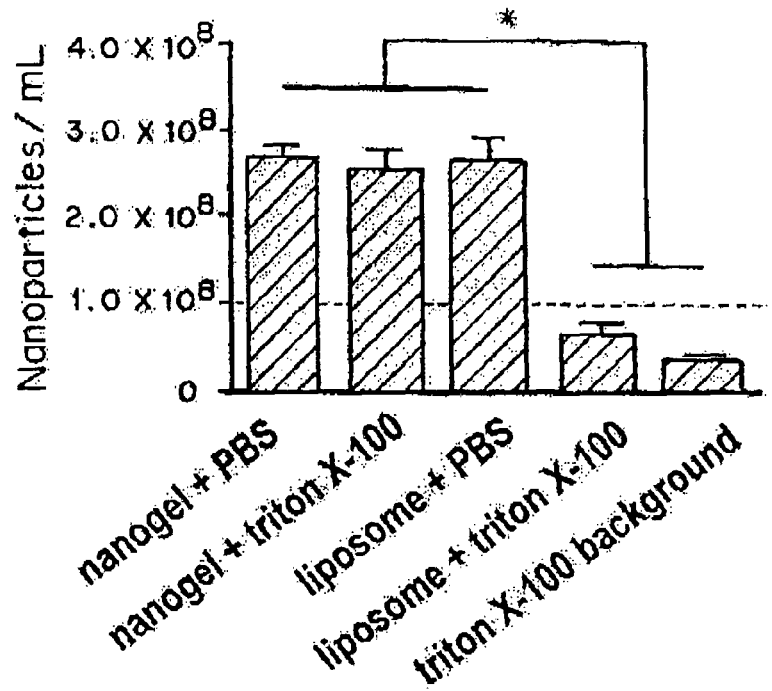
FIG. 8E is a bar graph of single particle counting of nanogel and liposome+/−Triton X-100 treatment.

The average MPA loading in these nanolipogels was approximately 6.65±3.82 µg MPA/mg particle, with an encapsulation efficiency of approximately 3.79% (FIGS. 8A and 8B). In contrast, liposomes with the same lipid composition as the nanolipogels encapsulated less drug, with a loading of 2.03±0.14 µg MPA/mg particle (FIG. 8A), and an encapsulation efficiency of 1.37% 2.5 (FIG. 8B). Consistent with the swelling nature of hydrogel nanoparticles, a modest increase in the effective hydrodynamic diameter of the particles was observed following photopolymerization (FIG. 8C). The formation of a stable interior was verified by exposing nanogels to triton X-100: liposomes ruptured upon exposure to this surfactant, whereas lipogels do not. PBS is phosphate buffered saline at pH 7.4 (FIG. 8D). Single particle counting verified that triton X-100 ruptured and decreased the number of liposomes but not nanogels (FIG. 8E). Horizontal dashed line indicates the limit of detection of the Nanosight particle tracking instrument (FIG. 8E). In FIG. 8C-8E, error bars represent standard error measurement, with at least 3 measurements per group. *$p<0.05$ or less by 1-way ANOVA with Bonferroni multiple comparison test.

Example 11

Functionalization of Nanolipogels and Use of Functionalized Nanolipogels to Target CD4 T Cells Materials and Methods To achieve CD4 T cell targeting potential with these particles, a non-depleting antibody for CD4 was covalently attached to the surface of the particle. To test the cell-specific binding capacity of the CD4 targeted particles, fluorescently labeled particles were incubated with splenocytes ex vivo, and the colocalization of particle fluorescence with leukocyte specific subsets determined via flow cytometry. CD4 T cells could specifically attach to CD4 targeted nanoparticles.

In order to demonstrate that these CD4-targeted, MPA-loaded nanoparticles could inhibit CD4 T cell proliferation, the proliferative capacity of CD4 T cells in vitro was measured, after exposing the cells with CD4-targeted and non-targeted MPA-loaded particles. CD4 T cells were briefly incubated with particles, washed to remove any unbound particles, and then stimulated for 4 days with anti-CD3 and anti-CD28 antibodies to promote proliferation.

Results

Experiments were conducted to determine whether nanolipogel particles could be functionalized and used to target CD4 T cells and suppress their proliferation. In lupus, CD4 T cells provide costimulatory signals to B cells which leads to the production of pathogenic autoantibodies. Depletion of CD4 T cells has been shown to provide therapeutic benefit in murine models of lupus (Wofsy, et al., *J Exp Med*, 161(2):378-91 (1985); Wofsy, et al., *J Immunol*, 138(10): 3247-53 (1987)).

Figure 8F:
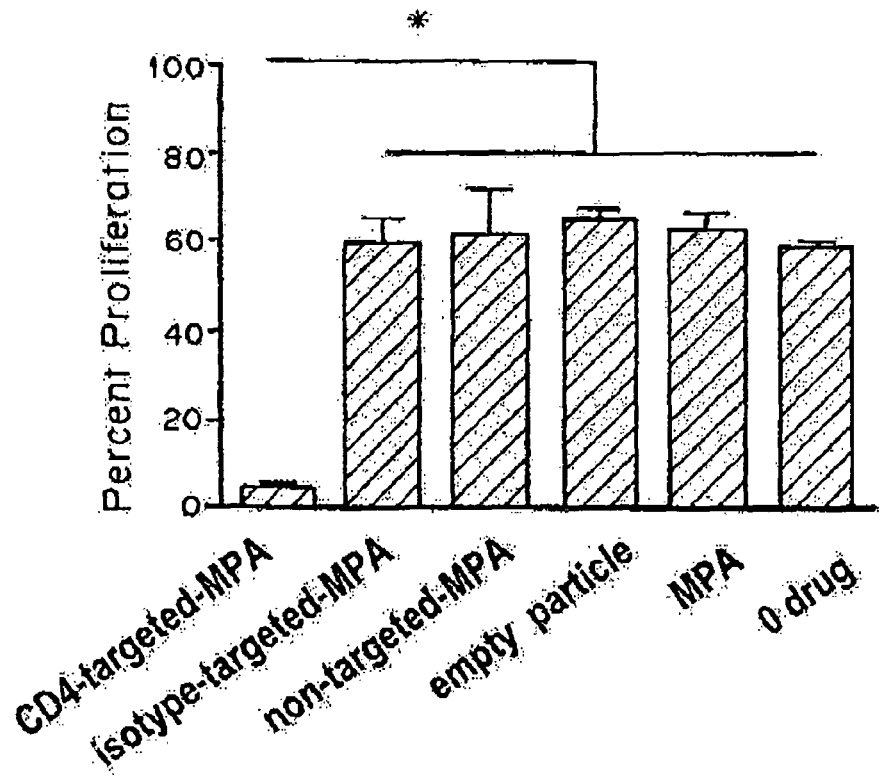
FIG. 8F is a bar graph showing the percent proliferation for CD4-targeted MPA, isotype-targeted-MPA, non-targeted-MPA, empty particle, MPA and no drug.

In incorporate this strategy, CD4 antibody (clone RM4-4) were covalently attached to nanolipogels. CD4 T cells treated with CD4-targeted, MPA loaded nanoparticles had impaired proliferation and cytokine production whereas CD4 T cells that were treated with non-targeted nanoparticles or free MPA (drug not encapsulated in particles) had normal proliferation and cytokine production (FIG. 8F). These results indicate that only the CD4-targeted nanoparticles could remain bound to the CD4 T cells, even after a wash step, and that the encapsulated MPA in these bounds particles was subsequently released into the cells to inhibit their proliferation.

Example 12

Toxicology Studies in Mice

Materials and Methods
Toxicology Studies

Acute toxicity studies were performed in 10 week old C57BL/6 female mice. Mice were dosed with indicated treatment groups on day 0, 1, 2, and 3. After four daily doses of 0.625 mpk MPA in particles were administered, complete blood counts and clinical chemistries for liver and kidney function were measured on 4, 7, and 14 days after the first dose. Serum concentrations of alkaline phosphatase (ALKP), alanine transferase (ALT), total bilirubin (tBIL), and blood urea nitrogen (BUN) were measured using reagents from Teco Diagnostics.

Blood was collected in EDTA spray-coated tubes, and immediately analyzed by complete blood count (CBC) on a Hemavet blood counter. Urine was collected by bladder compression, and analyzed with Uristix test (Bayer).

Renal Analysis and Histology

Urinalysis was performed with Uristix assays. Proteinuria measurements corresponding to 300 mg/dL or greater were considered a positive test. Leukocyte esterase content in the urine that corresponded with 10 or more leukocytes/μL was considered a positive test. Renal function was assessed by the blood urea nitrogen (BUN) content in serum, using a kinetic assay (Teco Diagnostics).

For histology analysis, kidneys from 36-40-weeks-old mice were fixed in 10% neutral buffered formalin, and hematoxylin and eosin stained sections were prepared by the Yale University Pathology Histology Service. Tissues were imaged on a Nikon TE-2000U microscope with a Nikon DS Fi1 color camera and NIS Elements AR software (version 2.30). Scoring of glomerular damage and intertubular infiltration was performed by M. K.

Results

Figure 9A:
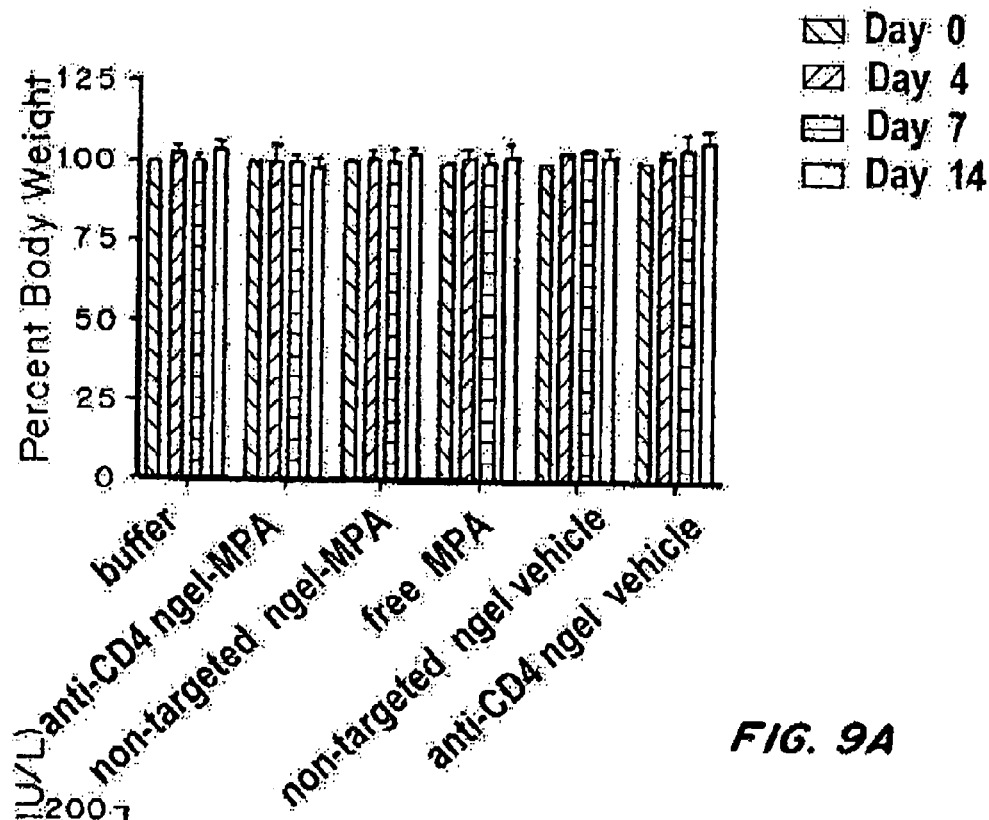
FIGS. 9A-9E are bar graphs of percent body weight (9A), IU/l alkaline phosphatase (9B), IU/l alanine transferase (9C), mg/dl blood urea nitrogen (9D), and mg/dl total bilirubin (9E), on days 0 (solid bars), 4 (open bars), 7 (grey bars), and 14 days (hatched bars) after treatment with buffer, anti-CD4-targeted nanolipogels loaded with MPA, non-targeted nanolipogels loaded with MPA, free MPA, non-targeted nanolipogel vehicle, or anti-CD4-targeted nanolipogel vehicle.
Figure 9B:
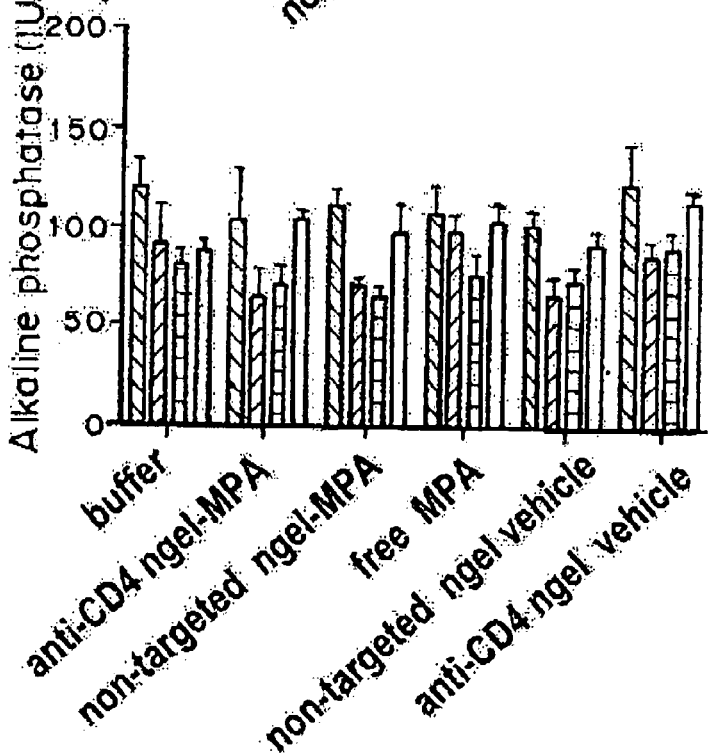
Figure 9C:
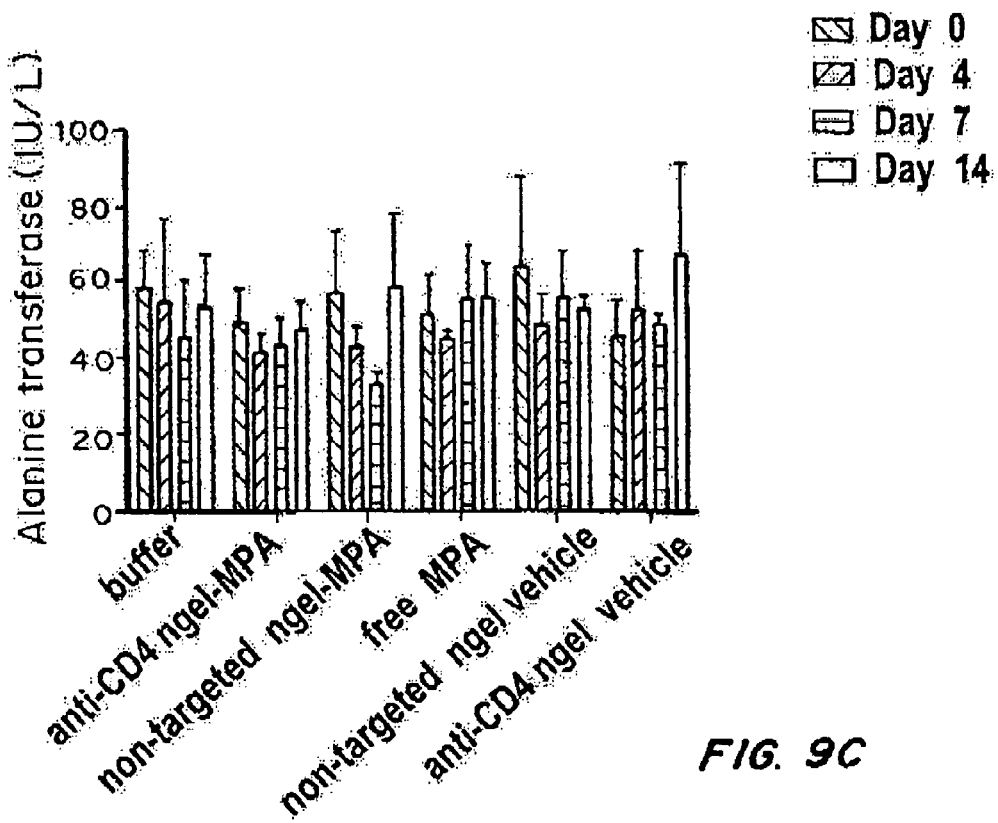
Figure 9D:
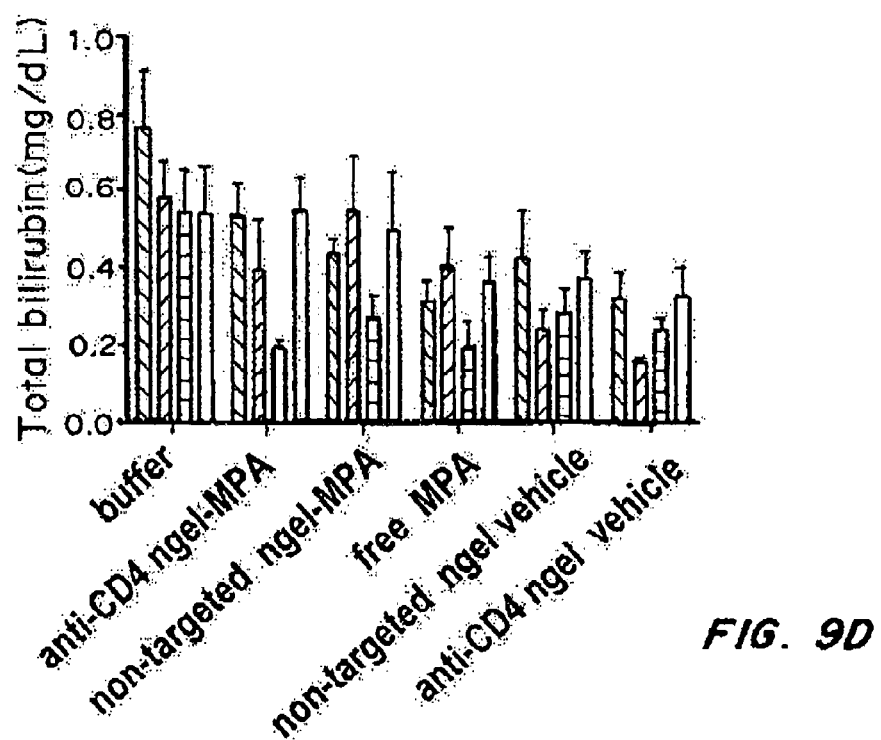
Figure 9E:
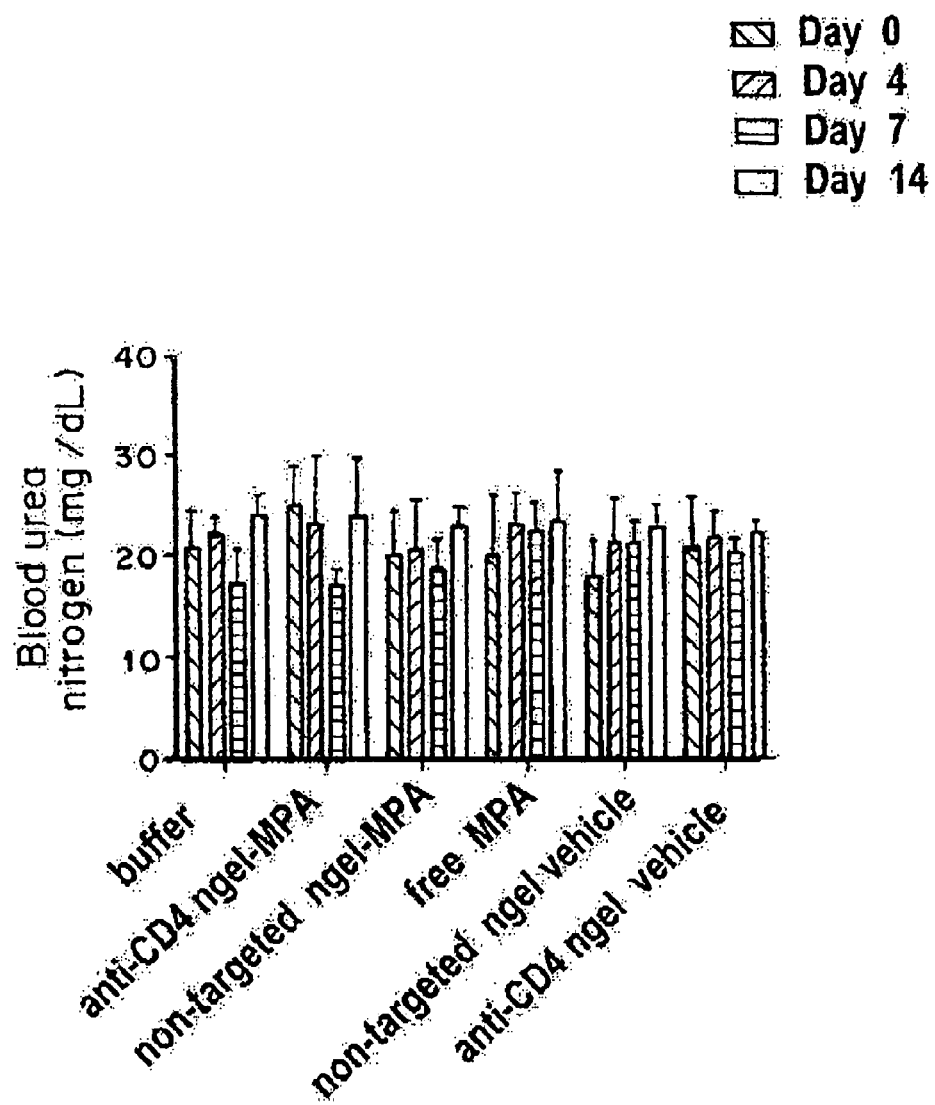
Figure 10A:
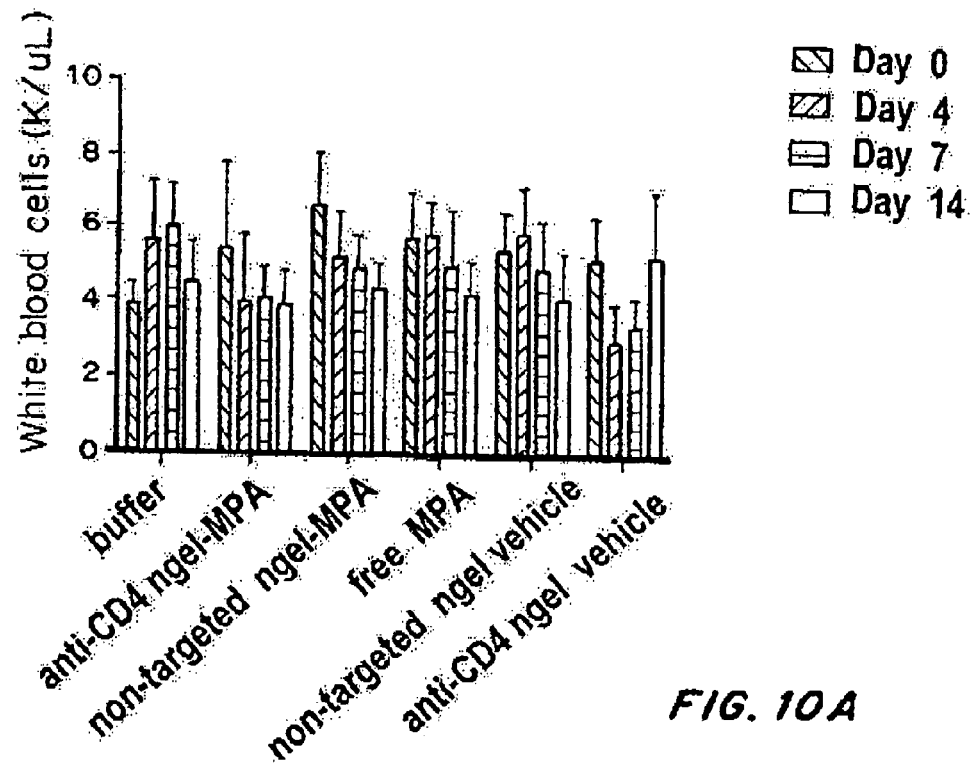
FIGS. 10A-10D are bar graphs of white blood cells (K/microliter) (10A), platelets (K/microliter) (10B), hemoglobin (g/dl) (10C), and hematocrit (%) (10D) on days 0 (solid bars), 4 (open bars), 7 (grey bars), and 14 days (hatched bars) after treatment with buffer, anti-CD4-targeted nanolipogels loaded with MPA, non-targeted nanolipogels loaded with MPA, free MPA, non-targeted nanolipogel vehicle, or anti-CD4-targeted nanolipogel vehicle.
Figure 10B:
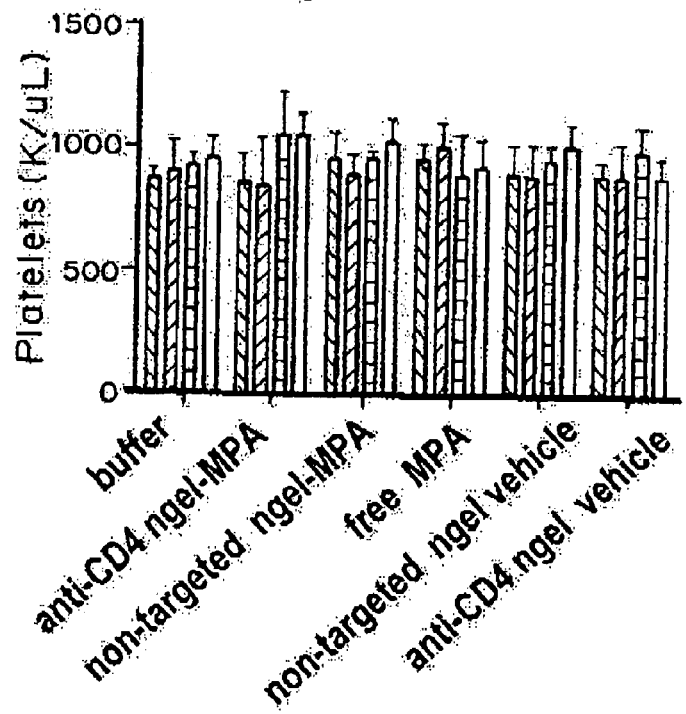
Figure 10C:
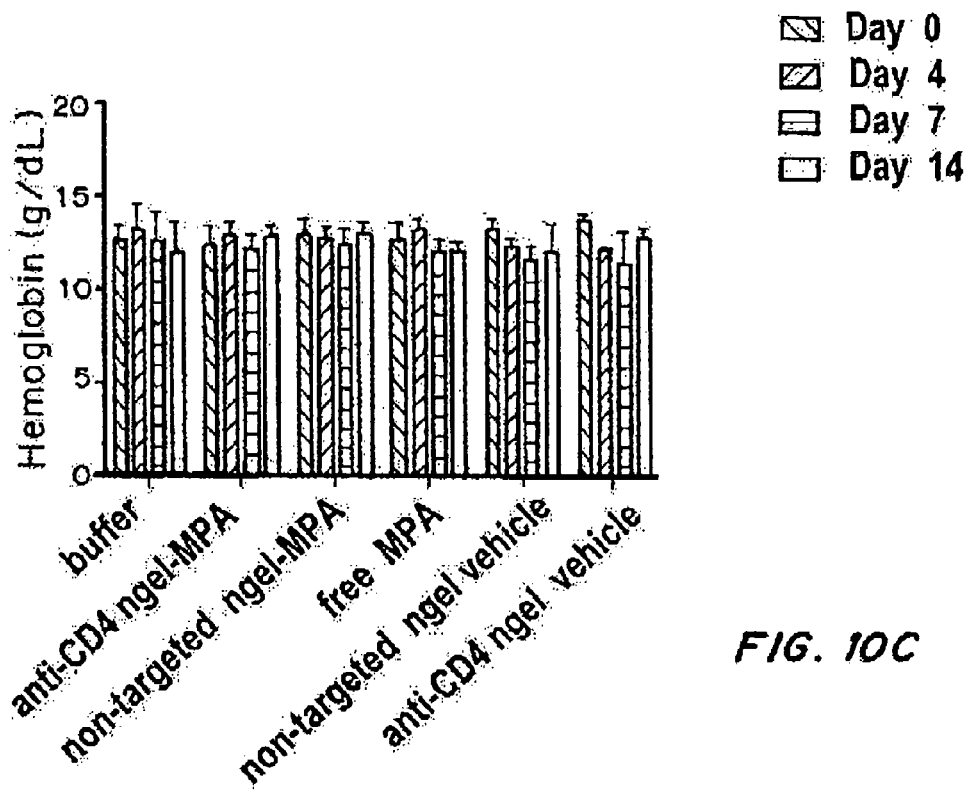
Figure 10D:
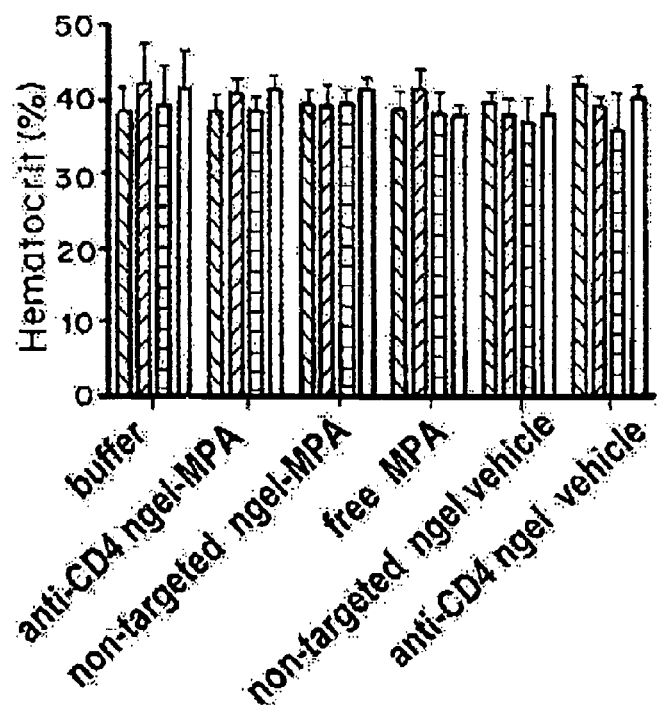

The dosing regimen used with MPA-loaded nanolipogels did not induce any apparent systemic toxicity, as measured by body mass (FIG. 9A), renal and liver functional enzyme tests (alkaline phosphatase, FIG. 9B; Alanine transferase, FIG. 9C; blood urea nitrogen, FIG. 9D, and total bilirubin (FIG. 9E) and complete blood count analysis (leukocytes, FIG. 10A; platelets, FIG. 10B; hemoglobin, FIG. 10C; hematocrit, FIG. 10D).

White blood cell, platelet, hemoglobin, and hematocrit levels were within normal physiological ranges (FIG. 10A-D). Furthermore, no liver or renal toxicities were observed. Body weight and serum concentrations for alkaline phosphatase, alanine transferase, total bilirubin, and blood urea nitrogen were normal (FIG. 10A-E).

A complete blood count (CBC) suggested that the particulate-mediated immunosuppression is not accomplished by blunt reduction in total white blood cell numbers, as the total white blood cell numbers are normal and not reduced after particulate therapy. This observation indicates immunosuppression would be observed in the activation state of immune cell subpopulations.

This data shows that MPA-loaded nanolipogels did not induce any apparent systemic toxicity. This improved safety with nanoparticle therapy stands in contrast to the side-effects often observed with conventional administration of immunosuppressants (i.e. drug not encapsulated within nanoparticles), which often leads to toxicity in the bone marrow (myelotoxicity), cytopenias, anemia, or organ damage.

Example 13

The Effect of MPA-Loaded Nanolipogels on Survival of Lupus-Prone NZB/W F1 Mice

Materials and Methods
Statistical Analysis

Statistical analyses were performed in GraphPad Prism (version 5.03). For comparisons in survival studies, the log-rank (Mantel-Cox) test was used. Experimental comparisons with multiple groups used ANOVA analysis with Bonferroni post-test. Two-tailed t-tests were used for some comparisons, as indicated in figure captions. A p-value of 0.05 or less was considered statistically significant.

Animal Studies

The in vivo therapeutic efficacy of nanolipogel particles was tested in female NZB/W F1 mice, a lupus-prone animal model. NZB/W F1 mice develop autoimmunity that resembles human lupus nephritis, with development of glomerulonephritis, anemia, and the generation of autoantibodies specific for double-stranded DNA and other self-antigens. NZB/W F1 mice were administered a life-long, single weekly intraperitoneal injection of nanoparticle therapy beginning at 18 weeks of age, before the onset of proteinuria. The single, weekly MPA dosage in nanoparticles was 0.625 mg of MPA per kg animal (mpk). Control mice received only saline buffer.

Animal studies using female NZB/W F1 mice (The Jackson Laboratory, stock #100008) were performed with the approval of the Yale University Institutional Animal Care and Use Committee. Beginning at 18 weeks of age, NZB/W F1 mice were administered a weekly intraperitoneal injection of nanoparticles or mycophenolic acid in buffer for the entirety of their life. An intraperitoneal injection was used, as opposed to intravenous tail vein injection, to prevent long-term tail vein damage from chronic injections. Mice urine was collected by bladder compression, and blood was collected via retroorbital bleed with isoflurane anesthesia. Mouse survival was continued until symptoms of cachexia (more than 5-10% body weight loss), lethargy, or poor condition warranted humane euthanization.

Nephritis occurs upon autoantibody immune complex deposition within the kidneys and subsequent infiltration by T cells, neutrophils, and macrophages. This inflammatory damage was monitored longitudinally by the presence of elevated levels of proteinuria and leukocyte esterase activity in the urine.

The efficacy of particulate therapy after the onset of established proteinuria (more than 2 consecutive daily readings of >300 mg/dL protein in urine) was also evaluated.

Results

Figure 11A:
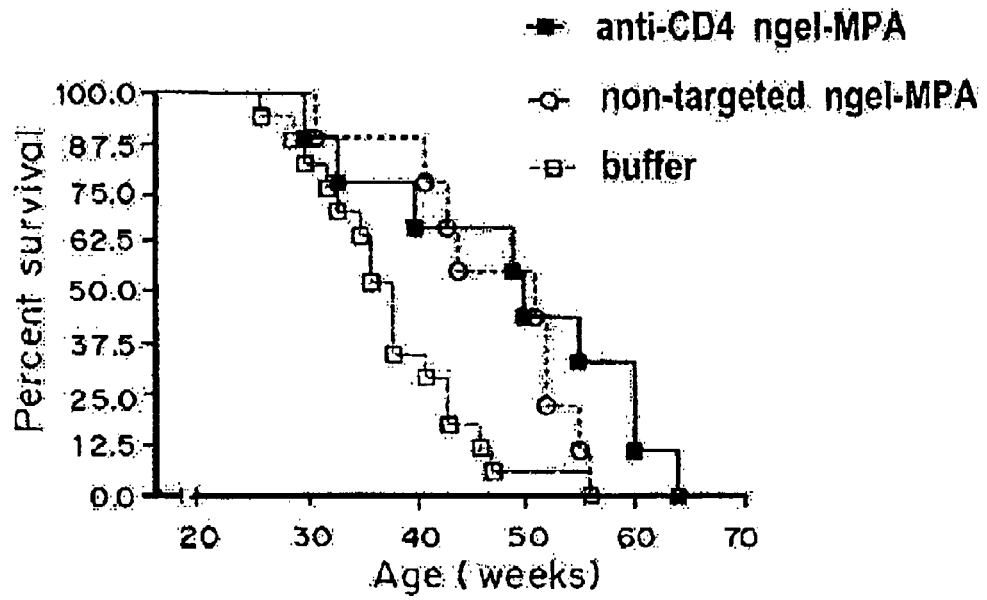
FIGS. 11A and 11B are two Kaplan-Meier survival curves (11A) and a graph of mean survival age (11B) survival over time (age in weeks) of NZB/W F1 mice were treated with a life-long, weekly dose of buffer control (-□-), anti-CD4 nanolipogel-MPA (-■-), anti-CD4 nanolipogel-vehicle (-●-), free MPA (0.625 mpk—same as nanolipogel dose) (-◇-), and free MPA (10 mpk-16× nanolipogel dose) (-*-) beginning at 18-20 weeks of age.
Figure 11A:
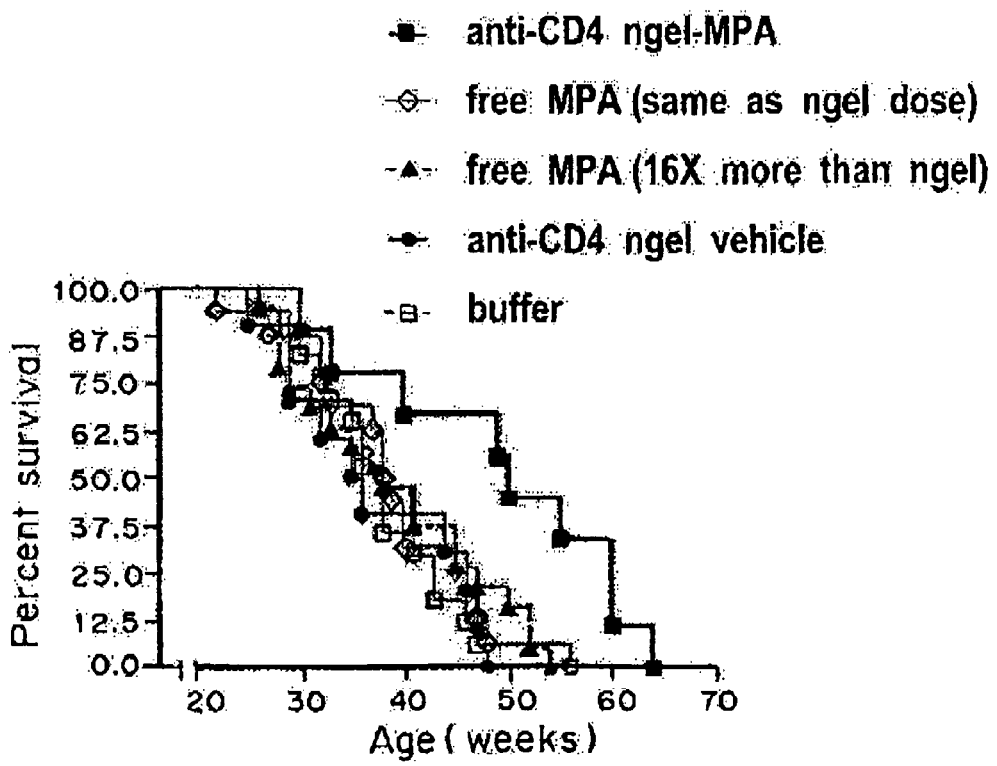
Figure 11B:
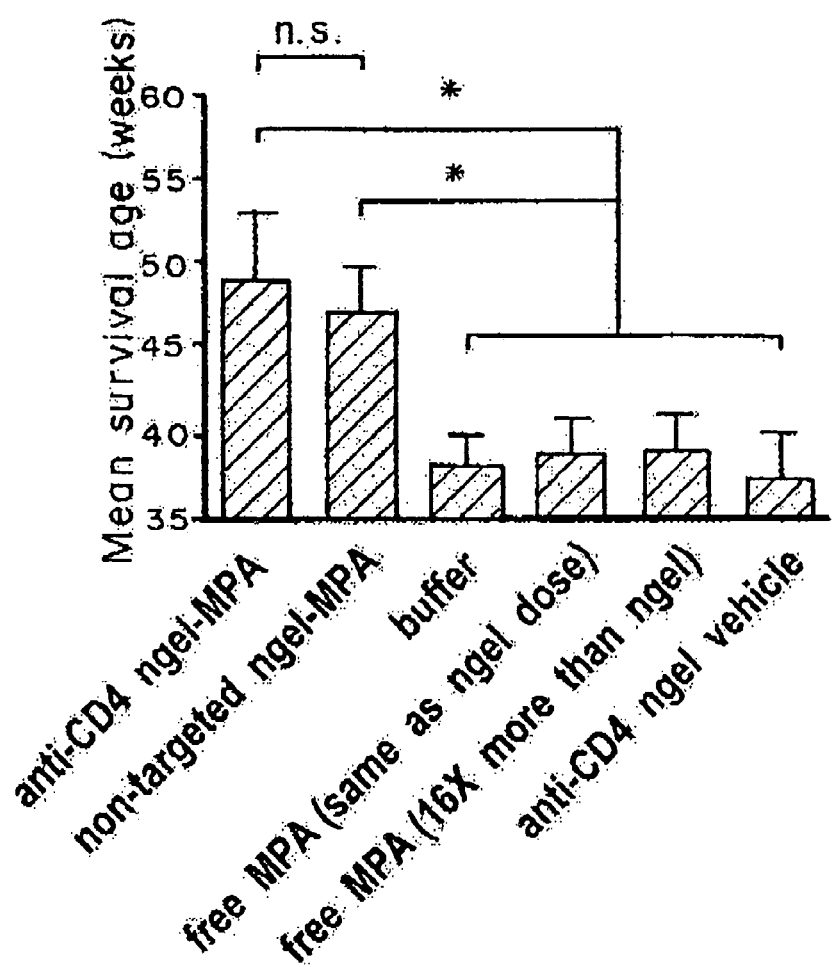
Figure 14A:
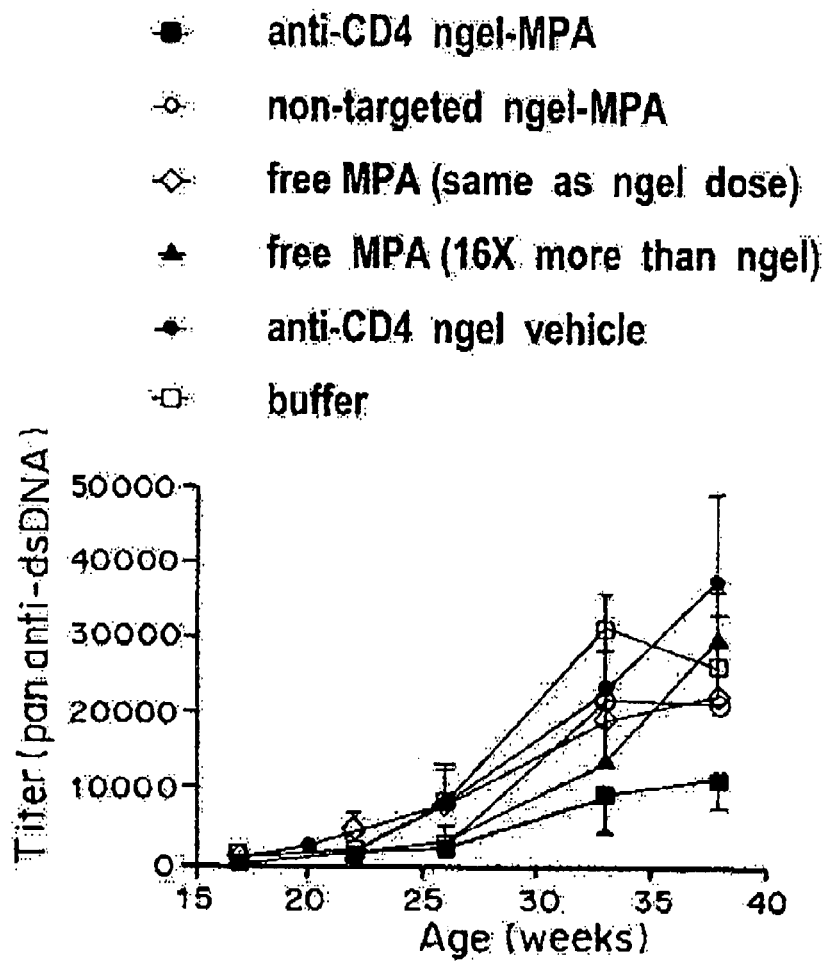
Figure 14B:
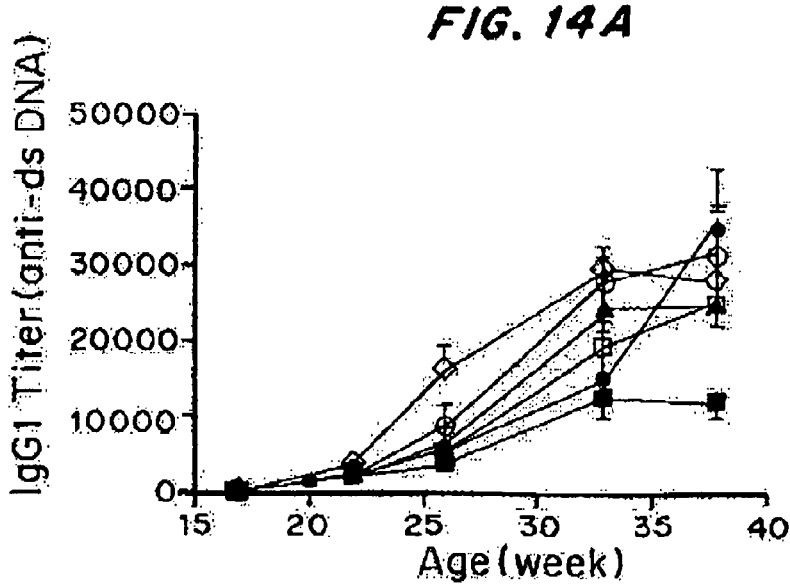
Figure 14E:
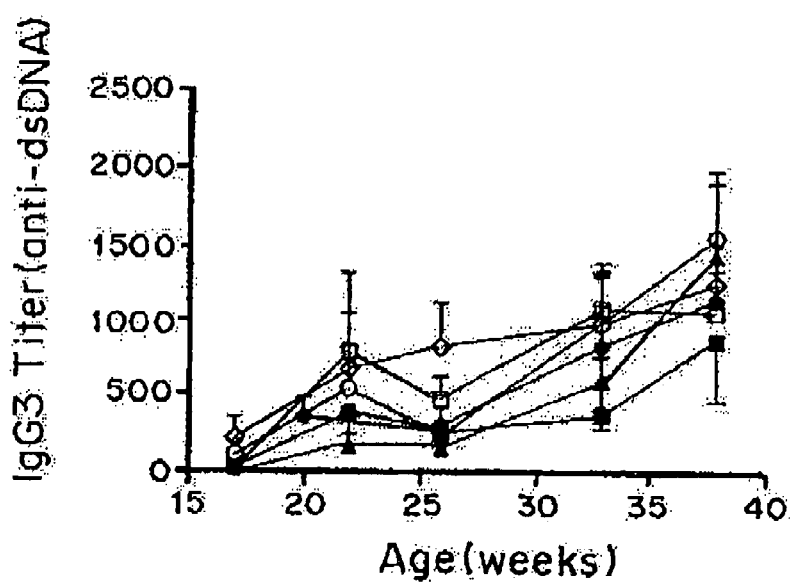

Treatment with nanoparticle therapy had a statistically significant effect on extending the median survival age of mice by 3 months. NZB/W F1 mice that received CD4 targeted particles loaded with mycophenolic acid had a median survival time of 50 weeks compared to only 38 weeks for mice receiving no therapeutic immunosuppression. (FIG. 11A, 14B). The delivery of mycophenolic acid in particles was critical to achieving therapeutic benefit. The administration of an equivalent MPA dosage given soluble in buffer (referred to as "free MPA") at 0.625 mpk had no effect on extending survival (FIG. 11B). When the free MPA dosage was increased by 16-fold, to 10 mpk, there still was no improvement in survival. (FIG. 11B).

The data shows that all treatment groups that received MPA-loaded nanoparticles had extended median survival times. CD4-targeted MPA-loaded particles extended survival to approximately 50 weeks (p<0.0083), and non-targeted MPA-loaded particles extended survival to approximately 51 (P<0.0304) (FIGS. 11A and 11B). Thus nanoparticles uniquely enhance the immunosuppression of MPA, compared to what is typically achieved with much higher and more frequent doses of free MPA (30 to 100 mg/kg/day) (Ramos, et al., Nephrol Dial Transplant, 2003. 18(5):878-83 (2003); Lui, et al., Lupus, 11(7):411-8 (2002)) and that nanoparticulate therapy was not dependent on direct targeting of nanoparticles to CD4 T cells. The in vivo use of nanoparticles was safe—no acute toxicity was observed when tested in C57BL/6 wild type mice, and no chronic toxicity was obvious in NZB/W F1 mice during the year-long therapeutic studies.

Figure 12A:
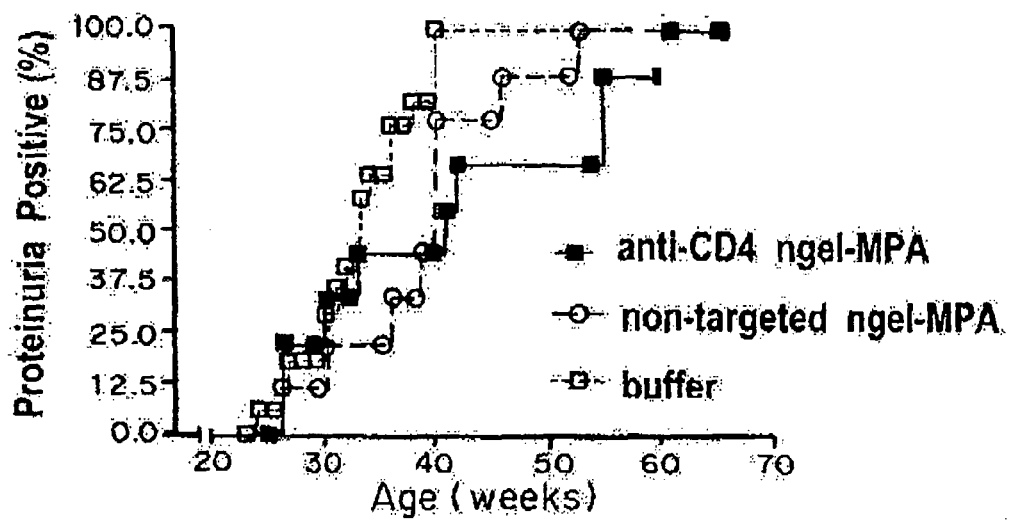
FIGS. 12A and 12B are graphs of proteinuria (% positive) (12A), leukocyte esterase (% positive) (12B) over time in weeks. The top graphs in 15A and 15B compares buffer control (-□-), anti-CD4 nanolipogel-MPA (-○-), non-targeted Nanolipogel-MPA (-●-). The bottom graphs in 12A and 12B compares buffer control (-□-), anti-CD4 nanolipogel-MPA (-■-), anti-CD4 nanolipogel-vehicle (-●-), free MPA (0.625 mpk—same as nanolipogel dose) (-◇-), and free MPA (10 mpk-16× nanolipogel dose) (-*-).
Figure 12A:
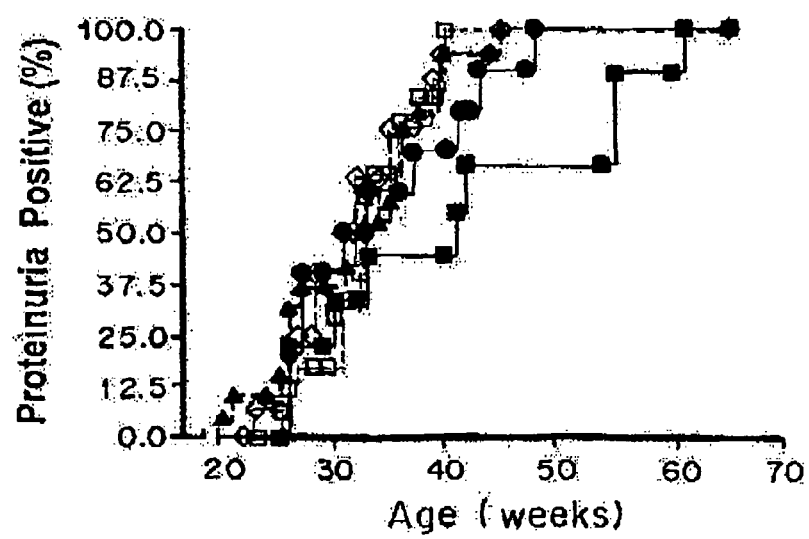
Figure 12B:
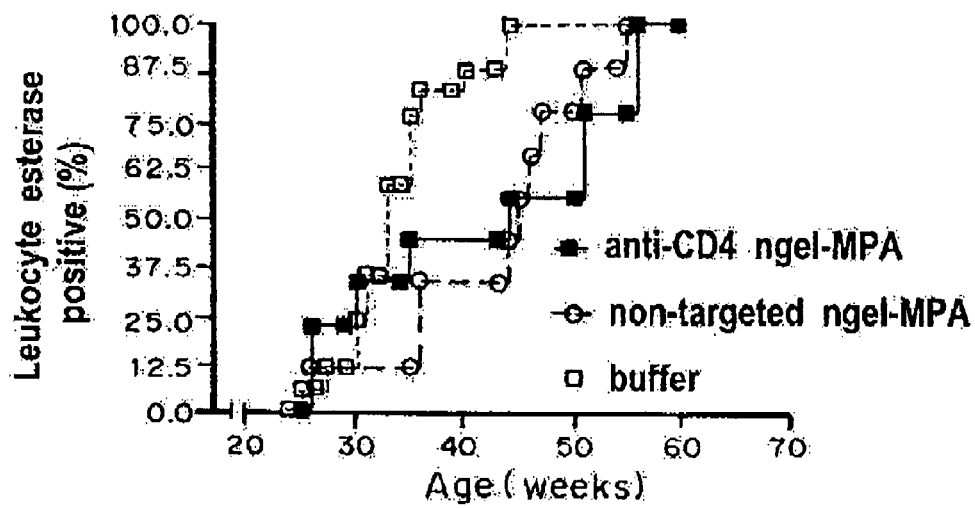
Figure 12B:
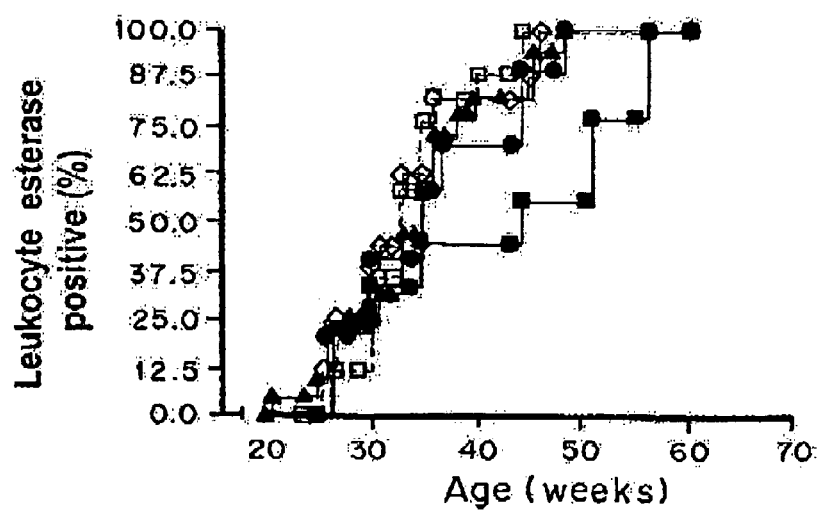
Figure 12C:
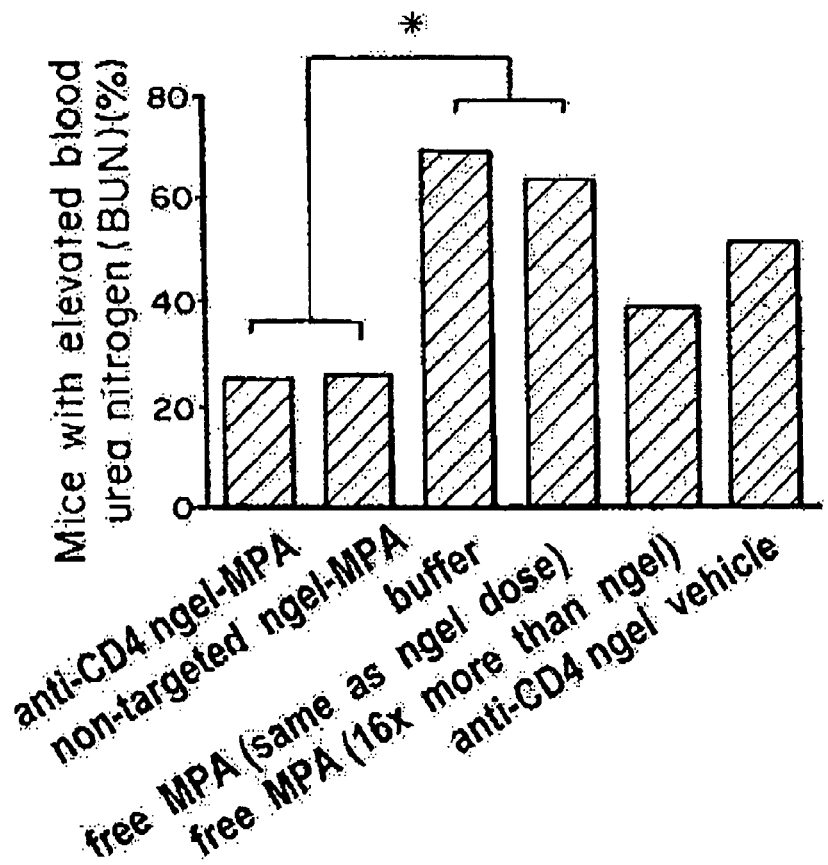
FIG. 12C is a bar graph showing elevated blood urea nitrogen (BUN) (as a % elevated over the physiological reference range of 18-29 mg/dL) following treatment with anti-CD4 nanolipogel-MPA, non-targeted Nanolipogel-MPA, buffer, 0.625 mpk free MPA, 10 mpk free MPA, or anti-CD4 Nanolipogel vehicle.
Figure 12D:
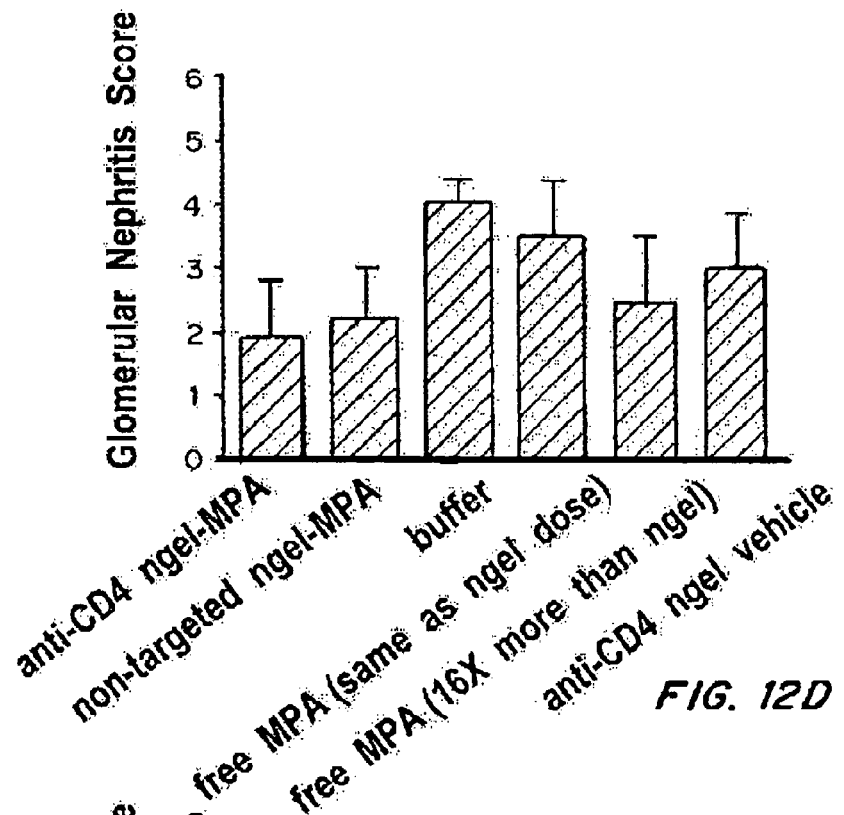
FIGS. 12D and 12E are bar graphs showing glomerular nephritis score (12D) and interstitial nephritis score (12E) for mice treated with anti-CD4 nanolipogel-MPA, non-targeted Nanolipogel-MPA, buffer, 0.625 mpk free MPA (same as nanolipogel dose), 10 mpk free MPA (16× nanolipogel dose), or anti-CD4 Nanolipogel vehicle.
Figure 12E:
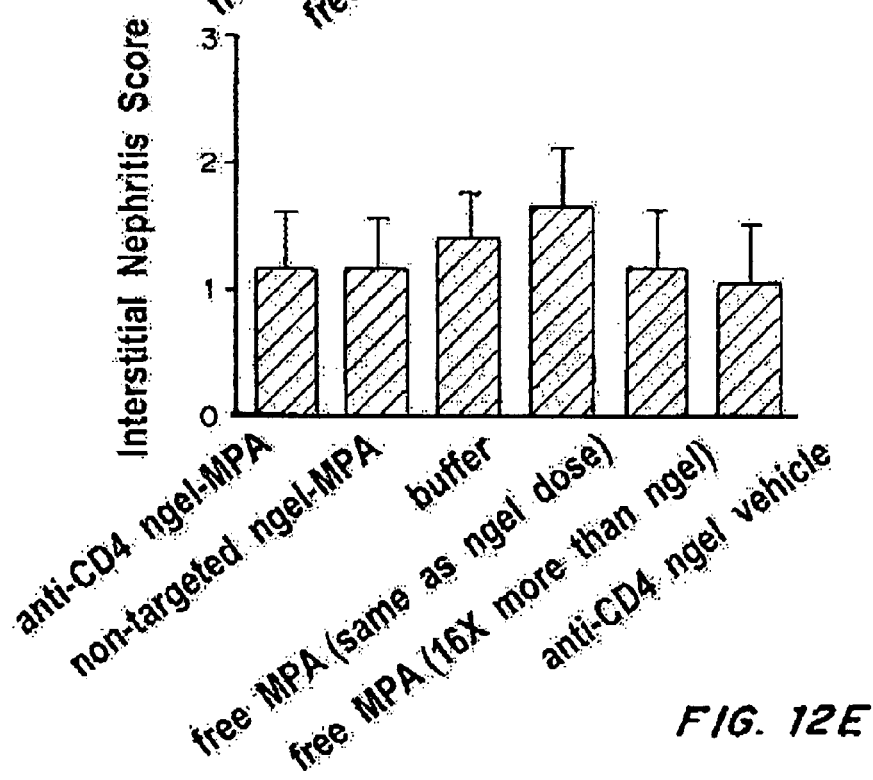
Figure 12F:
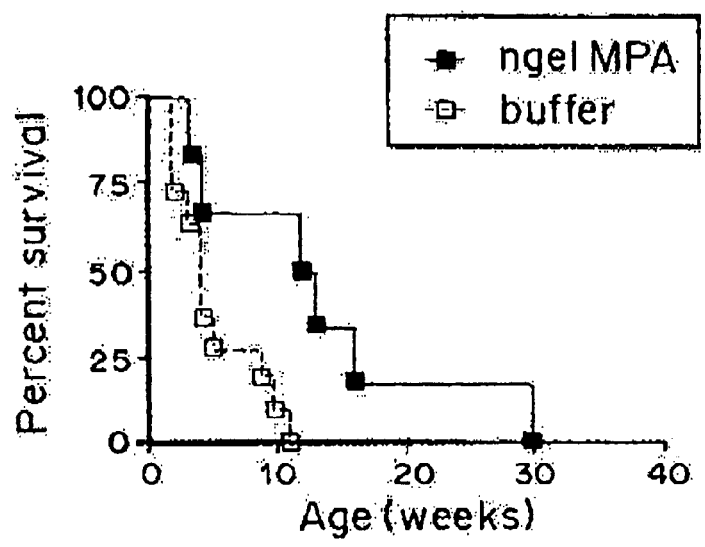
FIG. 12F is a Kaplan-Meier Curve showing percent survival over age for Nanolipogel MPA compared to buffer.

Nanogels also protected against nephritis. The extension in survival with particulate therapy correlated with a delay in nephritis, which is the primary cause of mortality in NZB/W F1 mice. Mice receiving prophylactic treatment particulate therapy had delayed onset of proteinuria (FIG. 12A) and presence of leukocyte esterase in the urine (FIG. 12B) compared to free drug and buffer treatments. Renal function, as measured by blood urea nitrogen (BUN) levels, was also preserved in particulate treated mice (FIG. 12C). The percentage of mice with abnormally elevated blood urea nitrogen (BUN) levels (greater than 18-29 mg/dL), which is an indicator of impaired renal function, was lower in 36-40-weeks-old mice Consistent with these observations, histopathologic evaluation of kidneys from mice at approximately 36-40 weeks of age verified that particulate-treated groups had decreased kidney damage and inflammation (FIGS. 12D and 12E). Treatment extended survival (FIG. 12F).

Figure 12G:
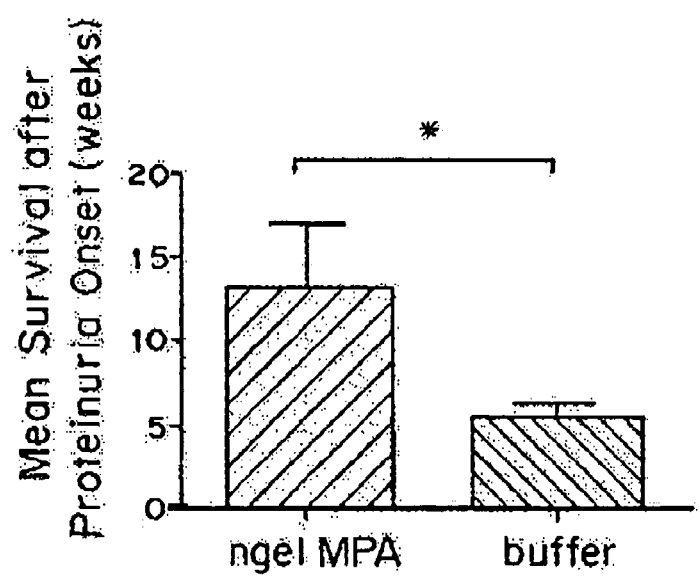
FIG. 12G is a bar graph showing mean survival after proteinuria onset (weeks) for Nanolipogel compared to buffer. Average mouse age of proteinuria onset for nanolipogel MPA of 37.2±5.9 weeks compared to buffer of 36.3±5.2 weeks, p<0.05 by Mantel-Cox (log-rank) test.

Mice that began weekly particulate therapy after the onset of proteinuria also had extended survival (FIG. 12G). Survival time lasted 12 weeks with particles compared to only 4 weeks with buffer (p<0.0198) when administered to mice after the onset of proteinuria, indicating that the particulate therapy is still efficacious even under more stringent disease conditions.

Example 14

Nanolipogel Particle Biodistribution Studies

The data discussed above shows that a CD4 directed nanoparticle therapy is successful in preventing T-dependent autoimmunity by exclusively abrogating CD4 T cell activation or proliferation. However, nanoparticles without any CD4 targeting also provided therapeutic benefit in vivo. To investigate a basis for this therapeutic benefit without CD4 targeting, the in vivo biodistribution of nanoparticles was analyzed.

Materials and Methods

Particle Biodistribution Studies

Rhodamine loaded nanolipogels were prepared and then injected intraperitoneally into mice. For organ biodistribution and histology studies, 12-week-old NZB/W F1 mice were used. Organs were harvested, weighed, and imaged with the IVIS imaging system to obtain quantitative rhodamine fluorescence measurements. For histological analysis, spleens were snap-frozen in OCT embedding medium and then sectioned on a cryotome onto charged slides. Sections were fixed in ice cold acetone for 10 minutes, and subsequently stained with antibodies for CD4, CD19, or F4/80. Tissue sections were imaged on a Nikon TE-2000 microscope. FITC channel: 470/40, 525/50; rhodamine channel: 540/25, 605/55; Alexa647 channel: 620/60, 700/75.

The extent to which different lymphocyte and antigen presenting cell subsets were associated with nanoparticles was also investigated.

Flow Cytometer Analysis

For flow cytometric measurement of particle binding to immune cells, the analysis was performed in C57BL/6 mice immunized with $1 \times 10^6$ sheep red blood cells (Colorado Serum Company). Seven days after immunization, rhodamine-labeled particles were injected, and 2-3 hr later, cells from the spleen, lymph nodes (pooled inguinal, brachial, and cervical), and bone marrow were harvested and then analyzed the same day on an LSR II flow cytometer.

Peripheral blood lymphocytes were collected in a solution of 50 U/mL heparin and isolated with Ficoll gradient separation. Splenocytes were harvested and red blood cells were removed with ACK lysis buffer. Lymphocytes were blocked with 1% fetal bovine serum (FBS) in PBS, and then stained with the following combinations: for T cells-CD4 (clone RM4-5), CD8, CD62L, CD44, PD-1, and CXCR5-biotin; for B cells-B220, CD138, IgD, GL-7, PNA-biotin (Vector Labs), and MHC II; and for innate antigen presenting cells-F4/80, CD11c, PDCA-1, CD40, CD80, and MHC II (all antibodies from BD Biosciences or eBioscience). Streptavidin Pe-Cy7 (Invitrogen) was used as a detection agent for biotinylated antibodies.

Cells were fixed with 2% paraformaldehyde and then analyzed on an LSRII flow cytometer (BD Biosciences). For in vitro proliferation studies, T cells were labeled with 0.5 µM CFDA-SE (Invitrogen) in PBS for 10 min at 37° C. at a concentration of $4 \times 10^6$ cells/mL, and then washed twice with RPMI-1640 complete media (10 mM HEPES, 1 mM L-glutamine, 100 U/mL penicillin, 100 µg/mL streptomycin, 50 µM β-mercaptoethanol), with 10% heat inactivated FBS. For intracellular IFN-γ staining, $1 \times 10^6$ splenocytes were first stimulated with 20 ng/mL PMA and 2 µg/mL ionomycin for 3 hr in brefeldin A (BD Bioscience) at 37° C. in complete RPMI-1640 media. Cells were labeled for extracellular CD4 and CD25, treated with fixation/permeabilization buffer (eBioscience), and then stained with antibodies for Foxp3 and IFN-γ according to manufacturer's specifications. Cells analyzed for intracellular IFN-γ expression were prestimulated with PMA and ionomycin for 3 hr in brefeldin A (BD Bioscience) before staining.

Results

Figure 13A:
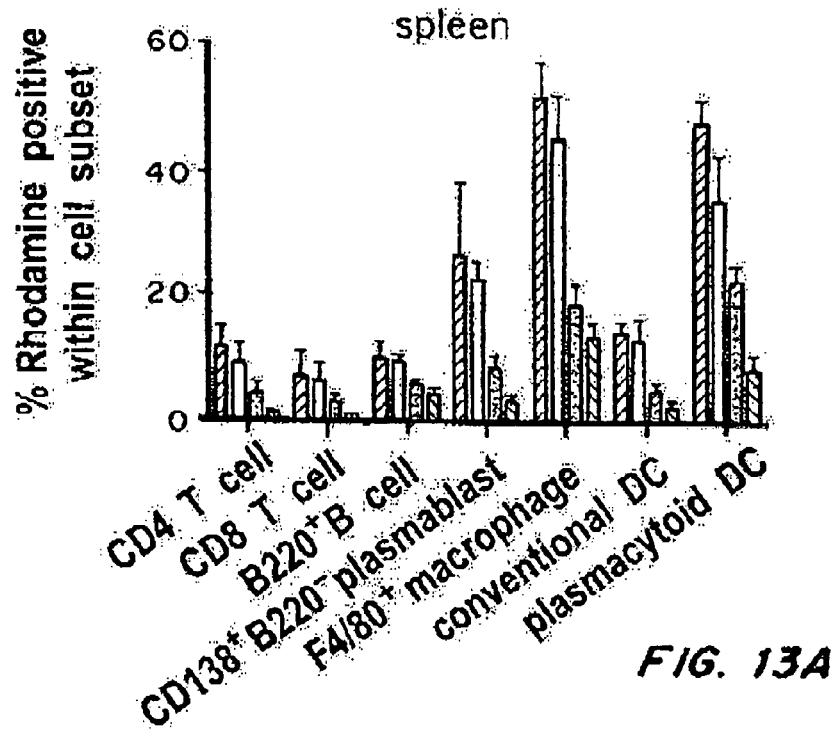
FIGS. 13A-13B are bar graphs of percent rhodamine positive cells within cell subset for spleen (13A) and lymph node (13B) treated with anti-CD4 nanolipogel (solid); non-targeted Nanolipogel (grey); free rhodamine (open) and PBS (horizontal stripes).
Figure 13B:
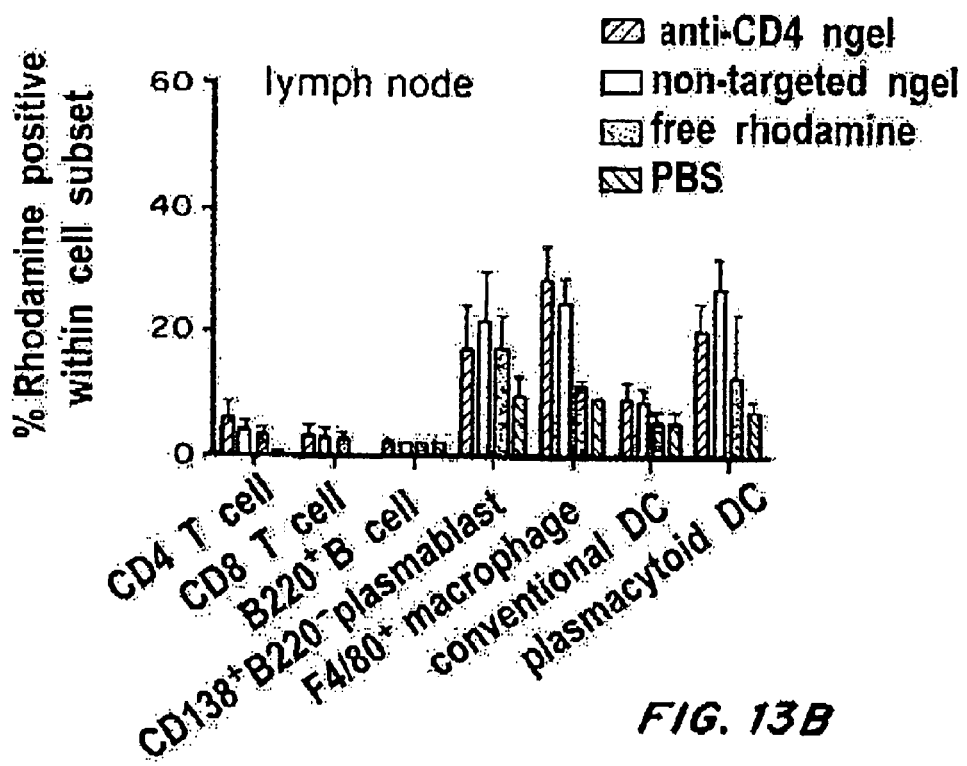
Figure 13C:
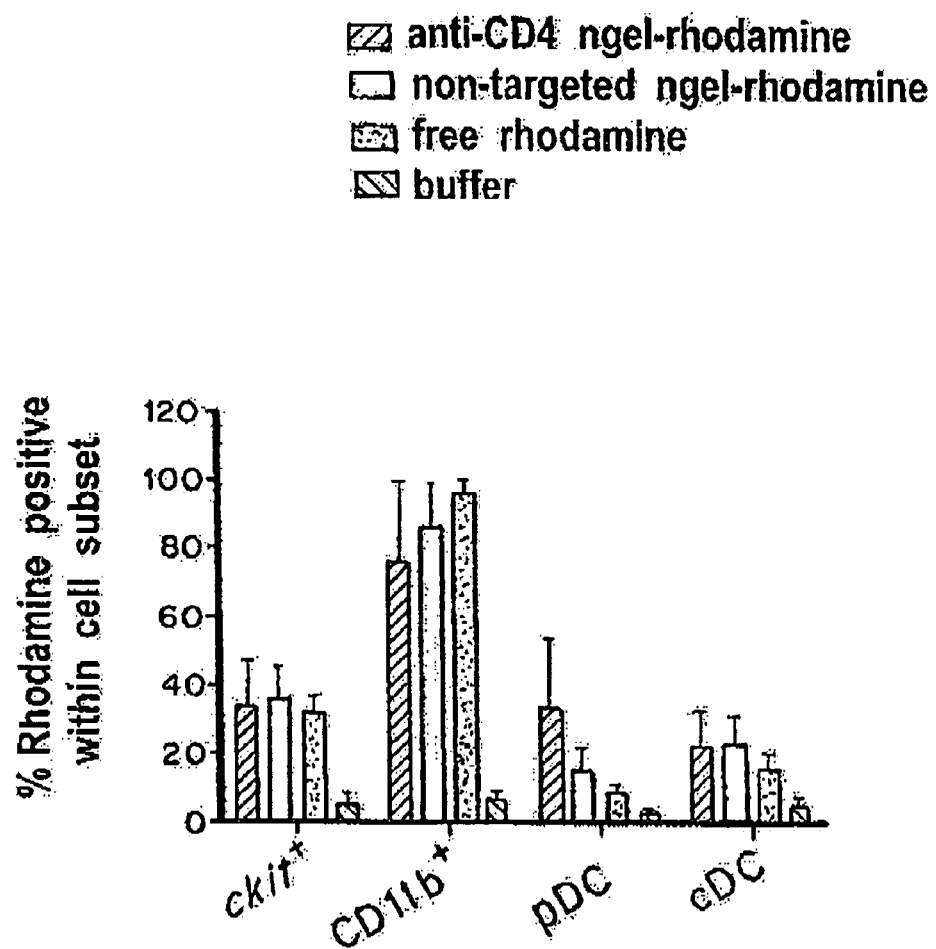
FIG. 13C is a bar graph showing the % rhodamine positive cells within cell subset for ckit+ cells, CD11b+ cells, pDC cells, and cDC cells treated with anti-CD4 nanolipogel (solid); non-targeted Nanolipogel (grey); free rhodamine (open) and PBS (horizontal stripes).
Figure 13D:
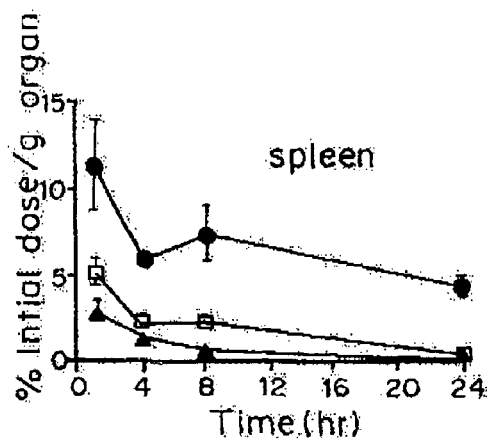
FIGS. 13D-13J are lines graphs of the % initial dose/g organ for anti-CD4 rhodamine Nanolipogel (-●-), non-targeted rhodamine Nanolipogel (-□-), and free rhodamine (-△-) for spleen (13D), heart (13E), lung (13F), kidney (13G), liver (13H), pancreas (13I), and serum (13J).
Figure 13E:
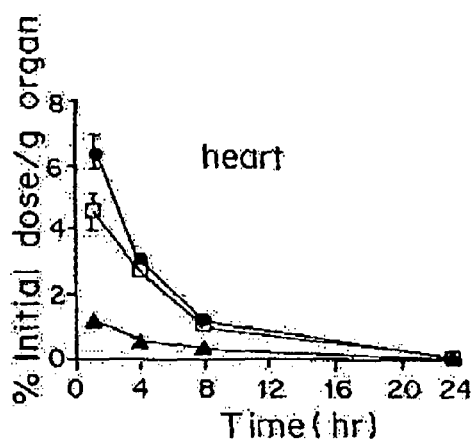
Figure 13F:
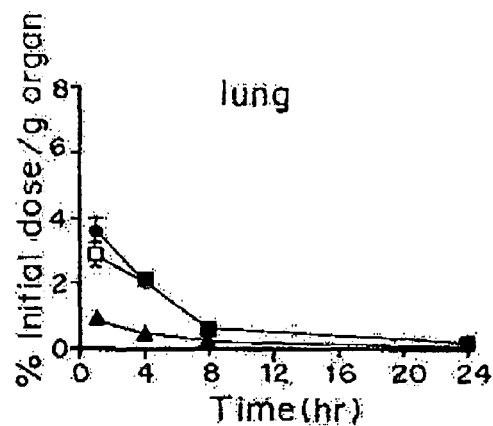
Figure 13G:
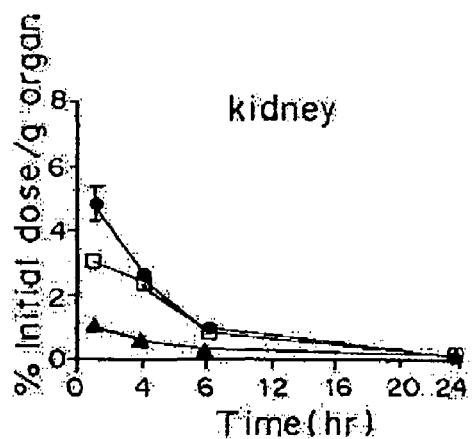
Figure 13H:
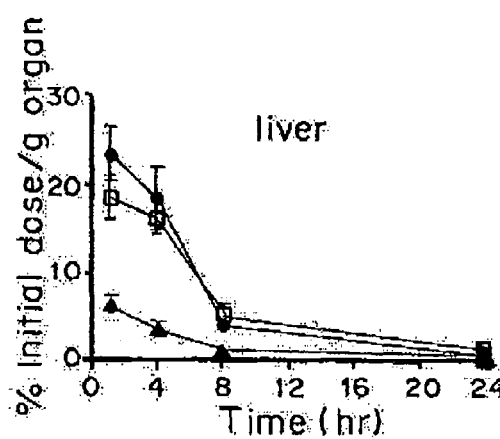
Figure 13I:
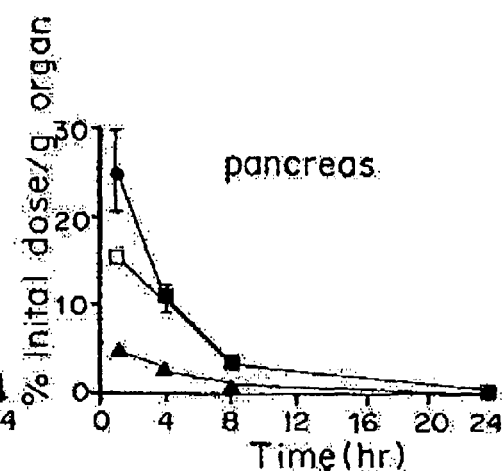
Figure 13J:
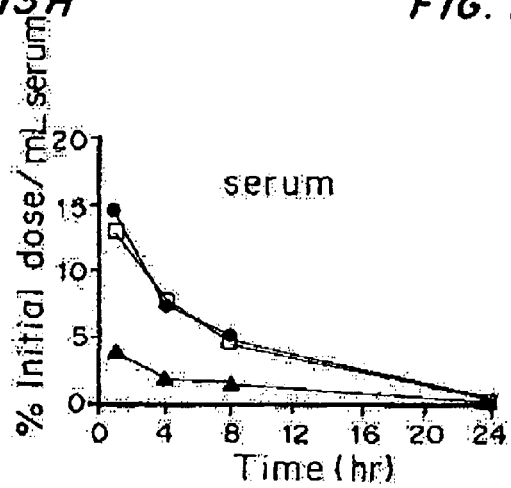

Flow cytometer analysis demonstrated that CD4 targeted nanoparticles associate with CD4 T cells in the spleen. Notably, splenic macrophages and both conventional and plasmacytoid dendritic cells also internalized nanoparticles (FIG. 13A). Histological examination of spleens showed that nanoparticles could localize to the splenic T cell zone and red pulp after 2-3 hours. T and B220+ cells associated with particles, with the greatest binding (based on the percentage of the cell subset) observed with dendritic cells, macrophages, and plasmablasts (FIGS. 13A and 13B). Furthermore, nanoparticles also trafficked to the bone marrow, and could be internalized by bone marrow resident plasmacytoid dendritic cells and CD11b macrophages (FIG. 13C).

Nanolipogels Target Immune Cell Subsets In Vivo

Regardless of targeting, nanogels had greater accumulation in the spleen, kidneys, liver, heart, lung, and pancreas compared to free rhodamine (FIG. 13D-13J). This trend is consistent with other reports that show particulate drug delivery systems can increase the bioavailability of compounds (Hillery, et al., *Drug delivery and targeting for pharmacist and pharmaceutical scientists*, New York City, N.Y., Taylor and Francis (2001)). Analysis of fluorescently labeled particles injected into mice showed that nanoparticles, even without CD4 targeting capability, persisted longer in tissue compared to dye administered soluble in buffer (spleen, 13D; heart 13E; lung, 13F; kidney, 13G; liver, 13H; pancreas, 13I). This enhanced distribution time of particles and their encapsulants in tissue is consistent with reports that demonstrate that nanoparticle drug delivery systems can better prolong the bioavailability of compounds.

Example 15

In Vivo Immune Responses to Particulate Therapy

To further characterize the results obtained with nanoparticulate therapy, the immune responses in all treatment groups was analyzed.

Materials and Methods
Antibody ELISAs

As an initial proxy for evaluating these cellular responses, the levels of anti-double stranded (ds) DNA antibodies in the serum were monitored as a potential explanation for particulate-mediated protection against nephritis. Autoantibodies promote pathology, and many reports have shown that amelioration of autoantibody titers can lead to protection from nephritis.

For dsDNA ELISAs, a coating layer of 10 μg/mL methylated BSA (Calbiochem) in bicarbonate buffer was adsorbed onto a high-binding 96-well plate, followed by incubation with 10 μg/mL of calf thymus DNA (Sigma). 1% BSA was used as a blocking agent and diluent, and 0.05% TWEEN®-20 in PBS was used as a wash buffer. Horseradish peroxidase-conjugated antibodies for mouse-specific pan-IgG (ICL Labs), IgG1, IgG2a, IgG2b, and IgG3 (Invitrogen) were used for detection, followed by TMB (KPL) substrate development.

Results

Figure 15A:
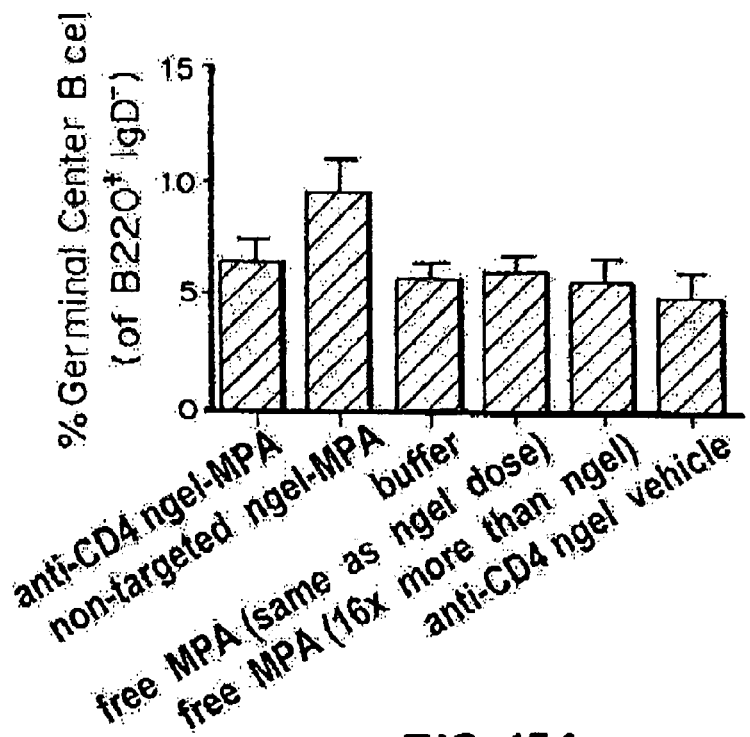
FIGS. 15A-15B are bar graphs of percentage of splenic germinal center B cells (of B22$^+$IgD$^-$) (15A) and T follicular helper cells (defined as CXCR5$^+$PD–1$^+$ activated CD4 T cells (TfH CD26L$^{lo}$, CD44$^{hi}$) in 36-40-weeks-old NZB/W F1 mice that received prophylactic therapy with anti-CD4 nanolipogel-MPA, non-targeted Nanolipogel-MPA, buffer, 0.625 mpk free MPA (same as nanolipogel dose), 10 mpk free MPA (16× nanolipogel dose), or anti-CD4 Nanolipogel vehicle. The sample size is n=6 to 15 animals per group. Error bars represent the standard error measurement.
Figure 15B:
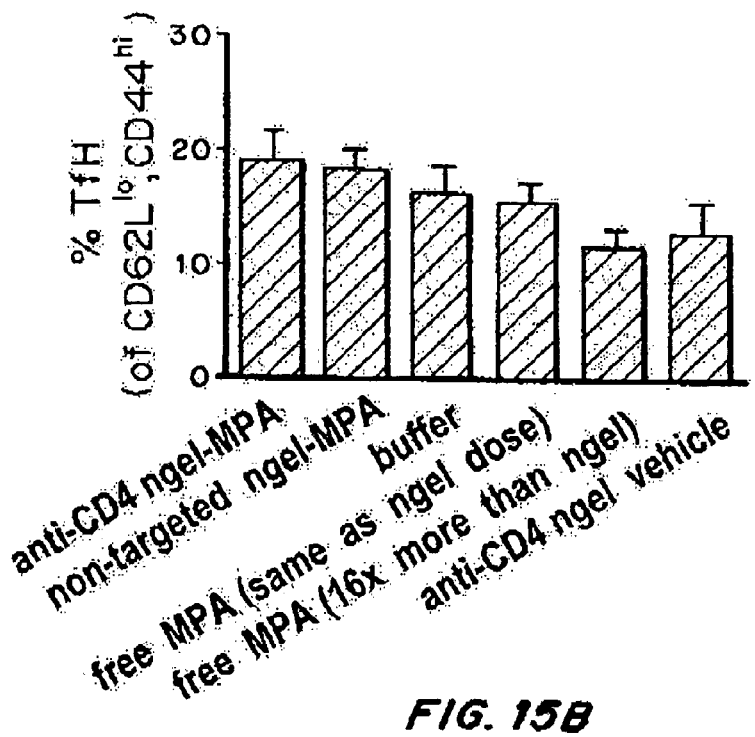
Figure 15C:
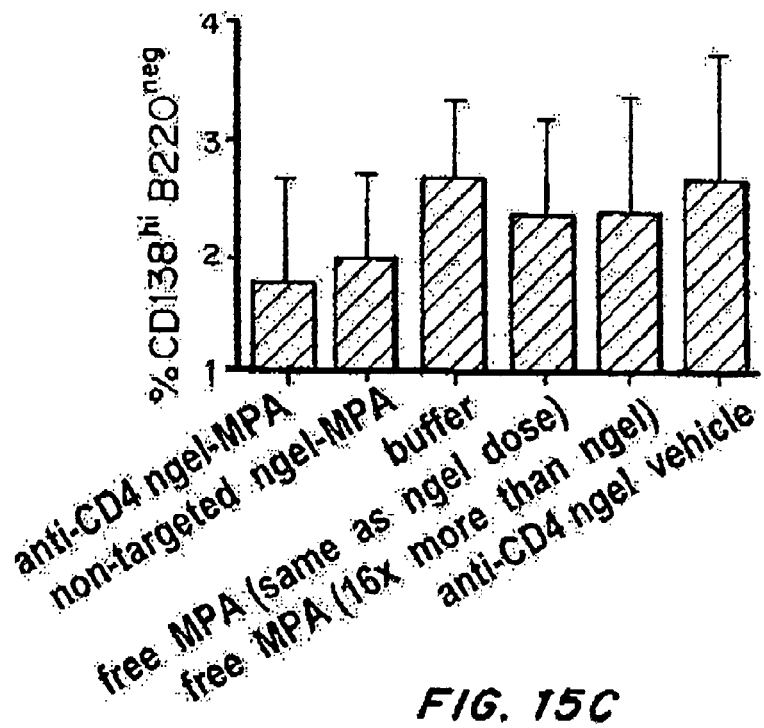
FIGS. 15C-15E are bar graphs the percentage of peripheral blood lymphocytes: plasmablasts (% CD138$^{hi}$B220$^{neg}$) (18C), activated CD4 T cells (% CD62L$^{low}$, CD44$^{hi}$ of CD4 T cells) (15D), and activated CD8 T cells (% CD62L$^{lo}$, CD44$^{hi}$ of CD8 T cells) (15E), in 36-40-weeks-old NZB/W F1 mice that received prophylactic therapy with anti-CD4 nanolipogel-MPA, non-targeted Nanolipogel-MPA, buffer, 0.625 mpk free MPA (same as nanolipogel dose), 10 mpk free MPA (16× nanolipogel dose), or anti-CD4 Nanolipogel vehicle beginning at 18-20 weeks of age. The sample size is n=6 to 15 animals per group. Error bars represent the standard error measurement.
Figure 15D:
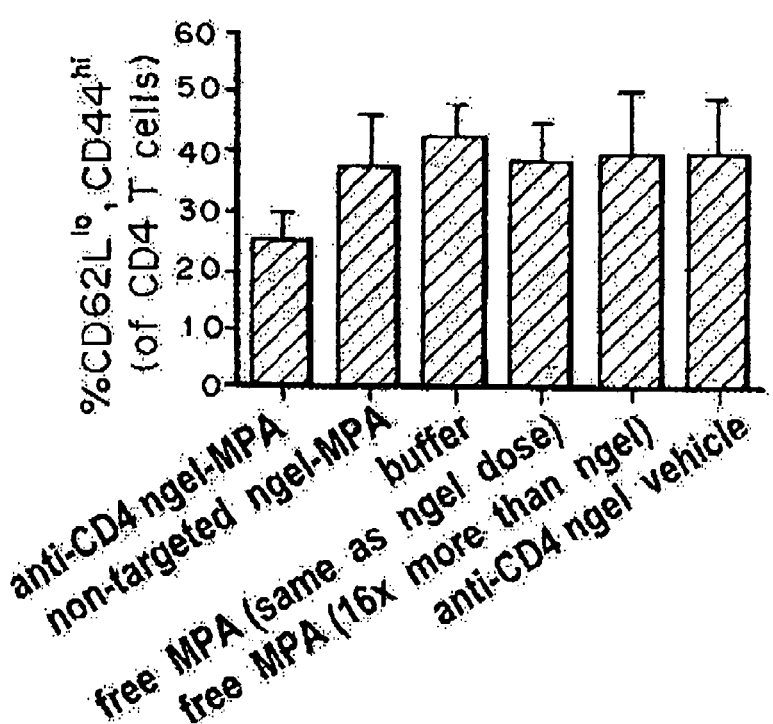
Figure 15E:
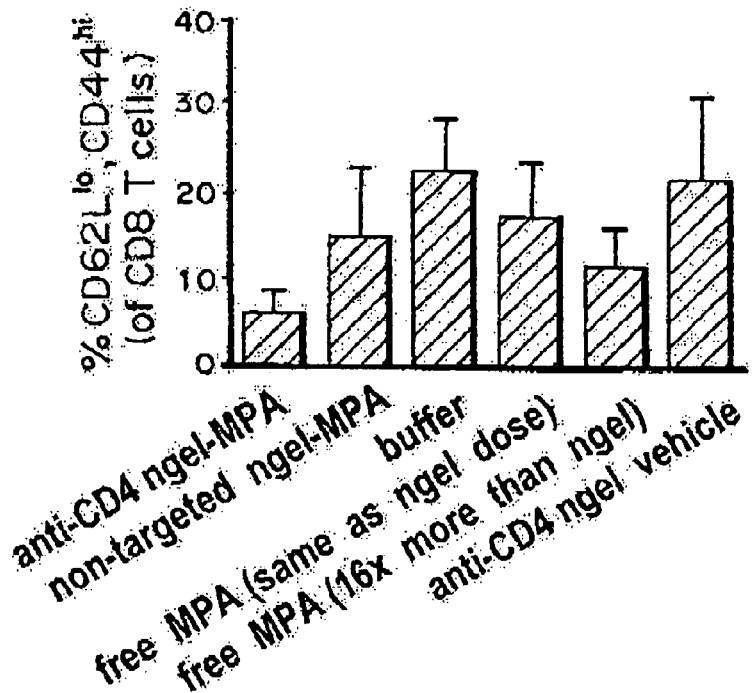

White blood cell counts were not reduced after 4 consecutive, daily doses of nanogels in wild type mice, and surprisingly, at the dosage used with the nanoparticle therapy, there was only marginal inhibition in the development of anti-ds DNA antibodies (FIG. 14A-14E). At 36-40 weeks of age, no differences were observed in the percentage of splenic germinal center B cells or CD4 T follicular helper (FIG. 15A-15B). Furthermore, there were only mild reductions in the percentages of peripheral blood $CD138^{hi}B220^{lo}$ antibody-secreting B cell (FIG. 15C). These results indicate that the reduction in autoantibody responses was not the primary consequence of nanoparticle therapy.

Figure 16A:
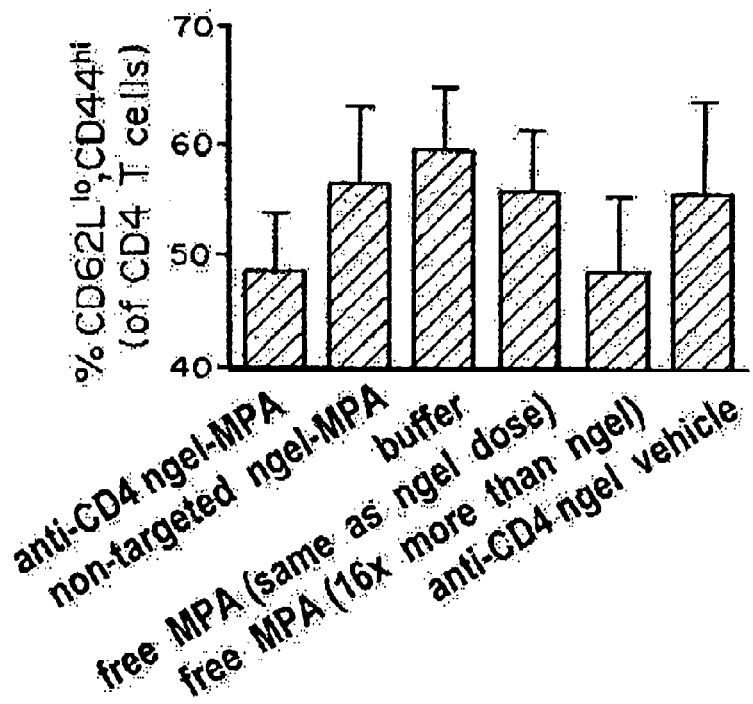
FIGS. 16A-16D are bar graphs of splenocytes were harvested from 36-40-weeks-old NZB/W F1 mice that received weekly therapy beginning at 19-20 weeks of age. The graphs show: activated CD4 T cells (% CD62L$^{low}$, CD44$^{hi}$ of CD4 T cells) (16A), and naive CD4 T cells (% CD62L$^{high}$, CD44$^{low}$ of CD4 T cells) (18D) (16B), % interferon gamma positive (of CD4 T cells) (16C), regulatory T cells (% Foxp3 CD26 (of CD4 T cells) (16D), following treatment with anti-CD4 nanolipogel-MPA, non-targeted Nanolipogel-MPA, buffer, 0.625 mpk free MPA (same as nanolipogel dose), 10 mpk free MPA (16× nanolipogel dose), or anti-CD4 Nanolipogel vehicle. *p<0.05 by two-tailed t-test. d) No differences were observed in CD4 T regulatory cells. The sample size is n=6 to 15 animals per group. Error bars represent the standard error measurement.
Figure 16B:
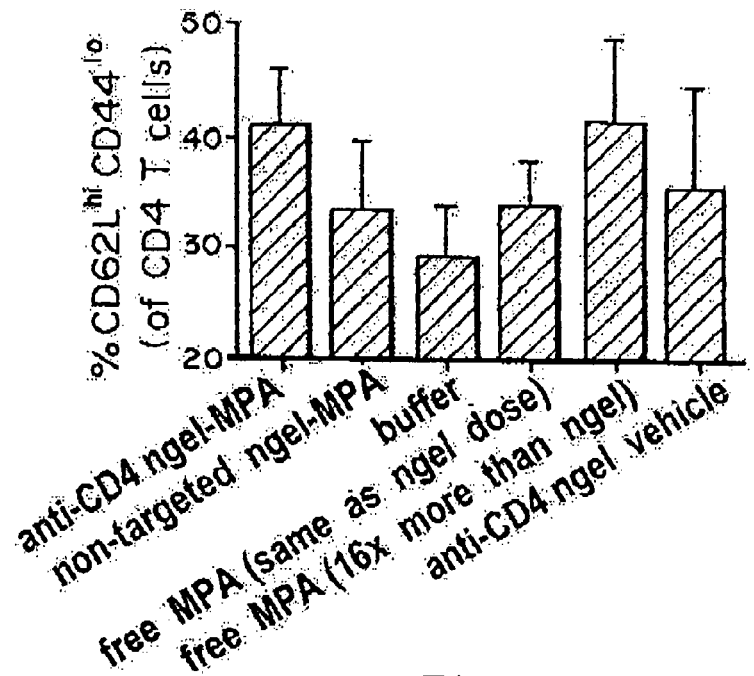
Figure 16C:
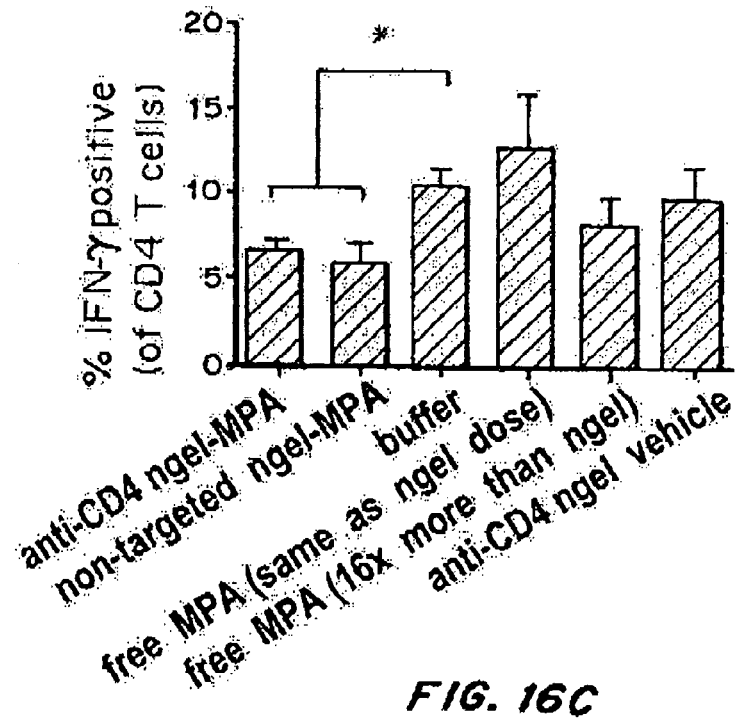
Figure 16D:
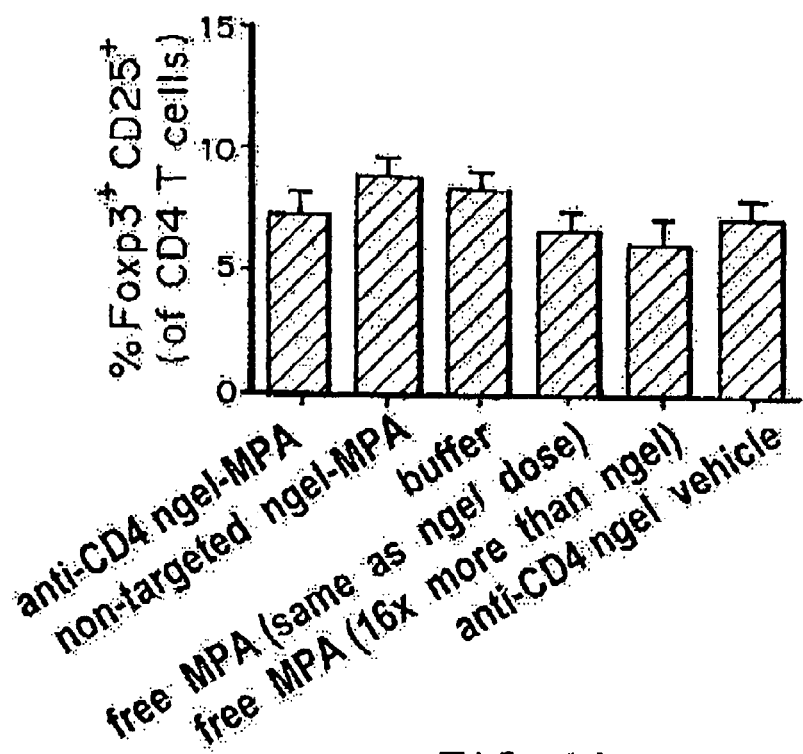

Inflammatory responses by CD4 T cells are known to worsen disease; for example, Th1 responses are often elevated in both human patients and mouse models of lupus. The data shows that percentage of splenic IFN-γ producing CD4 T cells was statistically significantly reduced by approximately 2-fold, from 10% of CD4 T cells (in untreated controls) to 5% of CD4 T cells (FIG. 16A). This correlated with mild reductions in the percentage of activated splenic and peripheral blood CD4 T cells ($CD62L^{lo}CD44^{hi}$) (FIGS. 16B and 16B). This reduction in inflammatory CD4 T cell responses did not correlate with any expansion in CD4 T regulatory (T reg) cell numbers (FIG. 16D). The percentage of splenic IFN-γ producing CD4 T cells was significantly reduced by approximately 2-fold (FIG. 16C), from 10% of CD4 T cells in untreated controls to 5% with particle treatment. Collectively, these data indicate MPA-loaded nanolipgel therapy modulates T cell phenotype without causing lymphopenia, and that immunosuppression occurs through modulating immune cell function or activation state rather than by lymphodepletion.

Figure 17A:
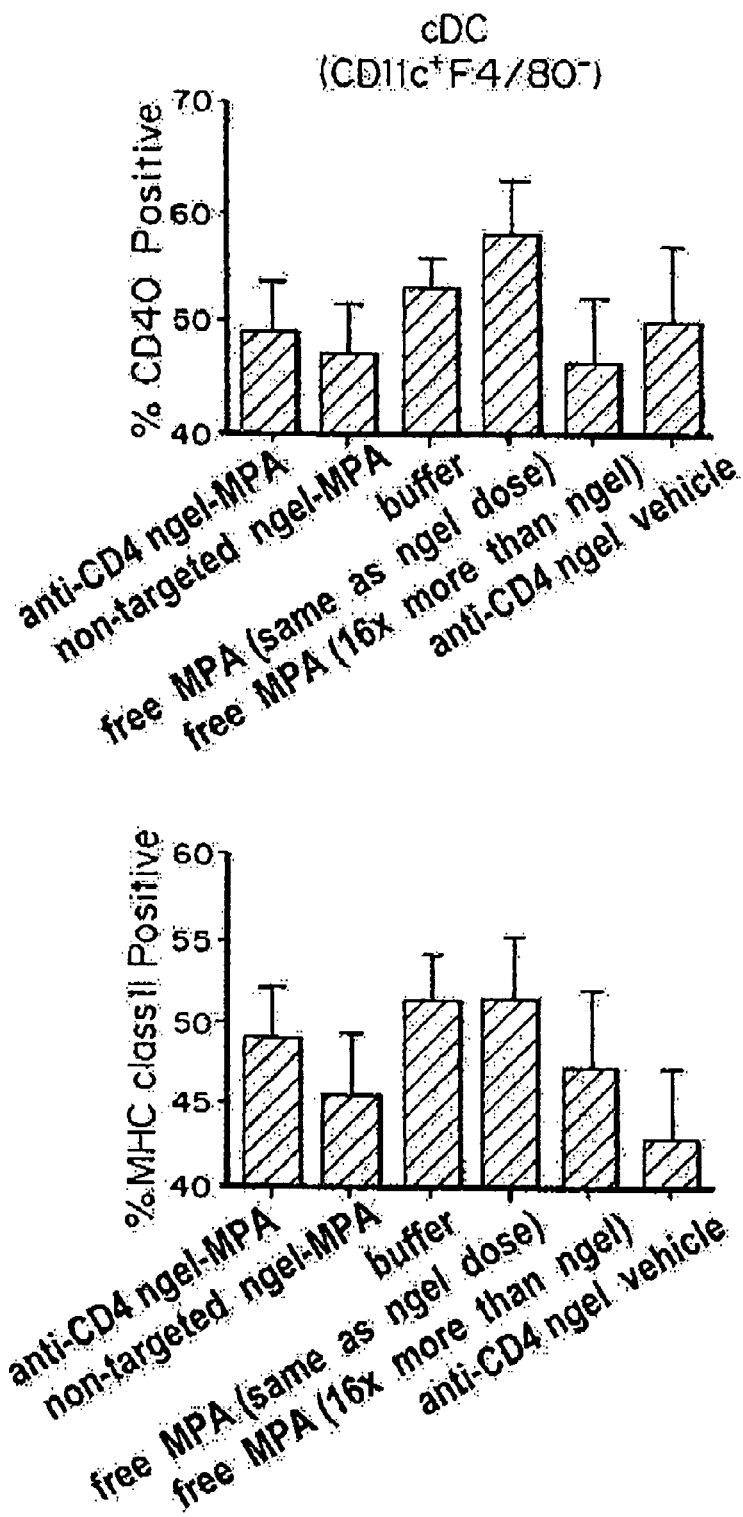
FIGS. 17A-17C are bar graphs showing the % CD40 positive (top graph) or % MHC class II positive (bottom graph) for conventional DC (CD11c+F4/80−) cells (17A), macrophages (F4/80+) (17B), or plasmacytoid DC (PDCA–1+F4/80−) cells (17C), harvested from 36-40-weeks-old mice that received anti-CD4 nanolipogel-MPA, non-targeted Nanolipogel-MPA, buffer, 0.625 mpk free MPA (same as nanolipogel dose), 10 mpk free MPA (16× nanolipogel dose), or anti-CD4 Nanolipogel vehicle beginning at 18-20 weeks of age. The sample size is n=6 to 15 animals per group. Error bars represent the standard error measurement.
Figure 17B:
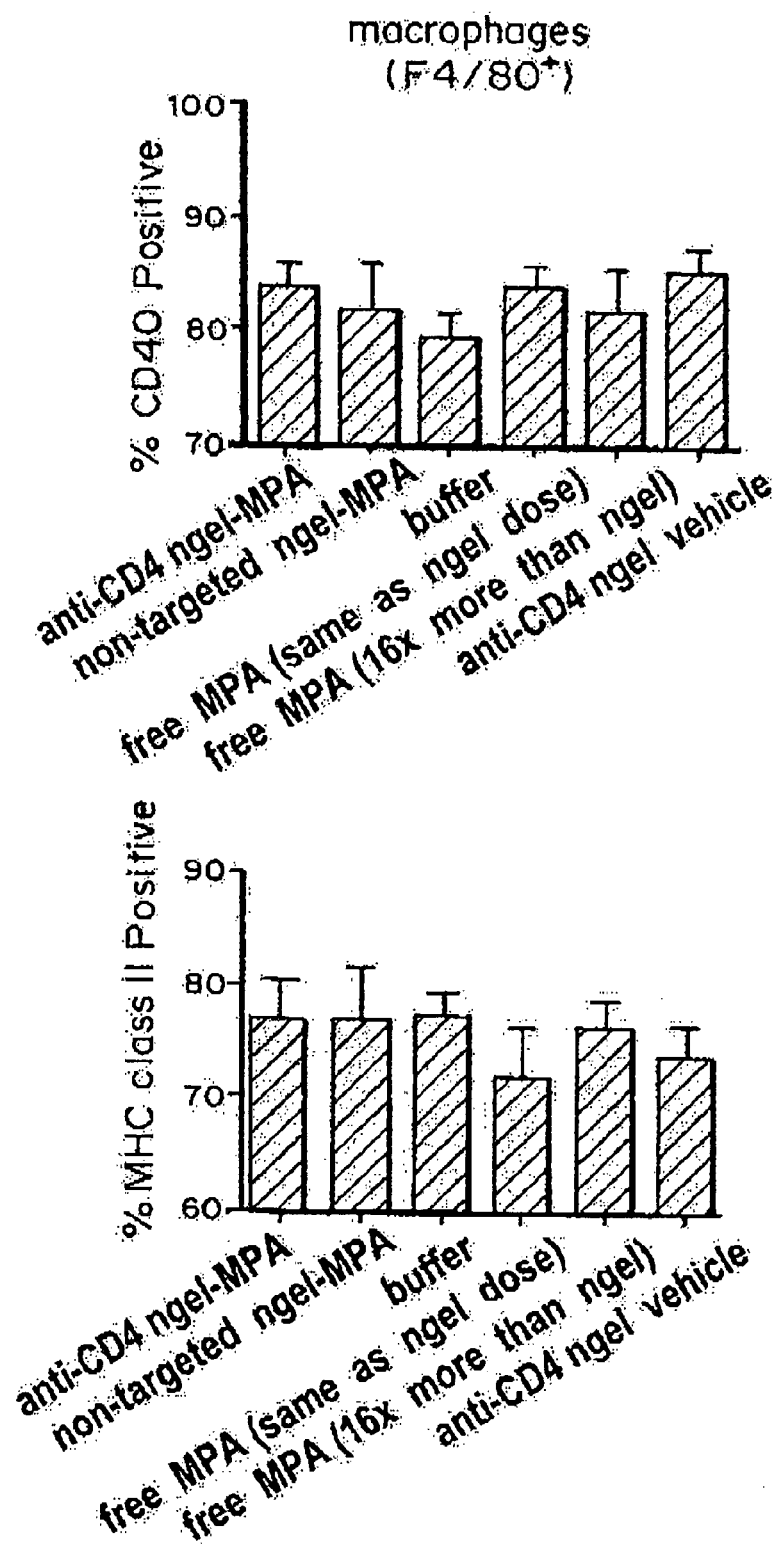
Figure 17C:
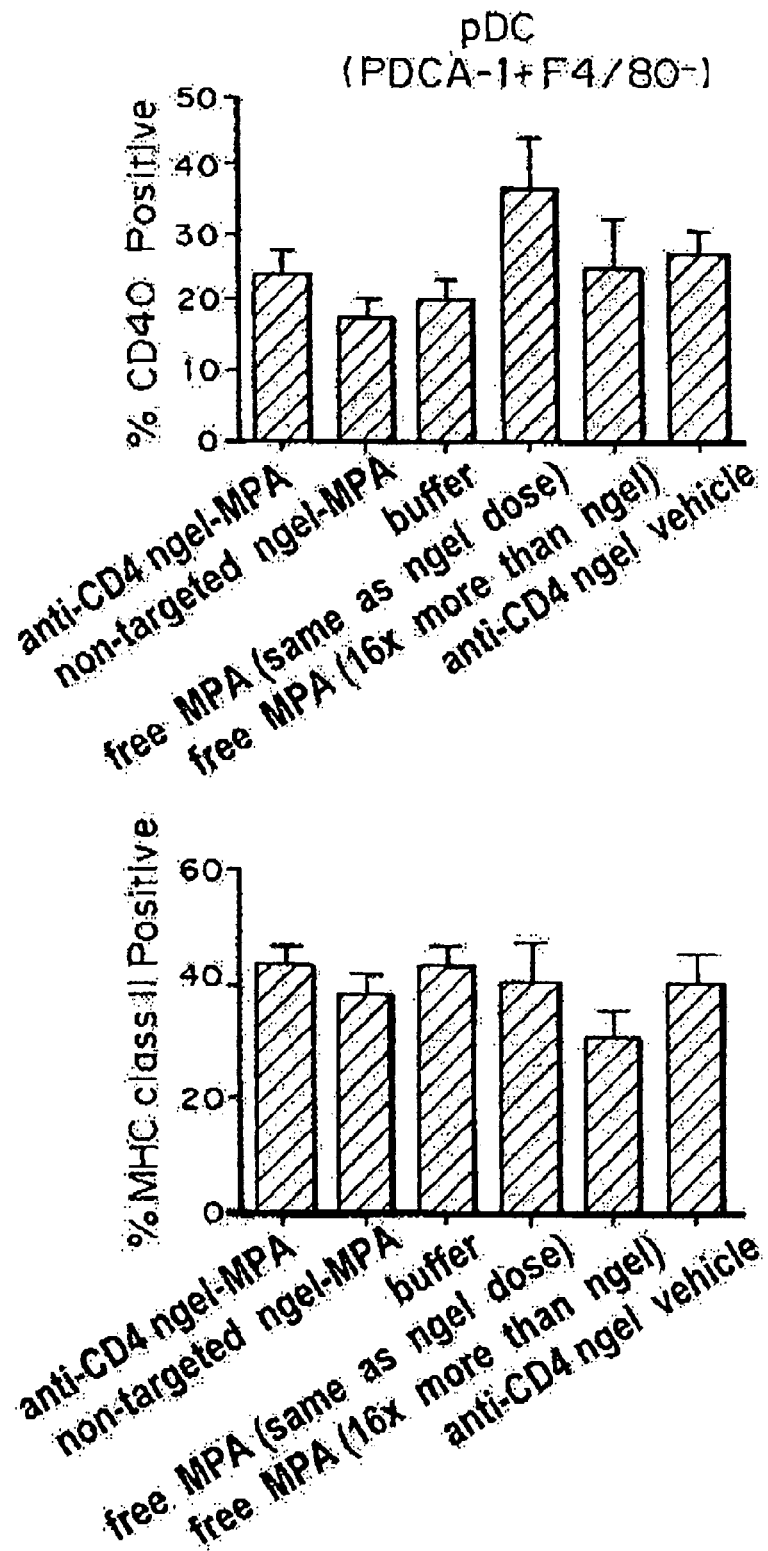

Conventional dendritic cells (cDC) also had mild reductions in expression of stimulatory markers such as CD40 and MHC II (FIG. 17A), respectively). This trend was not observed in macrophages (FIG. 17B) or plasmacytoid dendritic cells (FIG. 17C). Particulate-mediated reduction in stimulatory activity in cDCs may contribute to some of the therapeutic benefit observed. Consistent with the observations, prior reports indicate the cDCs may contribute to lupus pathology by stimulating T cell activation, but remain dispensable to early T cell-B cell interactions that result in autoantibody formation (Teichmann, et al., *Immunity*, 33(6): 967-78 (2010).

Example 16

Nanolipogel Immunosuppression Affects Dendritic Cell Populations

Dendritic cells can contribute to lupus disease pathology, and their in vivo depletion or pharmacological induction to a less inflammatory or even tolerogenic state may alleviate lupus autoimmunity. Because antigen presenting cells such as dendritic cells can internalize nanoparticles, the effect of MPA-loaded nanoparticles on dendritic cell maturation and activation was explored.

Materials and Methods

Bone marrow derived dendritic cells were treated with MPA-loaded nanoparticles and dendritic cell surface marker expression after stimulation with LPS, was measured. The effect of nanoparticle internalization plasmacytoid dendritic cells (pDC) inflammatory cytokine production was also investigated.

Bone Marrow Derived Dendritic Cell Culture and Mixed Lymphocyte Reaction Studies Bone marrow cells were isolated from the femurs and tibia of Balb/c mice, and then differentiated into $CD11c^+$ dendritic cells using 10 ng/mL GM-CSF (eBioscience) and 5 ng/mL IL-4 (eBioscience) in RPMI-1640 complete media (10 mM HEPES, 1 mM L-glutamine, 100 U/mL penicillin, 100 U/mL streptomycin, 50 μM β-mercaptoethanol), with 10% heat inactivated fetal bovine serum. These bone marrow dendritic cells (BMDCs) were dosed with nanoparticle therapy (125 ng/ml MPA), beginning at day 1 of culture. Media was changed thereafter every two days with fresh MPA-loaded particles in the media. On day 6 of the culture, BMDCs were replated at 200,000 cells/well in a 96-well round bottom plate, and then challenged with 50 ng/mL lipopolysaccharide (LPS) (Sigma) for 18 hr to induce further maturation. The BMDC purity after 7 days in culture was confirmed to be approximately 70% $CD11c^+$. For mixed lymphocyte reactions, day 7 BMDCs were irradiated with 3000 rad in an X-Rad 320 (Precision X-ray) and then co-cultured for 4 days in complete RPMI-1640 complete media with purified CD4 T cells from C57BL/6 mice at a ratio of $1\times10^5$ BMDCs to $2\times10^5$ CD4 T cells.

Samples for confocal imaging were prepared by seeding 7-days-old BMDCs onto ProbeOn Plus glass slides (Fisher), incubating with lissamine-rhodamine-labeled particles for 1 hr, and then staining cells with Alexa 488-phalloidin and TO-PRO-3 (Invitrogen). Cells were imaged with an LSM 510 Meta confocal microscope (Carl Zeiss)

For plasmacytoid dendritic cell studies, bone marrow cells were incubated with particles or free MPA for 30 min at 37° C. in RPMI-1640 complete media, washed, and then challenged with 1 μM CpG-A oligonucleotide (ODN 1585 from Invivogen) for 18 hr.

Cytokine Analysis

ELISAs for interleukin-10 (IL-10), interleukin 12p (IL-12p70), tumor necrosis factor α (TNF-α) (eBiosciences) and interleukin 2 (IL-2), interleukin 6 (IL-6), and interferon γ (IFN-γ) (BD Biosciences) were performed according to manufacturer's protocols. ELISAs for IL-1β and IFN-α were performed as previously described in (Demento, et al., *Vaccine*, 27(23):3013-21 (2009); Lund, et al., *J Exp Med*, 198(3):513-20 (2003), respectively.

Results

Figure 18A:
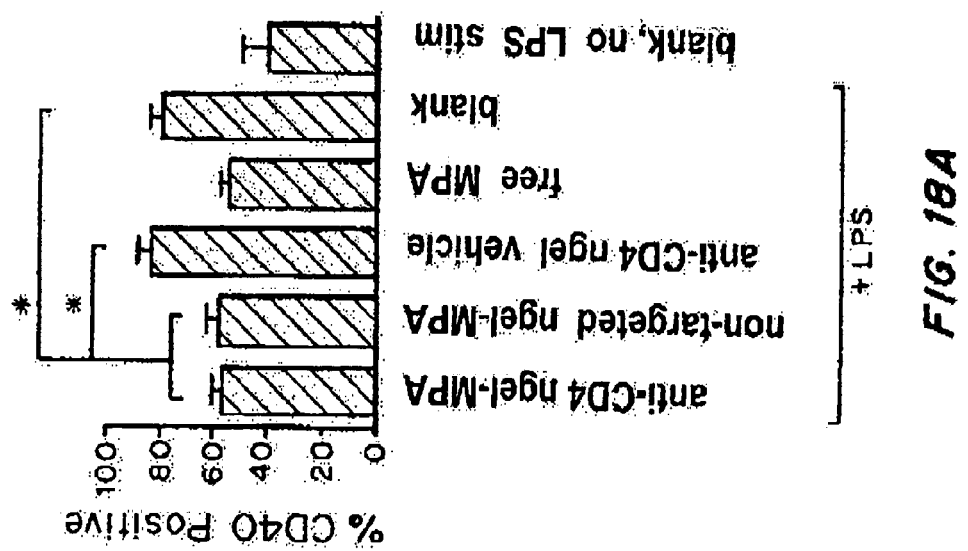
FIGS. 18A-18F are graphs of bone marrow derived dendritic cells (BMDCs): % CD40 positive (18A), % CD80 positive (18B), % CD86 positive (18C), interferon gamma (pg/ml) (18D), IL-12 p70 (pg/ml) (18E), TNF-alpha (pg/ml) (18F), % MHC class I positive (18G), and % MHC class II positive (18H) cultured in vitro for 7 days and treated on day 1 with anti-CD4 nanolipogel-MPA, non-targeted Nanolipogel-MPA, anti-CD4 Nanolipogel vehicle, free MPA, and control (blank) all stimulated with lipopolysaccharide (LPS) stimulation (50 ng/mL of LPS for 18 hr beginning on day 6), or control (blank) no LPS. Results are the average of 3 separate experiments, with error bars representing the standard error measurement. *p<0.05 or less by 1-way ANOVA using Bonferroni post-test.
Figure 18B:
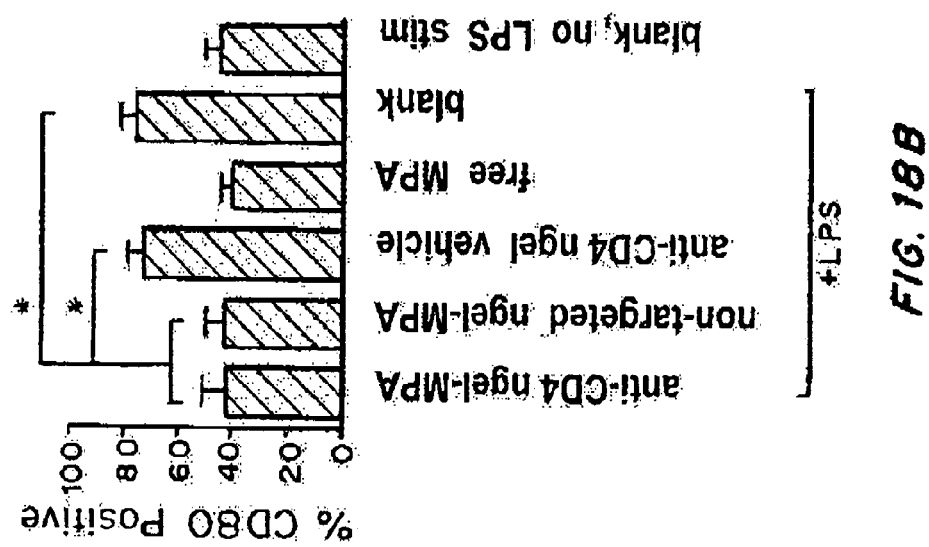
Figures 18C, 18D, 18E:
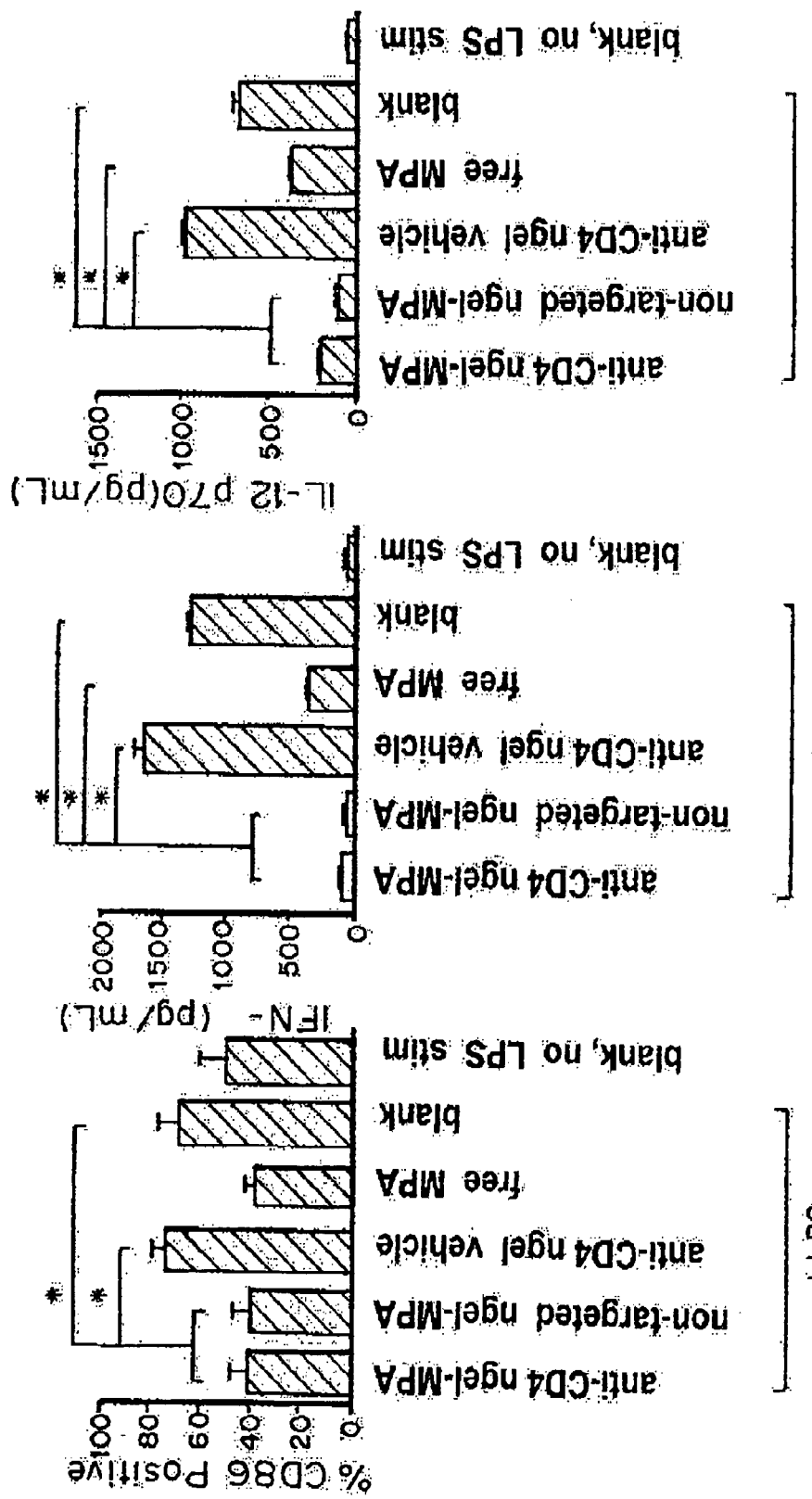
Figure 18F:
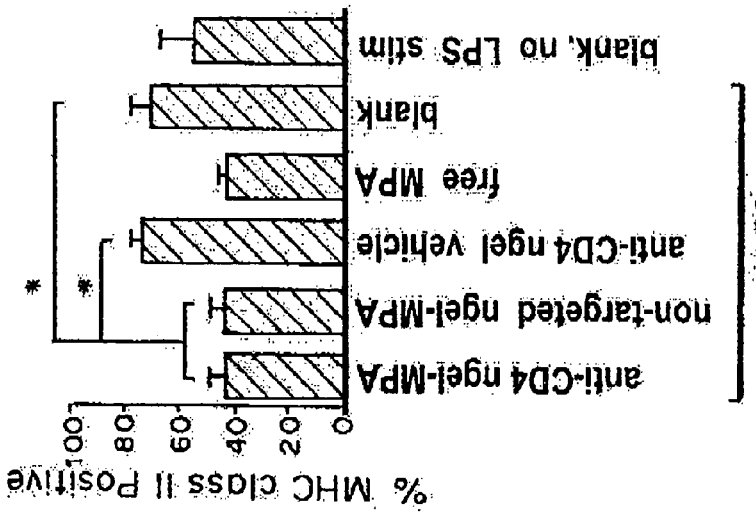
Figure 18G:
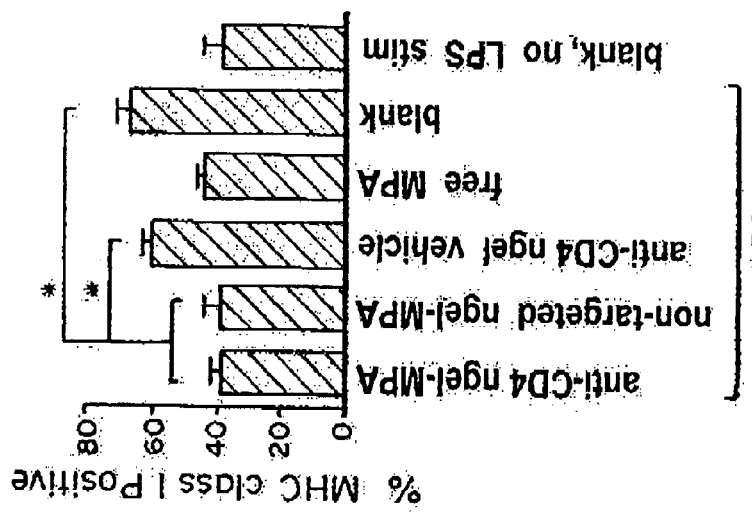
Figure 18H:
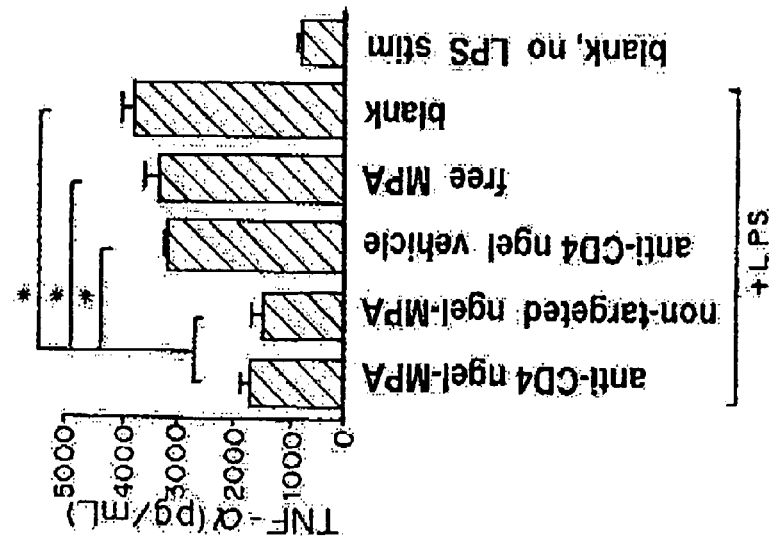
Figure 19A:
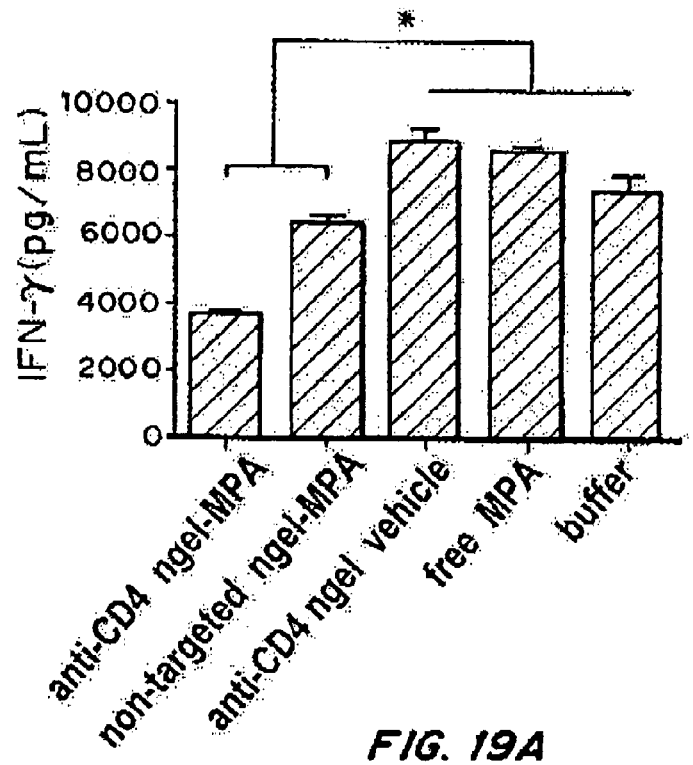
FIG. 19A is bar graph showing the level of interferon gamma (pg/ml) expressed from CD11c$^+$ cells isolated on day 8 from the spleens of Balb/c mice injected with treatment on day 0, 3, and 7, and subsequently from co-cultured for 4 days with with CD4 T cells at a ratio of 1×10$^5$ dendritic cells to 5×10$^5$ T cell. Treatment consisted of anti-CD4 nanolipogel-MPA, non-targeted Nanolipogel-MPA, anti-CD4 Nanolipogel vehicle, free MPA, and control. Error bars represent the standard deviation, with triplicate measurements from one representative experiment shown. *p<0.05 by ANOVA comparison with Bonferroni post-test. This experiment was repeated a total of 3 times, with similar trends.

Bone marrow derived dendritic cells treated with nanoparticles had decreased surface expression of the costimulatory markers CD40 (FIG. 18A), CD80 (FIG. 18B), and CD86 (FIG. 18C) as well as decreased expression of MHC class I and MHC class II molecules (FIGS. 18G and 18H). These dendritic cells also had decreased production of the inflammatory cytokines IFN-γ (FIG. 18D), IL-12p70 (FIG. 18E), and TNFα (FIG. 18F). The down-regulation of these surface markers and inflammatory cytokines may thus limit the ability of DCs to activate T cells. When MPA treated BMDCs were co-cultured with allogeneic CD4 T cells in a mixed lymphocyte reaction, the CD4 T cells had attenuated proliferation. Furthermore, these nanoparticle-treated dendritic cells could promote the partial expansion of CD25'Foxp3' CD4 T cells in vitro. Furthermore, CD11c+ dendritic cells isolated from wild type mice that were treated with nanogels elicited weaker production of IFN-γ from allogeneic CD4 T cells (FIG. 19A).

The suppression of dendritic cell activation markers by MPA is reversible in vitro, and requires the continued presence of MPA in media to maintain attenuated responses (Mehling, et al., *J. Immunol.*, 17:351-363 (2005)). Hence, the slight size of reduction in CD40 and MHC class II in vivo may be a consequence of the intermittence of weekly dosing. Much greater suppression was observed with constant nanogel exposure to cells in vitro.

Figure 19B:
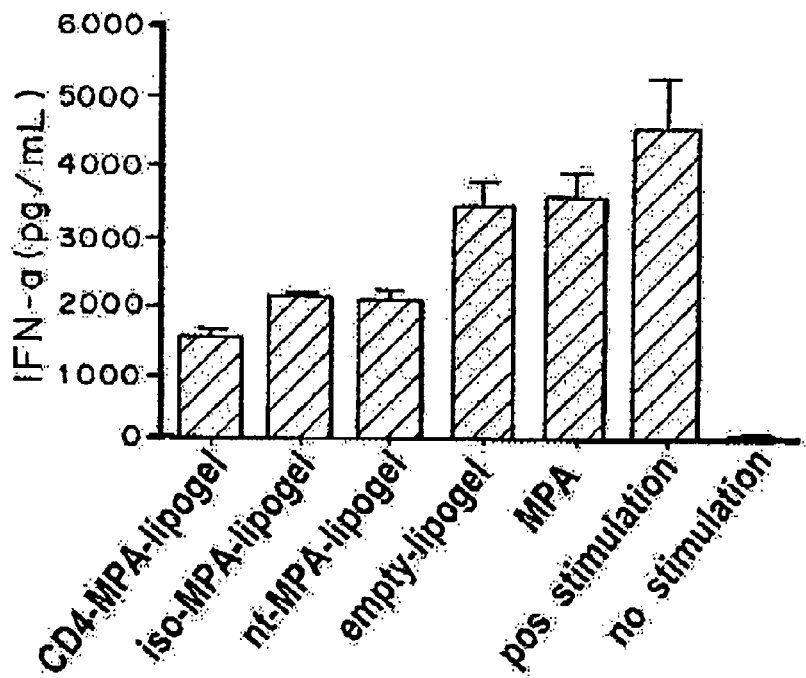
FIG. 19B is a bar graph showing the level of interferon alpha (pg/ml) expressed from bone marrow cells incubated with 1 μg/mL of MPA in nanogels for 1 hr at 37° C., washed, and then stimulated with CpG-A for 18 hr. Treatment consisted of anti-CD4 nanolipogel-MPA, non-targeted Nanolipogel-MPA, anti-CD4 Nanolipogel vehicle, free MPA, control (blank) with CpG-A and control (blank) without CpG-A. Data are averaged triplicates in one representative experiment from three repeated trials. Error bars are the standard deviation. *p<0.05 or less by 1-way ANOVA with Bonferroni multiple comparison post-test.

Plasmacytoid dendritic cells are potent producers of IFN-α, an inflammatory cytokine that exacerbates autoimmunity in mouse lupus models and human lupus patients. pDCs that were briefly treated with nanoparticles for 30 minutes and then challenged with CpG oligonucleotides had marked reduction in IFN-α production (FIG. 19B). Collectively, these results indicate that pharmacologic agent delivery with nanoparticles to conventional and plasmacytoid dendritic cells can attenuate their ability to promote aberrant inflammatory responses which contribute to autoimmunity.

Example 17

Nanolipogels Exhibit Improved Properties Over Conventional PLGA Nanoparticles

Materials and Methods

The efficacy of nanolipogels was compared to PLGA using both in vivo and in vitro evaluation. For in vivo evaluation, NZB/W F1 lupus-prone mice were treated with 0.625 mg MPA per kg animal with nanolipogels or PLGA particles. Survival time was monitored to determine and compare in vivo efficacy between particles.

For in vitro studies, bone marrow derived dendritic cells (BMDCs) were cultured. On day 1 of the culture, MPA loaded within nanolipogel or PLGA particles were added to cells. On day 6 of the culture, lipopolysaccharide was added, and dendritic cell surface markers were measured by flow cytometry. Levels of cytokine production was measured from the supernatant by ELISA.

For nanoparticle internalization studies, BMDCs were incubated for 1 hr with nanolipogels or PLGA particles containing fluorescent rhodamine tracer. The extent of nanoparticle internalization was assessed with flow cytometry, by quantifying the percentage of CD11c$^+$ cells that were positively labeled with rhodamine.

Results

The efficacy of MPA-loaded nanolipogel was also compared to conventional MPA-loaded PLGA nanoparticles and free MPA in the model for SLE.

Figure 20A:
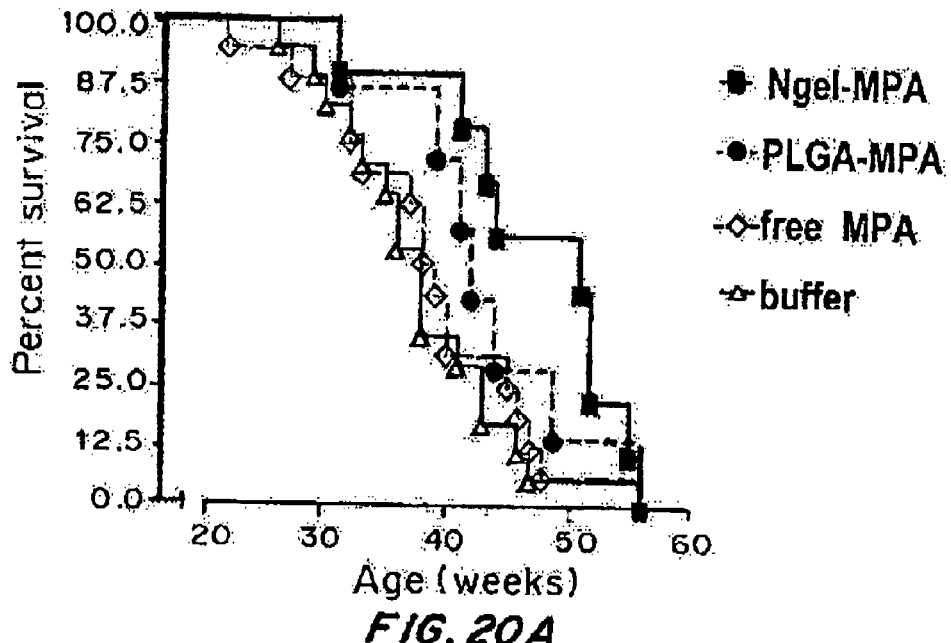
FIGS. 20A and 20B are a Kaplan-Meier survival curve (% survival) (20A) and a bar graph of mean survival age over time (age in weeks) (20B) of NZB/W F1 mice were treated with buffer control (-△-), nanolipogel-MPA (-■-), PLGA-MPA (-●-), and free MPA (-◇-).
Figure 20B:
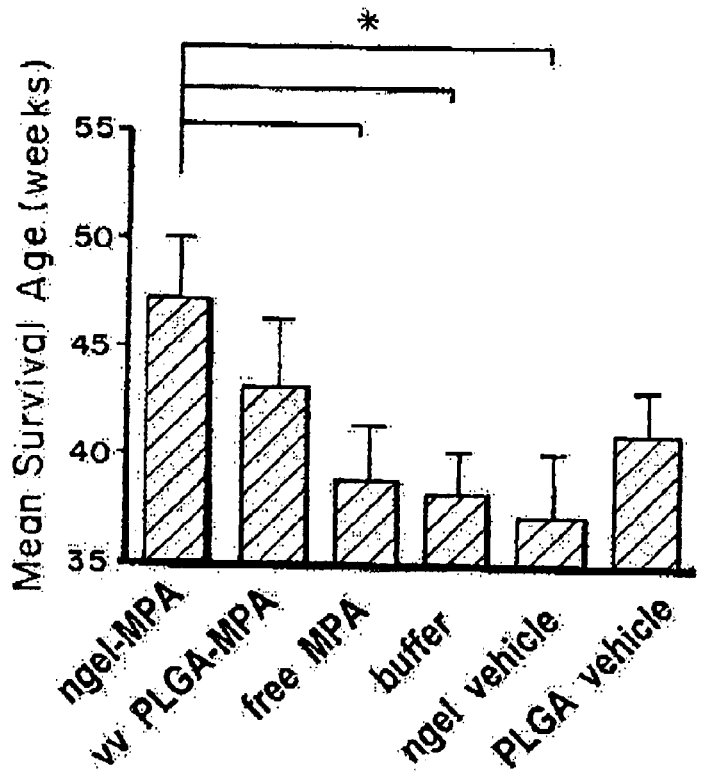
Figure 20D:
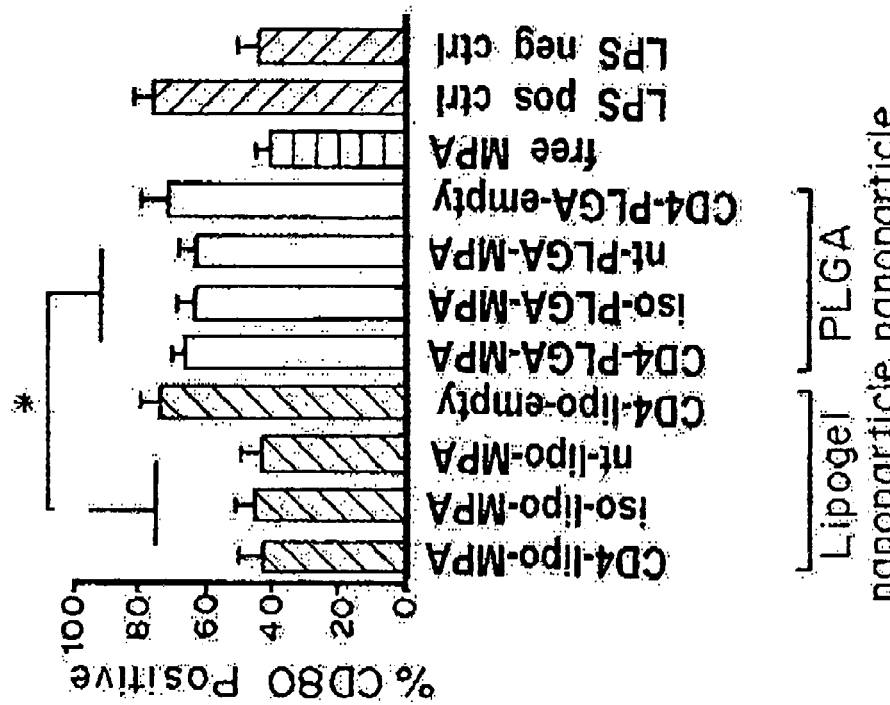
FIGS. 20C and 20D are bar graphs showing the % CD40 positive (20C) and % CD80 positive (20D) out of total dendritic cells treated with free MPA, or with MPA-loaded or empty nanolipogels (lipo) or PLGA nanoparticles, with no targeting (nt), anti-CD4 targeting, or isotype control targeting following LPS challenge. LPS positive and negative controls are also included. p<0.05 or less by 1-way ANOVA comparison.

The results show that nanolipogel loaded particles, but not PLGA loaded particles or free drug increased survival time to treated mice (FIGS. 20A and 20B).

Figure 20C:
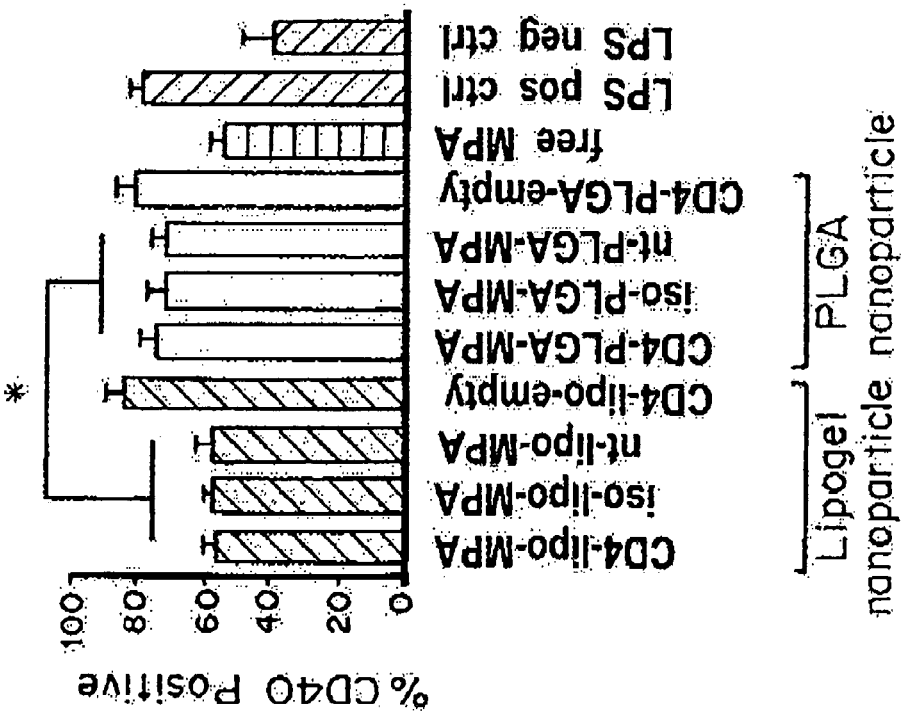

The results also show that nanolipogel loaded particles induce a greater reduction of immunostimulatory surface molecules on dendritic cells (% CD40 positive and % CD80 positive) than PLGA loaded particles after LPS challenge (FIGS. 20C and 20 D). Similar results were observed with CD86, MHC I, and MHC II.

Figure 20G:
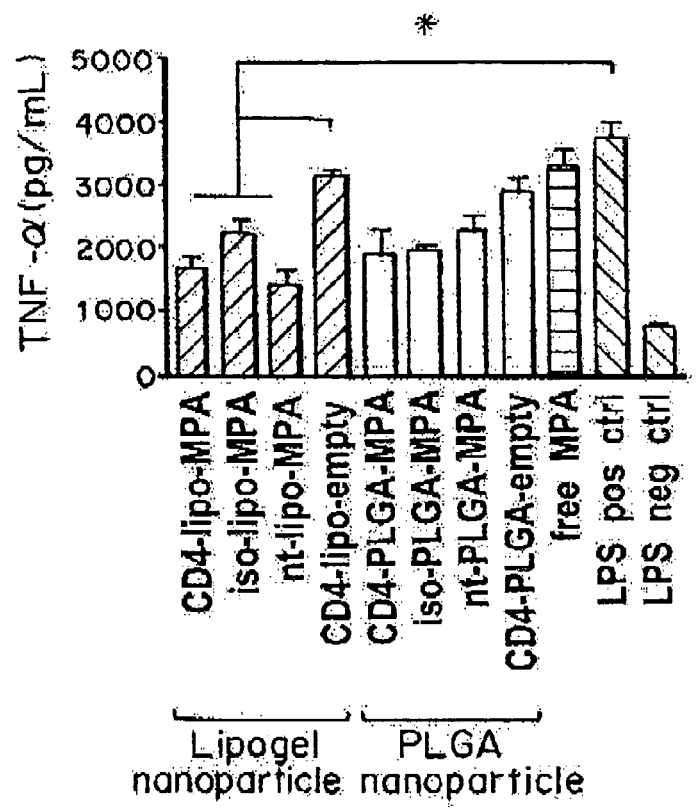

The results also show that nanolipogel loaded particles induce a greater reduction in proinflammatory cytokine production (i.e., IFN-γ, IL-12 p70, and TNF-α) in dendritic cells compared to PLGA loaded particles and free drug after LPS challenge (FIGS. 20E-20G).

Figure 20H:
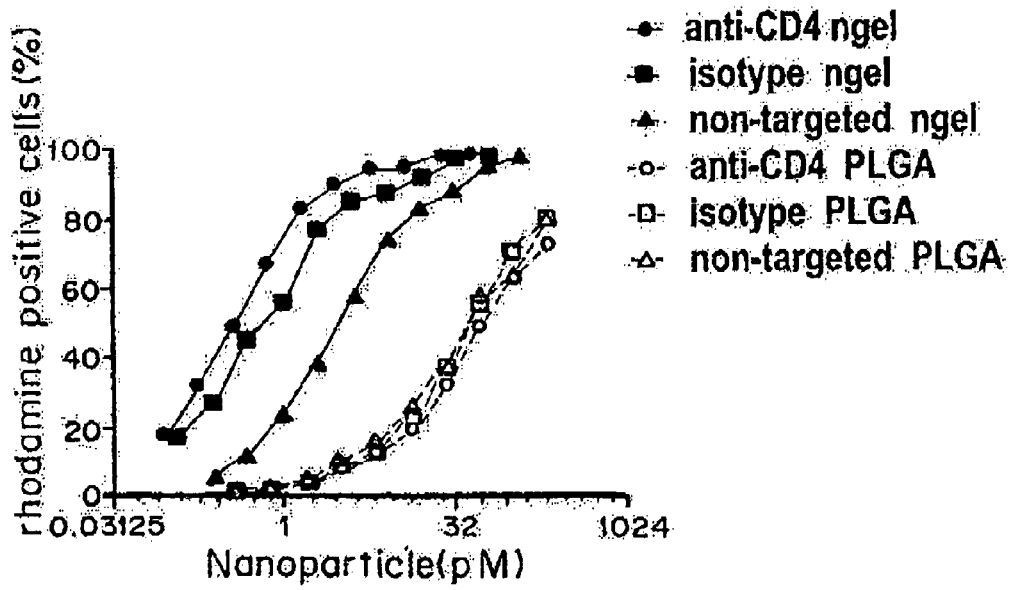
FIG. 20H is a line graph showing dendritic cell internalization (rhodamine positive %) as a function of nanoparticle dose (pM) for nanolipogels (ngel) or PLGA nanoparticles, with no targeting, anti-CD4 targeting, or isotype control.

It is believed that this result may be due in part to increased cell internalization of nanolipogels compared to PLGA nanoparticles (FIG. 20H).

Together, this data shows that nanolipogels exhibit increased efficacy over conventional PLGA nanoparticles.

Conclusion

Examples show development of a hydrogel-based nanoparticle ("nanolipogel") loaded with the immunosuppressant MPA. The studies also show that drug loaded nanogels can be used to achieve therapeutic immunosuppression in a lupus-prone mouse model. The use of these nanolipogels enhanced the potency of MPA therapy, as an equivalent dose of MPA administered without nanoparticles did not provide therapeutic benefit. Lupus median survival was enhanced by approximately 3 months, with delay in development of nephritis and partial attenuation in autoantibody production.

The administration of the drug in the nanogels requires significantly smaller dose for therapeutic efficacy, when compared to administration of the free drug. Significantly higher doses (>16-fold) of free drug could not achieve the same therapeutic result as smaller amounts of drug administered within nanoparticles.

These nanoparticles have defined interactions with immune cell subsets involved with lupus pathogenesis, and these immune cells can be affected by nanoparticle therapy. The data shows the ability of nanoparticles to more effectively traffic to spleen and target immune cell subsets involved with lupus pathogenesis than free drug. This enhancement in MPA bioavailability likely contributes to the improved therapeutic benefit observed with particles over freely administered MPA. All immune cell subsets appear to associate with nanoparticles to some extent in vivo, which results in overall reductions in inflammatory CD4 T cell responses at 36-40 weeks of age and ultimately delayed nephritis. Dendritic cell internalization of nanoparticles may contribute to this immunosuppression.

One of ordinary skill in the art can readily extend the results seen with nanogels in the examples, to delivery of pharmaceutical agent to treat and/or ameliorate the symptoms of other autoimmune diseases.

Modifications and variations of the compositions and methods of manufacture and use thereof will be obvious to those skilled in the art from the foregoing detailed description and are intended to come within the scope of the appended claims. All references are specifically incorporated.

We claim:

1. A method of treating a subject with an inflammatory, allergic, or autoimmune disease or disorder comprising administering to the subject a composition comprising an effective amount of nanolipogels comprising
   a polymeric matrix formed of crosslinked polymer, amphiphilic polymer, block copolymer, or tri-block copolymer having dispersed therein or covalently bound thereto one or more host molecules which reversibly complex with or bind an agent, wherein the host molecules are selected from the group consisting of one or more polysaccharides, cryptands, cryptophanes, cavitands, crown ethers, dendrimers, catenanes, carcerands, spherands, carbon nanotubes and fullerenes, for controlled release of at least one therapeutic, diagnostic or prophylactic agent, and a lipid shell;

wherein one or more active agents for reducing, decreasing, or alleviating one or more symptoms of the inflammatory, allergic, or autoimmune disease or disorder are reversibly complexed or bound to the host molecules, dispersed within the polymeric matrix, dispersed in or bound to the lipid shell, or combinations thereof.

2. The method of claim 1 wherein at least one of the active agents is an immunosuppressant.

3. The method of claim 2 wherein the immunosuppressant is Mycophenolate mofetil (MMF) or mycophenolic acid (MPA).

4. The method of claim 1 wherein the nanolipogel comprises at least one targeting ligand that increases the nanolipogel's specificity for a target cell.

5. The method of claim 4 wherein the targeting moiety is specific for CD4-positive T cells.

6. The method of claim 5 wherein the targeting moiety is an anti-CD4 antibody or antigen binding fragment thereof.

7. The method of claim 4 wherein the targeting moiety is specific for antigen presenting cells selected from the group consisting of macrophages, B cells, and monocytes.

8. The method of claim 7 wherein the antigen presenting cells are dendritic cells.

9. The method of claim 1 wherein the active agent is administered to the subject in an effective amount to decrease T cell proliferation.

10. The method of claim 1 wherein the active agent is administered to the subject in an effective amount to increase the tolerance of antigen presenting cells or decrease the ability of antigen presenting cells to activate T cells.

11. The method of claim 1 wherein the active agent is administered at a reduced dose to achieve the same or greater therapeutic benefit as administering free drug or PLGA nanoparticle-associated drug to the subject.

12. The method of claim 1 wherein toxicity in the subject is reduced compared to administering free drug to the subject.

13. The method of claim 1 wherein the disease or disorder is selected from the group consisting of rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, multiple sclerosis, myasthenia gravis, *pemphigus vulgaris*, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

14. The method of claim 1 wherein the disease is an allergy.

15. The method of claim 1 wherein the polymeric matrix, the lipid shell, or both are crosslinked, or wherein the polymeric matrix is formed of non-cross-linkable polymers.

16. The method of claim 1 wherein the polymeric matrix comprises polymer selected from the group consisting of poly(lactic acid); poly(glycolic acid); poly(lactic acid-co-glycolic acids); polyhydroxyalkanoates; polycaprolactones; poly(orthoesters); polyanhydrides; poly(phosphazenes); poly(lactide-co-caprolactones); poly(glycolide-co-caprolactones); polycarbonates; polyamides, polypeptides; poly(amino acids); polyesteramides; poly(dioxanones); poly(alkylene alkylates); hydrophilic polyethers; polyurethanes; polyetheresters; polyacetals; polycyanoacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids); polyvinyl alcohols; polyvinylpyrrolidone; poly(alkylene oxides); celluloses; polyacrylic acids; albumin; collagen; gelatin; prolamines; polysaccharides; polyethylene glycol (PEG); and derivatives; copolymers; and blends thereof.

17. The method of claim 1 wherein the host molecule is a cavitand selected from the group consisting of cyclodextrins, calixarenes, cucurbiturils, and spherands.

18. The method of claim 1 wherein the active agent is a small molecule, protein, polypeptide, polysaccharide, or nucleic acid.

19. The method of claim 1 where the lipid shell comprises one or more concentric lipid layers, optionally crosslinked, wherein the lipids can be neutral, anionic or cationic lipids at physiologic pH.

20. The method of claim 1 wherein the lipid is selected from the group consisting of cholesterol, phospholipids, lysolipids, lysophospholipids, and sphingolipids, and derivatives thereof.

21. The method of claim 20 comprising lipid selected from the group consisting of phosphatidylcholine; phosphatidylserine, phosphatidylglycerol, phosphatidylinositol; glycolipids; sphingomyelin, ceramide galactopyranoside, gangliosides, cerebrosides; fatty acids, sterols; 1,2-diacyl-sn-glycero-3-phosphoethanolamines, 1,2-dihexadecylphosphoethanolamine, 1,2-distearoylphosphatidylcholine, 1,2-dipalmitoylphosphatidylcholine, 1,2-dimyristoylphosphatidylcholine, N-[1-(2,3-dioleoyloxy)propyl]-N,N,N-trimethyl ammonium salts, dimethyldioctadecyl ammonium bromide, 1,2-diacyloxy-3-trimethylammonium propanes, N-[1-(2,3-dioloyloxy)propyl]-N,N-dimethyl amine, 1,2-diacyloxy-3-dimethylammonium propanes, N-[1-(2,3-dioleyloxy)propyl]-N,N,N-trimethylammonium chloride, 1,2-dialkyloxy-3-dimethylammonium propanes, dioctadecylamidoglycylspermine, 3-[N—(N',N'-dimethylamino-ethane)carbamoyl]cholesterol (DC-Chol); 2,3-dioleyloxy-N-(2-(sperminecarboxamido)-ethyl)-N,N-dimethyl-1-propanaminium trifluoro-acetate (DOSPA), β-alanyl cholesterol, cetyltrimethylammonium bromide (CTAB), diC$_{14}$-amidine, N-tert-butyl-N-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide, 1-[2-(acyloxy)ethyl]2-alkyl(alkenyl)-3-(2-hydroxyethyl)-imidazolinium chloride derivatives, such as 1-[2-(9(Z)-octadecenoyloxy)ethyl]-2-(8(Z)-heptadecenyl-3-(2-hydroxyethyl)imidazolinium chloride (DOTIM) and 1-[2-(hexadecanoyloxy)ethyl]-2-pentadecyl-3-(2-hydroxyethyl) imidazolinium chloride (DPTIM), and 2,3-dialkyloxypropyl quaternary ammonium derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

22. The method of claim 1 wherein the lipid is a PEGylated derivative of a neutral, anionic, or cationic lipid.

23. The method of claim 1 wherein the nanolipogel is made by a method comprising mixing the host molecule with the polymeric matrix and co-extruding the polymeric mixture with lipid.

24. The method of claim 23 wherein the nanolipogel comprises at least two active agents, wherein the first agent is loaded during formation of the nanolipogel and the second agent is loaded following formation by the process of rehydration of the polymeric matrix-host molecule in the presence of the second agent.

25. The method of claim 1 wherein the nanolipogel is administered intravenously, subcutaneously, intramuscularly, intraperitoneally, to the nasal or pulmonary system, to a mucosal surface or orally.

26. The method of claim 1, wherein the subject comprises a graft, and wherein the composition is administered in an effective amount to induce or increase graft tolerance in the subject.

27. The method of claim 1, wherein the polymeric matrix comprises block copolymer of polymers selected from the group consisting of aliphatic polyesters and poly(alkylene oxides).

28. The method of claim 27, wherein the polyhydroxyester comprises monomer selected from the group consisting of glycolic acid and lactic acid.

29. The method of claim 17, wherein the host molecule is a cyclodextrin.

30. The method of claim 1, wherein the host molecule is a natural polymer.

31. The method of claim 1, wherein the polymeric matrix comprises one or more photo-polymerizable groups.

32. The method of claim 1, wherein the composition comprises a hydrophobic small molecule agent.

33. The method of claim 1, wherein the composition comprises a hydrophilic agent.

34. The method of claim 33 wherein the composition comprises a peptide or polypeptide agent.

35. The method of claim 1 wherein the nanolipogels comprise a first active agent reversibly associated with a host molecule and a second active agent dispersed within the polymeric matrix core.

36. The method of claim 32 wherein the hydrophobic small molecule is a TGF-β inhibitor.

37. The method of claim 35 wherein the first active agent is a hydrophobic small molecule.

38. The method of claim 35 wherein the second active agent is a peptide.

39. The method of claim 37 wherein the polypeptide is IL-2.

40. The method of claim 1 wherein the polymer is biodegradable.

41. The method of claim 1 wherein the polymer is a diblock or tri-block copolymer.

42. The method of claim 1, wherein the polymeric matrix core is formed of a tri-block copolymer which contains a central poly(alkylene oxide) segment, adjoining aliphatic polyester segments attached to either end of the central poly(alkylene oxide) segment.

43. The method of claim 42, wherein the tri-block copolymer contains a central polyethylene glycol (PEG) segment, and adjoining aliphatic polyester segments which are selected from the group consisting of polyglycolic acid (PGA), polylactic acid (PLA) and polylactide coglycolide (PLGA).

44. The method of claim 29, wherein the host molecule is an unfunctionalized cyclodextrin or cyclodextrin functionalized with one or more pendant groups.

45. The method of claim 44, wherein the cyclodextrin is functionalized with one or more reactive functional groups that can react with the polymeric matrix core, wherein the reactive functional group is selected from the group consisting of methacrylate, acrylates, vinyl groups, epoxides, thiiranes, azides, alkynes, and combinations thereof; and/or wherein the cyclodextrin is functionalized with one or more reactive pendant groups that modify the solubility of the cyclodextrin, selected from the group consisting of sulfonyl, sulfonyl, phosphate, acyl, and C$_1$-C$_{12}$ alkyl groups.

46. The method of claim 44, wherein the cyclodextrin is selected from the group consisting of α-cyclodextrin; β-cyclodextrin; γ-cyclodextrin; methyl α-cyclodextrin; methyl β-cyclodextrin; methyl γ-cyclodextrin; ethyl β-cyclodextrin; butyl α-cyclodextrin; butyl β-cyclodextrin; butyl γ-cyclodextrin; pentyl γ-cyclodextrin; hydroxyethyl β-cyclodextrin; hydroxyethyl γ-cyclodextrin; 2-hydroxypropyl α-cyclodextrin; 2-hydroxypropyl β-cyclodextrin; 2-hydroxypropyl γ-cyclodextrin; 2-hydroxybulyl β-cyclodextrin; acetyl α-cyclodextrin; acetyl β-cyclodextrin; acetyl γ-cyclodextrin; propionyl β-cyclodextrin; butyryl β-cyclodextrin; succinyl α-cyclodextrin; succinyl β-cyclodextrin; succinyl γ-cyclodextrin; benzoyl β-cyclodextrin; palmityl β-cyclodextrin; toluenesulfonyl β-cyclodextrin; acetyl methyl β-cyclodextrin; acetyl butyl β-cyclodextrin; glucosyl α-cyclodextrin; glucosyl β-cyclodextrin; glucosyl γ-cyclodextrin; maltosyl α-cyclodextrin; maltosyl β-cyclodextrin; maltosyl γ-cyclodextrin; α-cyclodextrin carboxymethylether; β-cyclodextrin carboxymethylether; γ-cyclodextrin carboxymethylether; carboxymethylethyl β-cyclodextrin; phosphate ester α-cyclodextrin; phosphate ester β-cyclodextrin; phosphate ester γ-cyclodextrin; 3-trimethylammonium-2-hydroxypropyl β-cyclodextrin; sulfobutyl ether β-cyclodextrin; carboxymethyl α-cyclodextrin; carboxymethyl β-cyclodextrin; carboxymethyl γ-cyclodextrin, and combinations thereof.

47. The method of claim 44, when the cyclodextrin is selected from the group consisting of α-cyclodextrins, β-cyclodextrins, and γ-cyclodextrins functionalized with one or more pendant acrylate or methacrylate groups.

48. The method of claim 44, when the cyclodextrin is β-cyclodextrin functionalized with pendant acrylate or methacrylate groups, or is 2-hydroxypropyl β-cyclodextrin.

49. The method of claim 42, wherein the tri-block copolymer is cross-linked.

50. The method of claim 42, wherein the tri-block copolymer comprises one or more photo-polymerizable groups.

51. The method of claim 42, wherein the poly (alkylene oxide) segments are polyethylene glycol, polypropylene 1,2-glycol, poly (propylene oxide), and/or polypropylene 1,3-glycol segments and the aliphatic polyester segments are polylactic acid (PLA), polyglycolic acid (PGA), and/or polylactide-coglycolides (PLGA) segments.

52. The method of claim 1, wherein the nanolipogels comprise one or more cross-linked polymers which are covalently cross-linked by one or more photo-polymerisable groups.

53. The method of claim 51, wherein the photo-polymerisable groups are selected from the group consisting of vinyl groups, acrylate groups, methacrylate groups and acrylamide groups.

54. The method of claim 1, wherein the agent is selected from the group consisting of antibiotics, antivirals, antiparasitics, cytokines, growth factors, growth inhibitors, hormones, hormone antagonists, antibodies and bioactive fragments thereof, antigen and vaccine formulations, anti-inflammatories, immunomodulators, and oligonucleotide drugs, paramagnetic molecules, fluorescent compounds, magnetic molecules, and radionuclides, x-ray imaging agents, and contrast agents.

55. The method of claim 54, wherein the agent is a ligand that binds to an immunologic danger signaling molecule.

56. The method of claim 54, wherein the agent is an antibody or fragment thereof.

57. The method of claim 36, wherein the small molecule is a small chemical entity less than 1200 g/mole which interacts with the host molecule by hydrophobic, van-der waals, electrostatic or hydrogen bonds.

58. The method of claim 54 wherein the agent is selected from the group consisting of alkylating agents, antimetabolite, antimitotics, anthracyclines, cytotoxic antibiotics, topoisomerase inhibitors, antibodies to vascular endothelial growth factor; thalidomide; endostatin; angiostatin; receptor tyrosine kinase (RTK) inhibitors; tyrosine kinase inhibitors; transforming growth factor-α or transforming growth factor-β inhibitors, and antibodies to the epidermal growth factor receptor.

* * * * *

UNITED STATES PATENT AND TRADEMARK OFFICE
CERTIFICATE OF CORRECTION

PATENT NO. : 9,603,800 B2
APPLICATION NO. : 14/394147
DATED : March 28, 2017
INVENTOR(S) : Tarek M. Fahmy, Michael Look and Joseph Craft Page 1 of 1

It is certified that error appears in the above-identified patent and that said Letters Patent is hereby corrected as shown below:

In the Specification

Column 1, Lines 19-28 should read as follows:
This invention was made with government support under AI056363 awarded by National Institutes of Health and under 0644492 awarded by the National Science Foundation. The government has certain rights in the invention.

Signed and Sealed this
Thirtieth Day of June, 2020

Andrei Iancu
*Director of the United States Patent and Trademark Office*